US012577240B2

(12) United States Patent
Owen et al.

(10) Patent No.: US 12,577,240 B2
(45) Date of Patent: Mar. 17, 2026

(54) ANTIVIRAL HETEROARYL KETONE DERIVATIVES

(71) Applicant: Pfizer Inc., New York, NY (US)

(72) Inventors: Dafydd Rhys Owen, Concord, MA (US); Martin Youngjin Pettersson, Littleton, MA (US); Matthew Richard Reese, Mystic, CT (US); Matthew Forrest Sammons, Quincy, MA (US); Jamison Bryce Tuttle, Marblehead, MA (US); Qingyi Yang, Lexington, MA (US)

(73) Assignee: Pfizer Inc., New York, NY (US)

( * ) Notice: Subject to any disclaimer, the term of this patent is extended or adjusted under 35 U.S.C. 154(b) by 580 days.

(21) Appl. No.: 18/004,996

(22) PCT Filed: Jul. 7, 2021

(86) PCT No.: PCT/IB2021/056093
§ 371 (c)(1),
(2) Date: Jan. 10, 2023

(87) PCT Pub. No.: WO2022/013684
PCT Pub. Date: Jan. 20, 2022

(65) Prior Publication Data

US 2023/0339930 A1 Oct. 26, 2023

Related U.S. Application Data

(60) Provisional application No. 63/050,766, filed on Jul. 11, 2020.

(51) Int. Cl.
*C07D 417/14* (2006.01)
*A61P 31/14* (2006.01)

(52) U.S. Cl.
CPC ............ *C07D 417/14* (2013.01); *A61P 31/14* (2018.01)

(58) Field of Classification Search
CPC ............................... C07D 417/14; A61P 31/14
See application file for complete search history.

(56) References Cited

U.S. PATENT DOCUMENTS

| | | | |
|---|---|---|---|
| 5,583,238 | A | 12/1996 | Ng et al. |
| 6,037,157 | A | 3/2000 | Norbeck et al. |
| 6,514,997 | B2 | 2/2003 | Dragovich et al. |
| 6,894,072 | B2 | 5/2005 | Arasappan et al. |
| 7,012,066 | B2 | 3/2006 | Saksena et al. |
| 7,173,057 | B2 | 2/2007 | Chen et al. |
| 7,186,747 | B2 | 3/2007 | Arasappan et al. |
| 7,205,330 | B2 | 4/2007 | Bogen et al. |
| 7,244,721 | B2 | 7/2007 | Saksena et al. |
| 7,423,058 | B2 | 9/2008 | Bogen et al. |
| 7,425,576 | B2 | 9/2008 | Arasappan et al. |
| 7,449,447 | B2 | 11/2008 | Chen et al. |
| 7,485,625 | B2 | 2/2009 | Velazquez et al. |
| 7,504,392 | B2 | 3/2009 | Fobes et al. |
| 7,592,316 | B2 | 9/2009 | Njoroge et al. |
| 7,619,094 | B2 | 11/2009 | Chen et al. |
| 7,816,326 | B2 | 10/2010 | Velazquez et al. |
| 8,067,379 | B2 | 11/2011 | Bennett et al. |
| RE43,298 | E | 4/2012 | Saksena et al. |
| 8,686,145 | B2 | 4/2014 | Ruijter et al. |
| 9,309,284 | B2 | 4/2016 | Chang et al. |
| 9,474,759 | B2 | 10/2016 | Chang et al. |
| 9,884,876 | B2 | 2/2018 | Iadonato et al. |
| 9,975,885 | B2 | 5/2018 | St. John et al. |
| 11,072,634 | B2 | 7/2021 | Hils et al. |
| 11,124,497 | B1 | 9/2021 | Arnold et al. |
| 11,174,231 | B1 | 11/2021 | Arnold et al. |
| 11,351,149 | B2 | 6/2022 | Owen et al. |
| 11,358,953 | B2 | 6/2022 | Panarese et al. |
| 11,452,711 | B2 | 9/2022 | Owen et al. |
| 11,541,034 | B2 | 1/2023 | Owen et al. |
| 2003/0207861 | A1 | 11/2003 | Arasappan et al. |
| 2003/0216325 | A1 | 11/2003 | Saksena et al. |
| 2004/0186114 | A1 | 9/2004 | Girillo et al. |
| 2004/0235952 | A1 | 11/2004 | Fuhrman et al. |
| 2004/0254117 | A9 | 12/2004 | Saksena et al. |
| 2005/0085425 | A1 | 4/2005 | Chen et al. |

(Continued)

FOREIGN PATENT DOCUMENTS

| | | |
|---|---|---|
| CN | 102838523 | 12/2012 |
| CN | 103130710 | 6/2013 |

(Continued)

OTHER PUBLICATIONS

Cui, J., Li, F. & Shi, ZL. Origin and evolution of pathogenic coronaviruses. Nat Rev Microbiol 17, 181-192 (2019). https://doi.org/10.1038/s41579-018-0118-9 (Year: 2019).*

(Continued)

*Primary Examiner* — Fereydoun G Sajjadi
*Assistant Examiner* — Anna Grace Kuckla
(74) *Attorney, Agent, or Firm* — John A. Wichtowski

(57) ABSTRACT

The invention relates to compounds of Formula I

I

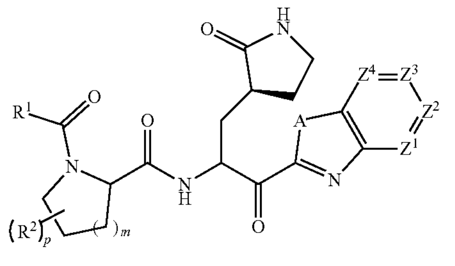

wherein $R^1$, $R^2$, p, m, A, $Z^1$, $Z^2$, $Z^3$ and $Z^4$ are as defined herein, pharmaceutical compositions comprising the compounds, methods of treating COVID-19 in a patient by administering therapeutically effective amounts of the compounds, and methods of inhibiting or preventing replication of SARS-CoV-2 with the compounds.

27 Claims, No Drawings

Specification includes a Sequence Listing.

(56) References Cited

U.S. PATENT DOCUMENTS

| | | | |
|---|---|---|---|
| 2005/0143319 | A1 | 6/2005 | Yang et al. |
| 2005/0143320 | A1 | 6/2005 | Yang et al. |
| 2005/0153900 | A1 | 7/2005 | Velazquez et al. |
| 2005/0222047 | A1 | 10/2005 | Chen et al. |
| 2005/0245458 | A1 | 11/2005 | Arasappan et al. |
| 2005/0267043 | A1 | 12/2005 | Bogen et al. |
| 2005/0267148 | A1 | 12/2005 | Tsuchiya et al. |
| 2005/0288338 | A1 | 12/2005 | Yao et al. |
| 2006/0014821 | A1 | 1/2006 | He et al. |
| 2006/0205672 | A1 | 9/2006 | Saksena et al. |
| 2006/0276406 | A1 | 12/2006 | Gupta et al. |
| 2006/0281689 | A1 | 12/2006 | Malcolm |
| 2007/0032433 | A1 | 2/2007 | Saksena et al. |
| 2007/0042968 | A1 | 2/2007 | Bennett et al. |
| 2007/0093430 | A1 | 4/2007 | Chen et al. |
| 2007/0142300 | A1 | 6/2007 | Arasappan et al. |
| 2007/0142301 | A1 | 6/2007 | Bogen et al. |
| 2007/0197448 | A1 | 8/2007 | Velazquez et al. |
| 2007/0232549 | A1 | 10/2007 | Njoroge et al. |
| 2010/0160320 | A1 | 6/2010 | Fan et al. |
| 2010/0311753 | A1 | 12/2010 | Fan et al. |
| 2011/0117057 | A1 | 5/2011 | Saksena et al. |
| 2012/0329704 | A1 | 12/2012 | Ruijter et al. |
| 2012/0330015 | A1 | 12/2012 | Ruijter et al. |
| 2013/0018045 | A1 | 1/2013 | Woods et al. |
| 2013/0310555 | A1 | 11/2013 | Chong |
| 2014/0005168 | A1 | 1/2014 | Do et al. |
| 2014/0213788 | A1 | 7/2014 | Ruijter et al. |
| 2014/0243341 | A1 | 8/2014 | Chang et al. |
| 2015/0133368 | A1 | 5/2015 | Chang et al. |
| 2015/0148342 | A1 | 5/2015 | Yue et al. |
| 2015/0210665 | A1 | 7/2015 | Rawat et al. |
| 2017/0008863 | A1 | 1/2017 | Chong |
| 2017/0355708 | A1 | 12/2017 | Jefson et al. |
| 2018/0289676 | A1 | 10/2018 | Arnatt et al. |
| 2019/0016726 | A1 | 1/2019 | Lin et al. |
| 2019/0151400 | A1 | 5/2019 | Chang et al. |
| 2019/0282703 | A1 | 9/2019 | Gallatin et al. |
| 2019/0322700 | A1 | 10/2019 | Hils et al. |
| 2020/0157078 | A1 | 5/2020 | Fan et al. |
| 2021/0008150 | A1 | 1/2021 | Schinazi et al. |
| 2022/0017548 | A1 | 1/2022 | Kania et al. |
| 2022/0033383 | A1 | 2/2022 | Panarese et al. |

FOREIGN PATENT DOCUMENTS

| | | |
|---|---|---|
| CN | 103145608 | 6/2013 |
| CN | 105037367 | 11/2015 |
| CN | 110054596 | 7/2019 |
| CN | 110105348 | 8/2019 |
| CN | 108690043 | 10/2019 |
| CN | 110818691 | 2/2020 |
| CN | 105566321 | 4/2020 |
| CN | 107459511 | 5/2020 |
| CN | 108069984 | 2/2021 |
| DE | 19748470 | 5/1999 |
| EA | 032794 | 7/2019 |
| EP | 3342779 | 4/2018 |
| FR | 3037955 | 12/2016 |
| GB | 2422829 | 8/2006 |
| GB | 2422831 | 8/2006 |
| GB | 2548542 | 9/2017 |
| JP | 2008260716 | 10/2008 |
| JP | 2013032343 | 2/2013 |
| JP | 2014133739 | 7/2014 |
| JP | 2015151458 | 8/2015 |
| JP | 2017137291 | 8/2017 |
| WO | 1994014436 | 7/1994 |
| WO | 1996012817 | 5/1996 |
| WO | 1997030073 | 8/1997 |
| WO | 1997031937 | 9/1997 |
| WO | 1997037997 | 10/1997 |
| WO | 2000003997 | 1/2000 |
| WO | 2001010894 | 2/2001 |
| WO | 2001040189 | 6/2001 |
| WO | 2002008244 | 1/2002 |
| WO | 2003053988 | 7/2003 |
| WO | 2003062228 | 7/2003 |
| WO | 2003062265 | 7/2003 |
| WO | 2003074532 | 9/2003 |
| WO | 2003080633 | 10/2003 |
| WO | 2003104202 | 12/2003 |
| WO | 2003105666 | 12/2003 |
| WO | 2004020441 | 3/2004 |
| WO | 2004058717 | 7/2004 |
| WO | 2004093860 | 11/2004 |
| WO | 2004098600 | 11/2004 |
| WO | 2005009479 | 2/2005 |
| WO | 2005021584 | 3/2005 |
| WO | 2005023294 | 3/2005 |
| WO | 2005058821 | 6/2005 |
| WO | 2005074598 | 8/2005 |
| WO | 2005085242 | 9/2005 |
| WO | 2005085275 | 9/2005 |
| WO | 2005087725 | 9/2005 |
| WO | 2005087731 | 9/2005 |
| WO | 2005113580 | 12/2005 |
| WO | 2006024820 | 3/2006 |
| WO | 2006035067 | 4/2006 |
| WO | 2006035068 | 4/2006 |
| WO | 2006045828 | 5/2006 |
| WO | 2006061714 | 6/2006 |
| WO | 2006108488 | 10/2006 |
| WO | 2006108489 | 10/2006 |
| WO | 2006130552 | 12/2006 |
| WO | 2006130626 | 12/2006 |
| WO | 2007039802 | 4/2007 |
| WO | 2007057092 | 5/2007 |
| WO | 2007058832 | 5/2007 |
| WO | 2007068465 | 6/2007 |
| WO | 2007104560 | 9/2007 |
| WO | 2007115409 | 10/2007 |
| WO | 2007120160 | 10/2007 |
| WO | 2007126362 | 11/2007 |
| WO | 2008011074 | 1/2008 |
| WO | 2008037266 | 4/2008 |
| WO | 2008040820 | 4/2008 |
| WO | 2008055959 | 5/2008 |
| WO | 2008077551 | 7/2008 |
| WO | 2008077554 | 7/2008 |
| WO | 2008104994 | 9/2008 |
| WO | 2008124148 | 10/2008 |
| WO | 2008126889 | 10/2008 |
| WO | 2008147812 | 12/2008 |
| WO | 2009061761 | 5/2009 |
| WO | 2009138789 | 11/2009 |
| WO | 2009138790 | 11/2009 |
| WO | 2009138791 | 11/2009 |
| WO | 2009138792 | 11/2009 |
| WO | 2009138795 | 11/2009 |
| WO | 2009138796 | 11/2009 |
| WO | 2009146406 | 12/2009 |
| WO | 2010014179 | 2/2010 |
| WO | 2010039982 | 4/2010 |
| WO | 2010042646 | 4/2010 |
| WO | 2010042649 | 4/2010 |
| WO | 2010107997 | 9/2010 |
| WO | 2010111060 | 9/2010 |
| WO | 2010138652 | 12/2010 |
| WO | 2010138659 | 12/2010 |
| WO | 2010138685 | 12/2010 |
| WO | 2010138695 | 12/2010 |
| WO | 2010138706 | 12/2010 |
| WO | 2010144686 | 12/2010 |
| WO | 2011003932 | 1/2011 |
| WO | 2011011303 | 1/2011 |
| WO | 2011014817 | 2/2011 |
| WO | 2011018170 | 2/2011 |
| WO | 2011087837 | 7/2011 |
| WO | 2011088303 | 7/2011 |
| WO | 2011088345 | 7/2011 |
| WO | 2011103932 | 9/2011 |
| WO | 2011103933 | 9/2011 |
| WO | 2011132048 | 10/2011 |

(56) References Cited

FOREIGN PATENT DOCUMENTS

| | | |
|---|---|---|
| WO | 2011133659 | 10/2011 |
| WO | 2011146748 | 11/2011 |
| WO | 2012022045 | 2/2012 |
| WO | 2012028578 | 3/2012 |
| WO | 2012058173 | 5/2012 |
| WO | 2012058531 | 5/2012 |
| WO | 2012087372 | 6/2012 |
| WO | 2012125668 | 9/2012 |
| WO | 2012151271 | 11/2012 |
| WO | 2012151283 | 11/2012 |
| WO | 2012169649 | 12/2012 |
| WO | 2012171337 | 12/2012 |
| WO | 2013026726 | 2/2013 |
| WO | 2013049382 | 4/2013 |
| WO | 2013087581 | 6/2013 |
| WO | 2013100632 | 7/2013 |
| WO | 2013128465 | 9/2013 |
| WO | 2013155422 | 10/2013 |
| WO | 2013157229 | 10/2013 |
| WO | 2013166319 | 11/2013 |
| WO | 2013181135 | 12/2013 |
| WO | 2013185124 | 12/2013 |
| WO | 2014076170 | 5/2014 |
| WO | 2014078214 | 5/2014 |
| WO | 2014113620 | 7/2014 |
| WO | 2014172871 | 10/2014 |
| WO | 2015028427 | 3/2015 |
| WO | 2015036058 | 3/2015 |
| WO | 2015036059 | 3/2015 |
| WO | 2015049351 | 4/2015 |
| WO | 2015104254 | 7/2015 |
| WO | 2015110481 | 7/2015 |
| WO | 2015110826 | 7/2015 |
| WO | 2015143653 | 10/2015 |
| WO | 2015155332 | 10/2015 |
| WO | 2015192981 | 12/2015 |
| WO | 2015193454 | 12/2015 |
| WO | 2016033243 | 3/2016 |
| WO | 2016050921 | 4/2016 |
| WO | 2016079760 | 5/2016 |
| WO | 2016123576 | 8/2016 |
| WO | 2016124796 | 8/2016 |
| WO | 2016124938 | 8/2016 |
| WO | 2016133832 | 8/2016 |
| WO | 2016134314 | 8/2016 |
| WO | 2017018924 | 2/2017 |
| WO | 2017060431 | 4/2017 |
| WO | 2017114509 | 7/2017 |
| WO | 2017155816 | 9/2017 |
| WO | 2017165311 | 9/2017 |
| WO | 2017193034 | 11/2017 |
| WO | 2017193041 | 11/2017 |
| WO | 2017193063 | 11/2017 |
| WO | 2017197377 | 11/2017 |
| WO | 2017222935 | 12/2017 |
| WO | 2018009938 | 1/2018 |
| WO | 2018015818 | 1/2018 |
| WO | 2018042343 | 3/2018 |
| WO | 2018108627 | 6/2018 |
| WO | 2018122419 | 7/2018 |
| WO | 2018222598 | 12/2018 |
| WO | 2018234139 | 12/2018 |
| WO | 2019009412 | 1/2019 |
| WO | 2019068726 | 4/2019 |
| WO | 2019075386 | 4/2019 |
| WO | 2019086474 | 5/2019 |
| WO | 2019101551 | 5/2019 |
| WO | 2019104070 | 5/2019 |
| WO | 2019129121 | 7/2019 |
| WO | 2019129213 | 7/2019 |
| WO | 2019145726 | 8/2019 |
| WO | 2019166628 | 9/2019 |
| WO | 2019191504 | 10/2019 |
| WO | 2019201432 | 10/2019 |
| WO | 2019202052 | 10/2019 |
| WO | 2019204816 | 10/2019 |
| WO | 2019232245 | 12/2019 |
| WO | 2020014599 | 1/2020 |
| WO | 2022013684 | 1/2020 |
| WO | 2020027704 | 2/2020 |
| WO | 2020030143 | 2/2020 |
| WO | 2020037166 | 2/2020 |
| WO | 2020046991 | 3/2020 |
| WO | 2020109297 | 6/2020 |
| WO | 2020142748 | 7/2020 |
| WO | 2020169682 | 8/2020 |
| WO | 2020172093 | 8/2020 |
| WO | 2020192750 | 10/2020 |
| WO | 2020247665 | 12/2020 |
| WO | 2021176369 | 9/2021 |
| WO | 2021205290 | 10/2021 |
| WO | 2021205296 | 10/2021 |
| WO | 2021250648 | 12/2021 |
| WO | 2021252491 | 12/2021 |
| WO | 2021252644 | 12/2021 |
| WO | 2022020242 | 1/2022 |

OTHER PUBLICATIONS

Li, Jie Jack. Heterocyclic Chemistry in Drug Discovery. Hoboken, N.J: Wiley, 2013. Print. (Year: 2013).*

Boström J, Hogner A, Llinàs A, Wellner E, Plowright AT. Oxadiazoles in medicinal chemistry. J Med Chem. Mar. 8, 2012;55(5):1817-30. doi: 10.1021/jm2013248. Epub Jan. 13, 2012. PMID: 22185670. (Year: 2012).*

U.S. Pat. No. 11,952,365 with appended Priority Document (U.S. Appl. No. 63/144,113) (Year: 2021).*

Konno S, Thanigaimalai P, Yamamoto T, Nakada K, Kakiuchi R, Takayama K, Yamazaki Y, Yakushiji F, Akaji K, Kiso Y, Kawasaki Y, . Design and synthesis of new tripeptide-type SARS-CoV 3CL protease inhibitors containing an electrophilic arylketone moiety. Bioorg Med Chem. J Jan. 15, 2013;21(2):412-24 (Year: 2013).*

Abranyi-Balogh, Peter et al., "A road map for prioritizing warheads for cysteine targeting covalent inhibitors", European Journal of Medicinal Chemistry, 2018, pp. 94-107, vol. 160.

Adedej, Adeyemi O., et al., "Antiviral drugs specific for coronaviruses in preclinical development", Current Opinion Virology, Oct. 2014, pp. 45-53, vol. 8.

Albuquerque, Nadine De., et al., "Murine Hepatitis Virus Strain 1 Produces a Clinically Relevant Model of Severe Acute Respiratory Syndrome in A/J Mice", Journal of Virology, Nov. 2006, pp. 10382-10394, 80(21).

Amblard, Franck, et al., "Synthesis and antiviral evaluation of novel peptidomimetics as norovirus protease inhibitors", Bioorganic & Medicinal Chemistry Letters, 2018, pp. 2165-2170, vol. 28, Issue 12.

Bandyopadhyay, Anupam, et al., "Targeting biomolecules with reversible covalent chemistry", Current Opinion in Chemical Biology, 2016, pp. 110-116, vol. 34.

Bernassola, Francesca, et al., "HECT-Type E3 Ubiquitin Ligases in Cancer", Trends in Biochemical Sciences, Dec. 2019, pp. 1057-1075, 44(12).

Berteotti, Anna, et al., "Predicting the Reactivity of Nitrile-Carrying Compounds with Cysteine: A Combined Computational and Experimental Study", ACS Medicinal Chemistry Letters, Feb. 24, 2014, pp. 501-505, 5(5).

Boras, Brittton, et al., "Discovery of a Novel Inhibitor of Coronavirus 3CL Protease for the Potential Treatment of COVID-19", bioRxiv 2020, 09.12.293498; doi: https://doi.org/10.1101/2020.09.12.293498, pp. 1-67.

Cai, Jiaqiang, et al., "4-(3-Trifluoromethylpheny)-pyrimidine-2-carbonitrile as cathepsin S inhibitors: N3, not N1 is critically important", Bioorganic & Medicinal Chemistry Letters, Aug. 1, 2010, pp. 4507-4510, 20(15).

Casimiro-Garcia, Augstin, et al., "Identification of Cyanamide-Based Janus Kinase 3 (JAK3) Covalent Inhibitors", Journal of Medicinal Chemistry, 2018, pp. 10665-10699, 61(23).

(56) References Cited

OTHER PUBLICATIONS

Chatterjee, Payal, et al., "Can Relative Binding Free Energy Predict Selectivity of Reversible Covalent Inhibitors?", Journal of American Chemical Society, 2017, pp. 17945-17952, 139(49).
Clinical Trials: "Study of PF-07321332 In Health Participants", ClinicalTrials.gov Identifier: NCT04756531, last updated post: Jul. 2, 2021, 12 pages.
Chuck, C.P., et al., "Design, synthesis and cystallographic analysis of nitrile-based broad-sprectrum peptidomimetic inhibitors for coronavirus 3C-like protease", European Journal Medicinal Chemistry, 2013, pp. 1-6, vol. 59.
Coteron, Jose M., et al., "Falcipain Inhibitors: Optimization Studies of the 2-Pyrimidinecarbonitrile Lead Series", Journal of Medicinal Chemistry, 2010, pp. 6129-6152, 53(16).
Dai, Wenhao, et al., "Structure-based design of antiviral drug candidates targeting the SARS-CoV-2 main protease", Science, Jun. 19, 2020, pp. 1331-1335, 368( 6497).
Damalanka, Vishnu C., et al., "Structure-guided design, synthesis and evaluation of oxazolidinone-base inhibitors of norovirus 3CL protease", European Journal of Medicinal Chemistry, 2018, pp. 881-890, vol. 143.
De Cesco, Stephane, et al., "Covalent inhibitors and discovery", European Journal Medicinal Chemistry, Sep. 29, 2017, pp. 96-114, vol. 138.
Dong, Liying, et al., "Discovering drugs to treat coronavirus disease 2019 (COVID-19)," Drug Discoveries & Therapeutics, 2020, pp. 58-60, 14(1).
Dragovich, P.S., et al., "Structure-Based Design of Ketone-Containing, Tripeptidyl Human Rhinovirus 3C Protease Inhibitors", Bioorganic & Medicinal Chemistry Letters, 2000, pp. 45-48, 10(1).
Dragovich, P.S., et al., "Structure-Based Design, Synthesis, and Biological Evaluation of Irreversible Human Rhinovirus 3C Protease Inhibitors. 4. Incorporation of P1 Lactam Moieties as L-Glutamine Replacements", Journal of Medicinal Chemistry, 1999, pp. 1213-1224, 42(7).
Eaton, John K., et al., "Selective covalent targeting of GPX4 using masked nitrile-oxide electrophiles", Nature Chemical Biology, 2020, pp. 497-506, vol. 16.
Ehmke, Veronika, et al., "Tuning and predicting biological affinity: aryl nitriles as cysteine protease inhibitors", Organic Biomolecular Chemistry, 2012, pp. 5764-5768., vol. 10.
Fischer, Mark E., et al., "Inhibitors for Novel Coronavirus Protease Identified by Virtual Screening of 687 Million Compounds", Mar. 2020; pp. 1-21; Preprint, https://doi.org/10.26434/chemrxiv.11923239.v1.
Flanagan, et al., "Chemical and Computational Methods for the Characterization of Covalent Reactive Groups for the Prospective Design of Irreversible Inhibitors", Journal of Medicinal Chemistry, 2014, pp. 10072-10079, 57(23).
Fleming, Fraser F., et al., "Nitrile-Containing Pharmaceuticals: Efficacious Roles of the Nitrile Pharmacophore", Journal of Medicinal Chemistry, 2010, pp. 7902-7917, 53(22).
Gehringer, Matthias, et al., "Emerging and Re-Emerging Warheads for Targeted Covalent Inhibitors: Applications in Medicinal Chemistry and Chemical Biology", Journal of Medicinal Chemistry, Jun. 27, 2019, pp. 5673-5724, 62(12).
Halford, Bethany, To conquer COVID-19 create the perfect pill, Chemical & Engineering News, May 20, 2021, pp. 28-31, 99(19).
Hou, Yixuan J., et al., "SARS-CoV-2 Reverse Genetics Reveals a Variable Infection Gradient in the Respiratory Tract", Cell, Jul. 23, 2020, pp. 429-446.e14, 182(2).
International Patent Application No. PCT/IB2021/0157281, filed Aug. 6, 2021, International Search Report and Written Opinion, mailed Oct. 15, 2021, 16 pages.
Jeon, Sangeun, et al., "Identification of Antiviral Drug Candidates against SARS-CoV-2 from FDA-Approved Drugs", Antimicrobial Agents and Chemotherapy, Jul. 2020, pp. e00819-e00820, 64(7).
Johnson, Theodore O., et al., "Structure-Based Design of a Parallel Synthetic Array Directed Toward the Discovery of Irreversible Inhibitors of Human Rhinovirus 3C Protease", Journal of Medicinal Chemistry, May 9, 2002, pp. 2016-2023, 45(10).
Keyser, Samantha G., et al., "Computation-Guided Rational Design of a Peptide Motif That Reacts with Cyanobenzothiazoles via Internal Cysteine-Lysine Relay", Journal of Organic Chemistry, 2018, pp. 7467-7479, 83(14).
Kim, et al., "Reversal of the Progression of Fatal Coronavirus Infection in Cats by a Broad-Spectrum Coronavirus Protease Inhibitor", PLoS Pathoges, Mar. 30, 2016, pp. 1-18, e1005531, 12(3).
Kim, YunJeong, et al., "Broad-Spectrum Antivirals against 3C or 3C-Like Proteases of Picornaviruses, Noroviruses, and Coronaviruses", Journal of Virology, Nov. 2012, pp. 11754-11762, 86(21).
Kim, Yunjeong, et al., "Broad-Spectrum Inhibitors against 3C-Like Proteases of Feline Coronaviruses and Feline Caliciviruses", Journal of Virology, May 2015, pp. 4942-4950, 89(9).
Kitamura, Naoya, et al., "Expedited Approach toward the Rational Design or Noncovalent SARS-CoV-2 Main Protease Inhibitors", Journal of Medicinal Chemistry, 2021, Publication Date, Apr. 23, 2021; https://doi.org/10.1021/acs.jmedchem.1c00509.
Konno, Sho, et al., "Design and synthesis of new tripeptide-type SARS-CoV 3CL protease inhibitors containing an electrophilic arylketone, moiety", Bioorganic & Medicinal Chemistry, Jan. 15, 2013, pp. 412-424, 21(2).
Kruse, R.L., et al., "Therapeutic strategies in a outbreak scenario to treat the novel coronavirus originated in Wuhan, China", F1000Res. Jan. 31, 2020; pp. 1-14, 9:72.
Kuhn, Bernd, et al., "Prospective Evaluation of Free Energy Calculations for the Prioritization of Cathepsin L Inhibitors", Journal of Medicinal Chemistry, 2017, pp. 2485-2497, 60(6).
Lagoutte, Roman, et al., "Covalent inhibitors: an opportunity for rational target selectivity", Current Opinion Chemical Biology, Aug. 2017, pp. 54-63, vol. 39.
Laine, Dramane, et al., Discovery of Novel Cyanamide-Based Inhibitors of Cathepsin C, ACS Medicinal Chemistry Letters, 2011, pp. 142-147, 2(2).
Liu, Cynthia, et al., "Research and Development on Therapeutic Agents and Vaccines for COVID-19 and Related Human Coronavirus Diseases", ACS Central Science, 2020, pp. 315-331, 6(3).
Lonsdale, Richard, et al., "Structure-based design of targeted covalent inhibitors", Chemical Society Review, 2018, pp. 3816-3830, 47(11).
Ma, Chunlong, et al., "Boceprevir, GC-376, and calpain inhibitors II, XII inhibit SARS-CoV-2 viral replication by targeting the viral main protease", Cell Research, Aug. 2020, pp. 678-692, 30(8).
Macfaul, Philip A., et al., "A simple in vitro assay for assessing the reactivity of nitrile containing compounds", Bioorganic & Medicinal Chemistry Letters, 2009, pp. 1136-1138, 19(4).
Martin, James S., et al., "Characterising covalent warhead reactivity", Bioorganic & Medicinal Chemistry, May 15, 2019, pp. 2066-2074, 27(10).
Liu, Yuzhi, et al., "The development of Coronavirus 3C-Like protease (3CLpro) inhibitors from 2010-2020", European Journal of Medicinal Chemistry, 2020, pp. 1-18, vol. 206, 112711.
Jackel, Christain, and Koksch, Beater, "Fluorin in Peptide Design and Protein Engineering", European Journal of Organic Chemistry, Oct. 17, 2005; DOI: 10.1002/ejoc.200500205, pp. 4483-4503, 2005(21).
Kempf, Dale, et al., "Pharmacokinetic enhancement of the hepatitis C virus protease inhibitors VX-950 and SCH 503034 by co-dosing with ritonavir", Antiviral Chemistry and Chemotherapy, Jun. 2007, pp. 163-167, 18(3).
Everett, Jeremy, "Drug Discovery and Development: the Role of NMR", eMagRes, Jan. 26, 2012(2015); pp. 137-150, 4(1). Doi:10.1002/9780470034590.emrstm1389.
International Patent Application No. PCT/IB2021/056093, filed Jul. 7, 2021, Search Report and Written Opinion, mailed Sep. 20, 2021, 17 pages.
Konno, Sho, et al., "Design and synthesis of new tripeptide-type SARS-CoV 3CL protease inhibitors containing an electrophilic arylketone moiety", Bioorganic & Medicinal Chemistry, 2013, pp. 412-424, vol. 21.
Thanigaimalai, P., et al., "Development of potent dipeptide-type SARS-CoV 3CL protease inhibitors with novel P3 scaffolds: Design,

(56) References Cited

OTHER PUBLICATIONS synthesis, biological evaluation, and docking studies", European Journal of Medicinal Chemistry, 2013, pp. 372-384, vol. 68.
Russian Patent application No. 202113257, filed Aug. 6, 2021, Search Report dated Jul. 15, 2022, 2 pages.
Singapore Patent application No. 11202112508R, filed Aug. 6, 2021, Examination and Search Report, dated Jun. 28, 2022, 8 pages.
Spain application No. EA032794, filed Jan. 23, 2015, published Jul. 31, 2019, equivalent to WO2015/110826 and US2015210655.
U.S. Appl. No. 63/012,039, filed Apr. 17, 2020, Pardes Biosciences, Inc.
U.S. Appl. No. 63/031,357, filed May 28, 2020, Pardes Biosciences, Inc.
U.S. Appl. No. 63/036,866, filed, Jun. 9, 2020, Pardes Biosciences, Inc.
U.S. Appl. No. 63/039,297, filed Jun. 15, 2020, Pardes Biosciences, Inc.
U.S. Appl. No. 63/067,669, filed Aug. 19, 2020, Pardes Biosciences, Inc.
U.S. Appl. No. 63/091,630, filed Oct. 14, 2020, Pardes Biosciences, Inc.
U.S. Appl. No. 63/129,018, filed Dec. 22, 2020, Pardes Biosciences, Inc.
U.S. Appl. No. 63/171,675, filed Apr. 7, 2021, Pardes Biosciences Inc.
U.S. Appl. No. 63/172,478, filed Apr. 8, 2021, Pardes Biosciences, Inc.
U.S. Appl. No. 63/173,146, filed Apr. 9, 2021, Pardes Biosciences Inc.
International Patent Application No. PCT/IB2021/05728, filed Aug. 6, 2021, Third Part Observation, dated January 3. 2023, 14 pages.
Anand, Kanchan, et al., Coronavirus Main Proteinase (3CLpro) Structure: Basis for Design of Anti-SARS Drugs, Science, Jun. 13, 2003, pp. 1763-1767, vol. 300.
Cannalire, Rolando, et al., "A Journey around the Medicinal Chemistry of Hepatitis C Virus Inhibitors Targeting NS4B: From Target to Preclinical Drug Candidates", Journal of Medicinal Chemistry, 2016, pp. 16-41, vol. 59.
Chuck, C.P., et al., "Supplementary Material: Design, synthesis and crystallographic analysis of nitrile-base broad-spectrum peptidomimetic inhibitors for coronavirus 3C-like proteases", European Journal Medicinal Chemistry, Jan. 2013, pp. 1-4, vol. 59.
Clinical Trials: "EPCI-HR: Study of Oral PF-07321332/Ritovavir Compared with Placebo in Nonhospitalized High Risk Adults With COVID-19" ClinicalTrials.gov Identifier: NCT04960202, 8 pages, First Posted: Jul. 13, 2021; Last Posted: Dec. 2, 2021.
Corman, Victor M., et al., Hosts and Sources of Endemic Human Coronaviruses, Advanced Virus Research, 2018, pp. 163-188, vol. 100.
Cvetkovic, Risto S., et al., "Lopinavir/Ritonavir: A Review of its Use in the Management of HIV Infection", Drugs, 2003, pp. 769-802, vol. 63.
Ghosh, Arun K., et al., "Recent Progress in the Development of HIV-1 Protease Inhibitors for the Treatment of HIV/AIDS", Journal of Medicinal Chemistry, 2016, pp. 5172-5208, vol. 59.
Halford, Dr. Bethany, Apr. 6, 2021 , "This is the new oral clinical candidate", snap shot, of Twitter account Dr. Bethany Halford@beth_halford, 2 pages.
Halford, Bethany, "Pfizer unveils its oral SARS-CoV-2 inhibitor. The antiviral candidate is the first orally administered compound to enter clinical trials that targets the virus's main protease", ACS Meeting News COVID-19, Apr. 7, 2021, vol. 99, issue 13, 2 pages.
Hoffman, Robert L., et al., Discovery of Ketone-Based Covalent Inhibitors of Coronavirus 3CL Proteases for the Potential Therapeutic Treatment of COVID-19, Journal of Medicinal Chemistry, 2020, pp. 12725-12747, vol. 63(21).
Mckeage, Kate, et al., "Darunavir: A Review of its Use in the Management of HIV Infection in Adults", Drugs, 2009, pp. 477-503, vol. 69.
Moon, Joseph B., et al., "Reversible Covalent Inhibition of Papain by a Peptide Nitrile. Carbon-13 NMR Evidence for a Thioimidate Ester Adduct", Journal of American Chemical Society, (1986)2002, pp. 1350-1351, vol. 108.
Owen, Dafydd, "Oral Inhibitors of the SARS-CoV-2 Main Protease for the Treatment of COVID-19", Presentation from American Chemical Society Spring Meeting, Apr. 6, 2021, 18 pages.
Pfizer Inc., Press Release, Mar. 23, 2021; "Pfizer Initiates Phase 1 Study of Novel Oral Antiviral Therapeutic Agent Against SARS-COV-2", 4 pages.
Pfizer Inc., Press Release, Sep. 1, 2021, "First Participant Dosed in Phase 2/3 Study of Oral Antiviral Candidate in Non-Hopitalized Adults with COVID-19 Who Are at Low Risk of Severe Illness", 2 pages.
Reddy, M.B., et al., "Pharmacokinetic/Pharmacodynamic Predictors of Clinical Potency for Hepatitis C Virus Nonucleoside Polymerase and Protease Inhibitors", Antimicrobial. Agents Chemotherapy, Jun. 2012, pp. 3144-3156, 56(6).
Thanigaimalai, P., et al., "Development of Potent Dipeptide-type SARS-CoV 3CL Protease Inhibitors with Novel P3 Scaffolds: Design, Synthesis, biological Evaluation, and Docking Studies", European Journal Medicinal Chemistry , 2013, pp. 372-384, vol. 68.
Wu, Fan, et al., "A new coronavirus associated with human respiratory disease in China", Nature, Mar. 2020, pp. 265-269, vol. 579.
Zhang, Linlin, et al., "Crystal Structure of SARS-CoV-2 Main Protease Provides a Basis for Design of Improved αKetoamide Inhibitors", Science, 2020, pp. 409-412, vol. 368.
Zhang, Linlin, et al., "α-Ketoamides as Broad-Spectrum Inhibitors of Coronavirus and Enterovirus Replication: Structure-Baed Design, Synthesis, and Activity Assessment", Journal of Medicinal Chemistry, 2020, pp. 4562-4578, vol. 63.
Zhou, Peng, et al., "A pneumonia outbreak associated with a new coronavirus of probable bat origin", Nature, Feb. 2020, pp. 270-273, vol. 579.
Montagutelli, Xavier, et al., "The B1.351 and P.1 variants extend SARS-CoV-2 host range to mice", bioRxiv 2021.03.18.436013., doi: http://doi.org/10.1101/2021.03.18.436013, pp. 1-16.
Mott, Bryan T., et al., Identification and Optimization of Inhibitors of Trypanosomal Cysteine Proteases: Cruzain Rhodesain, and TbCatB, Journal of Medicinal Chemistry, Jan. 14, 2020, pp. 52-60, 53(1).
Namoto, Kenji, et al., "Structure-based design and synthesis of macrocyclic human rhinovirus 3C protease Inhibitors", Bioorganic & Medicinal Chemistry Letters, Mar. 1, 2018, pp. 906-909, 28(5).
Oballa, Renata M., et al., "A generally applicable method for assessing the electrophilicity and reactivity of diverse nitrile-containing compounds", Bioorganic & Medicinal Chemistry Letters, 2007, pp. 998-1002, 17(4).
Paasche, Alexander, et al., Mechanistic Insights into SARS Coronavirus Main Protease by Computational Chemistry Methods:, 2021, n. pag. Print. Doctoral Thesis,pp. 1-183, University of Würzburg. Germany. https://d-nb.info/1037687825/34.
Patick, A.K., et al., "Protease Inhibitors as Antiviral Agents", Clinical Microbiol Reviews, Oct. 1998, pp. 614-627, 11(4).
Pillaiyar, Thanigaimalai, et al., "An Overview of Severe Acute Respiratory Syndrome-Coronavirus (SAR-CoV) 3CL Protease Inhibitors: Peptidomimetics and Small Molecule Chemotherapy", Journal of Medicinal Chemistry, 2016, pp. 6595-6628, 59(14).
Press Release: "Pfizer Initiates Phase 1 Study of Novel Oral Antiviral Therapeutic Agent Against SARS-Cov-2"; Mar. 23, 2021, https://ww.businesswire.com/new/home/2021023005644/en/.
Prior, Allan M., et al., "Design, synthesis, and bioevaluation of viral 3C and 3C-like protease inhibitors", Bioorganic & Medicinal Chemistry Letters, 2013, pp. 6317-6320, 23(23).
Rathnayake, Athri D., et al., "3C-like protease inhibitors block coronavirus replication in vitro and improve survival in MERS-CoV-infected mice", Science Translational Medicine, Aug. 19, 2020,pp. 1-11, eabc5332, 12(557).
Ray, Sneha, et al., "New Electrophilies and Strategies for Mechanism-Based and Targeted Covalent Inhibitor Design", Biochemistry, 2019, pp. 5234-5244, 58(52).

(56) References Cited

OTHER PUBLICATIONS

Santos, Alberto Monteiro Dos, et al., "Experimental study and computational modelling of cruzain cysteine protease inhibition by dipeptidyl nitriles", Physical Chemistry Chemical Physics, 2018, pp. 24317-24328, vol. 20.
Santos, Maria M., et al., "Michael Acceptors as Cysteine Protease Inhibitors", Mini Reviews Medicinal Chemistry, Oct. 2007, pp. 1040-1050, 7(10).
Schade, Markus, et al., "Highly Selective Sub-Nanomolar Cathepsin S Inhibitors by Merging Fragment Binders with Nitrile Inhibitors", Journal of Medicinal Chemistry, 2020, pp. 11801-11808, 63(20).
Schnute, Mark E., et al., "Aminopyrazole Carboxamide Bruton's Tyrosine Kinase Inhibitors. Irreversible to Reversible Covalent Reactive Group Tuning", ACS Medicinal Chemistry Letters, 2019, pp. 80-85, 10(1).
Serafimova, Iana M., et al., Reversible targeting of noncatalytic cysteines with chemically tuned electrophiles. 2013, pp. 1-174 UCSF ProQuest ID: Serafimova_ucsf_0034D_10695.REDACTED. Merritt ID: ark:/13030/m5x36bhx. Retrieved from https://escholarship.org/uc/item/0cj6m628.
Silva, Daniel G., et al., A comparative study of warheads for design of cysteine protease inhibitors, Bioorganic & Medicinal Chemistry Letters, Nov. 15, 2017, pp. 5031-5035, 27(22).
Sinha, Sarmistha, et al., "Electrophilicity of Pyridazine-3-carbonitrile, Pyrimidine-2-carbonitrile, and Pyridine-carbonitrile Derivatives: A Chemical Model to Describe the Formation of Thiazoline Derivatives in Human Liver Microsomes", Chemical Research in Toxicology, Dec. 15, 2014, pp. 2052-2061, 27(12).
Steuten, Kas, et al., "Challenges for Targeting SARS-CoV-2 Proteases as a Therapeutic Strategy for COVID-19", ACS Infectious Diseases, 2021, Publication date Feb. 11, 2021, pp. 1457-1468, 7(6). https://doi.org/10.1021/acsinfecdis.0c00815.
STN Registry Database Entry for 1831065-26-9 entered STN Dec. 16, 2015.
STN Registry Database Entry for 2248095-92-1 entered STN Nov. 13, 2018.
Tomar, et al., "Understanding the determinants for substrate recognition, regulation of enzymatic activity and the development of broad-spectrum inhibitors of coronavirus 3-chymotrypsin-like proteases", 2015, Open Access Dissertations. 1332. https;//docs.lib.purdue.edu/open_access_dessertations/1322.
Totura, Allison L., et al., "Broad-spectrum coronavirus antiviral drug discovery", Expert Opinion on Drug Discovery, Apr. 2019, pp. 397-412, 14(4).
U.S. Appl. No. 17/221,676, filed Apr. 2, 2021.
U.S. Appl. No. 17/932,151, filed Sep. 14, 2022, Pfizer Inc.
Venkatraman, S., "Discovery of boceprevir, a direct-acting NS3/4A protease inhibitor for treatment of chronic hepatitis C infections", Trends in Pharmacological Sciences, 2012, pp. 289-294, 33(5).
Venkatraman, S., et al., "Discovery of (1R,5S)-N-[3-Amino-1-(cyclobutylmethyl)-2,3-dioxopropyl]-3-[2(S)-[[[(1,1-dimethylethyl)amino]carbonyl]amino]-3,3-dimethyl-1-oxobutyl]-6,6-dimethyl-3-azabicyclo[3.1.0]hexan-2(S)-carboxamide (SCH 503034), a Selective, Potent, Orally Bioavailable Hepatitis C Virus NS3 Protease Inhibitor: A Potential Therapeutic Agent for the Treatment of Hepatitis C Infection", Journal of Medicinal Chemistry, 2006, pp. 6074-6086, 49(20).
Venkatraman, S., et al., "Potent inhibitors of HCV-NS3 protease derived from boronic acids", Bioorganic & Medicinal Chemistry Letters, 2009, pp. 180-183, 19(1).
Vuong, Wayne, et al., "Feline coronavirus drug inhibits the main protease of SARS-CoV-2 and blocks virus replications", Nature Communications, Aug. 27, 2020, pp. 1-11, 4282, 11(1).
Wang, Luhong, et al., "Covalent binding design strategy: A prospective method for discovery of potent targeted anticancer agents", European Journal of Medicinal Chemistry, 2017, pp. 493-505, vol. 142.
Wang, Yaxin, et al., "Inhibition of enterovirus 71 replication by an α-hydroxy-nitrile derivative NK-1.9K", Antiviral Research, Jan. 5, 2017, pp. 91-100, vol. 141.
White, Kris M., et al., "Plitidepsin has potent preclinical efficacy against SARS-CoV-2 by targeting the host protein eEF1A", Science, Feb. 26, 2021, pp. 926-931, 371(6532).
WIPO Patent Landscape Reports Project on Ritonavir, Oct. 2011, pp. 1-105.
Ye, Gang, et al., "Structural Basis for Inhibiting Porcine Epidemic Diarrhea Virus Replication with the 3C-Like Protease Inhibitor GC376", Viruses, Feb. 21, 2020, pp. 240, 12(2).
Zaidman, et al., "An automatic pipeline for the design of irreversible derivatives identifies a potent SARS-CoV-2 Mpro inhibitors", bioRxiv 2020.09.21.299776.
Zhai, et al., "Cyanohydrin as an Anchoring Group for Potent and Selective Inhibitors of Enterovirus 71 3C Protease", Journal of Medicinal Chemistry, 2015, pp. 9414-9420, 58(23).
Zhao, Zheng, et al., "Progress with covalent small-molecule kinase inhibitors", Drug Discovery Today, 2018, pp. 727-735, 23(3), ISSN 1359-6446.
STN Registry Database Entry for 2628280-0-8 entered STN Apr. 7, 2021.
U.S. Appl. No. 63/054,048, filed Jul. 20, 2020, Enanta Pharmaceuticals, Inc., 87 pages.
Anson, B. J., et al., "Broad-spectrum inhibition of coronavirus main and papain-like proteases by HCV drugs", Research Square, May 1, 2020, pp. 1-26; DOI: 10.21203/rs.3rs-26344/v1.
Bafna, et al., "Structural Similarity of SARS-CoV2 Mpro and 1 HCV NS3/4A Proteases 2 Suggests New Approaches for Identifying Existing Drugs Useful 3 as COVID-19 Therapeutics", ChemRxiv, Apr. 21, 2020, pp. 1-38.; DOI: 10.26434/chemrxiv.12156315.
Baker, Jeremy D., et al., "A drug repurposing screen identifies hepatitis C antivirals as inhibitors of the SARS-CoV-2 main protease", bioRxiv, Jul. 10, 2020; DOI: 10.1101/2020.07.10.197889; 3 pages.
Dolomanov, Oleg .V., et al., "OLEX2: a complete structure solution, refinement and analysis program", Applied Crystallography, 2009, pp. 339-341, 42(2).
Fehr, Anthony, et al. "Coronaviruses: An Overview of Their Replication and Pathogenesis", Methods in Molecular Biology., 2015, pp. 1-23, vol. 1282.
Finnin, Barrie C., "Transdermal Penetration Enhancers: Applications, Limitations, and Potential," Journal Pharmaceutical Science, 1999, pp. 955-958, 88(10).
Flack, H.D., "On Enantiomorph-Polarity Estimation", Acta Crystallographica Section A., 1983, pp. 876-881, A39(6).
Fleisher, David, et al., "Improved oral drug delivery: solubility limitations overcome by the use of prodrugs", Advanced Drug Delivery Reviews, 1996, pp. 115-130, 19(2).
Grum-Tokars, Valerie., et al., "Evaluating the 3C-like protease activity of SARS-Coronavirus: Recommendations for standardized assays for drug discovery", Virus Research, 2008, pp. 63-73, 133(1).
Haleblian, John K., "Characterization of Habits and Crystalline Modification of Solids and Their Pharmaceutical Applications", Journal of Pharmaceutical Science, Aug. 1975, pp. 1269-1288, 64(8).
Hegyi, Annette, et al., "Conservation of substrate specificities among coronavirus main proteases" Journal of General Virology, 2002, pp. 595-599, 83(3).
Hooft, Rob W.W., et al., "Determination of absolute structure using Bayesian statistics on Bijvoet differences", Journal of Applied Crystallography, 2008, pp. 96-103, vol. 41.
Lu, Jian J., et al., "On the origin and continuing evolution of SARS-CoV-2", National Science Review, 2020, pp. 1012-1023, 7(6).
Lu, Roujian, et al., "Genomic Characterisation and epidemiology of 2019 novel coronavirus: implications for virus origins and receptor binding" The Lancet, 2020 pp. 565-574, 395(10224).
Macrae, Clare F., et al., "Mercury: visualization and analysis of crystal structures", Journal of Applied Crystallography, 2006, pp. 453-457, 39(3).
Nasoff, Marc S., et al., "Identification of an immunodominant epitope within the capsid protein of hepatitis C virus", PNAS, 1991, pp. 5462-5466, 88(12).
Robinson, Ralph P., et al., "Discovery of the Hemifumarate and (α-L-Alanyloxy)methyl Ether as Prodrugs of an Antirheumatic

(56) References Cited

OTHER PUBLICATIONS

Oxindole: Prodrugs for the Enolic OH Group", Journal Medicinal Chemistry, 1996, pp. 10-18, 39(1).
Shuman, Robert T., et al., "An Improved Synthesis of Homoproline and Derivatives", Journal Organic Chemistry, 1990, pp. 738-741, 55(2).
Spek, A.L., "Single-Crystal structure validation with the program PLATON", Applied Crystallography, 2003, pp. 7-13, vol. 36.
Wan, Yushan, et al., "Receptor Recognition by the Novel Coronavirus from Wuhan: an Analysis Based on Decade-Long Structural Studies of SARS Coronavirus", Journal of Virology, 2020, pp. 1-12, 94(7).
Wang, Pin, et al., "Incorporation of Trifluoroisoleucine into Proteins in Vivo", Journal of American Chemical Society, 2003, pp. 6900-6906, vol. 125.
Werth, Jacob, et al., "Cobalt-Catalyzed Reductive Dimethylcyclopropanation of 1,3-Dienes", Angewandte Chemie International, 2018, pp. 13902-13906, 57(42).
Xu, Jiabao., et al., "Systematic Comparison of Two Animal-to-Human Transmitted Human Coronaviruses: SARS-CoV2 and SARS-CoV", Viruses, 2020, pp. 244-261, (17 pages), 12(2).
Yu, Mei-Ying W., et al., "Detection and Quantitation of HCV-RNA in Immune Globulins Produced by Cohn-Oncley Fractionation of Human Plasma, Viral Hepatitis and Liver Disease", Springer-Verlag, 1994, pp. 574-577.
Zhang, Lin L., et al., "X-ray Structure of Main Protease of the Novel Coronavirus SARS-CoV-2 Enables Design of α-Ketoamide Inhibitors", 2020, Bio Rxiv, 14 pages.
Ziebuhr, John, et al., "Virus-encoded proteinases and proteolytic processing in the Nidovirales", Journal General Virology, 2000, pp. 853-879, 81(4).
Fan, K., "The substract specificity of SARS coronavirous 3C-like proteinase", Biochemical and Biophysical Research Communication, 2005, pp. 934-940, 329(3).
International Patent Application No. PCT/IB2021/0157281, filed Aug. 6, 2021, International Preliminary Report on Patentability, Dated Mary 7, 2023, 7 pages.
Njoroge, F.G., "Challenges in Modern Drug: A Case Study of Boceprevir, on HCV Protease Inhibitor for the Treatment of Hepatitis C. Virus Infection", Accounts of Chemical Research, 2008, pp. 50-59, 41(1).
Owen, Dafydd, "An oral SARS-CoV-2MPro inhibitor clinical candidate for the treatment of COVID-19", Science, Dec. 24, 2021, pp. 1586-1593, 374(6575).
Vandyck, K., et al., "Considerations for the Discouvery and Development of 3-Chymotrypsin-Like Cysteind Protease Inhibitors Targeting SARS-CoV-2 Infection", Current Opinion in Virology, 2021, pp. 36-40, vol. 49.
Zhang, X., et al., "Exploring the binding mechanism o fthe main proteinase in SARS-associated coronavirus and its implication to anti-SARS drug design", Bioorganic & Medicinal Chemistry, 2004, pp. 2219-2223, 12(9).

* cited by examiner

ANTIVIRAL HETEROARYL KETONE DERIVATIVES

This application is a national stage application under 35 U.S.C. 371 of PCT//IB2021/056093, filed on Jul. 7, 2021, which claims the benefit of U.S. Provisional Patent Application No. 63/050,766, filed on Jul. 11, 2020, the disclosures of which are hereby incorporated by reference in their entirety.

BACKGROUND OF THE INVENTION

The invention relates to compounds and methods of inhibiting viral replication activity comprising contacting a SARS-CoV-2-related 3C-like ("3CL") proteinase with a therapeutically effective amount of a SARS-CoV-2-related 3C-like protease inhibitor. The invention also relates to methods of treating Coronavirus Disease 2019 ("COVID-19") in a patient by administering a therapeutically effective amount of a SARS-CoV-2-related 3C-like protease inhibitor to a patient in need thereof. The invention further relates to methods of treating COVID-19 in a patient, the method comprising administering a pharmaceutical composition comprising a therapeutically effective amount of the SARS-CoV-2-related 3C-like protease inhibitor to a patient in need thereof.

A worldwide outbreak of Coronavirus Disease 2019 ("COVID-19") has been associated with exposures originating in late 2019 in Wuhan, Hubei Province, China. By mid-2020 the outbreak of COVID-19 has evolved into a global pandemic with millions of people having been confirmed as infected and resulting in hundreds of thousands of deaths. The causative agent for COVID-19 has been identified as a novel coronavirus which has been named Severe Acute Respiratory Syndrome Corona Virus 2 ("SARS-CoV-2"). The genome sequence of SARS-CoV-2 has been sequenced from isolates obtained from nine patients in Wuhan, China and has been found to be of the subgenus Sarbecovirus of the genus Betacoronavirus. Lu, R. et al. The Lancet, 395, 10224,565-574; online Jan. 29, 2020. The sequence of SARS-CoV-2 was found to have 88% homology with two bat-derived SARS-like coronaviruses, bat-SL-CoVZC45 and bat-SL-CoVZXC21 which were collected in 2018 in Zhoushan, eastern China. SARS-CoV-2 was also found to share about 79% homology with Severe Acute Respiratory Syndrome Corona Virus ("SARS-CoV"), the causative agent of the SARS outbreak in 2002-2003, and about 50% homology with Middle East Respiratory Syndrome Coronavirus ("MERS-CoV"), the causative agent of a respiratory viral outbreak originating in the Middle East in 2012. Based on a recent analysis of 103 sequenced genomes of SARS-CoV-2 it has been proposed that SARS-CoV-2 can be divided into two major types (L and S types) with the S type being ancestral and the L type having evolved from the S-type. Lu, J.; Cui, J. et al. On the origin and continuing evolution of SARS-CoV-2; http://doi.org/10.1093/nsr/nwaa036. The S and L types can be clearly defined by just two tightly linked SNPs at positions 8,782 (orf1ab:T8517C, synonymous) and 28,144 (ORF8: C251T, S84L). In the 103 genomes analyzed approximately 70% were of the L-type and approximately 30% were of the S-type. It is unclear if the evolution of the L-type from the S-type occurred in humans or through a zoonotic intermediate but it appears that the L-type is more aggressive than the S-type and human interference in attempting to contain the outbreak may have shifted the relative abundance of the L and S types soon after the SARS-CoV-2 outbreak began. The discovery of the proposed S- and L-subtypes of SARS-CoV-2 raises the possibility that an individual could potentially be infected sequentially with the individual subtypes or be infected with both subtypes at the same time. In view of this evolving threat there is an acute need in the art for an effective treatment for COVID-19 and for methods of inhibiting replication of the SARS-CoV-2 coronavirus.

Recent evidence clearly shows that the newly emerged coronavirus SARS-CoV-2, the causative agent of COVID-19 (Centers for Disease Control, CDC) has acquired the ability of human-to-human transmission leading to community spread of the virus. The sequence of the SARS-CoV-2 spike protein receptor-binding domain ("RBD"), including its receptor-binding motif (RBM) that directly contacts the angiotensin-converting enzyme 2 receptor, ACE2, is similar to the RBD and RBM of SARS-CoV, strongly suggesting that SARS-CoV-2 uses ACE2 as its receptor. Wan, Y.; Shang, J.; Graham, R.; Baric, R. S.; Li, F.; Receptor recognition by the novel coronavirus from Wuhan: An analysis based on decade-long structural studies of SARS coronavirus; J. Virol. 2020; doi:10.1128/JVI.00127-20. Several critical residues in SARS-CoV-2 RBM (particularly $Gln^{493}$) provide favorable interactions with human ACE2, consistent with SARS-CoV-2's capacity for human cell infection. Several other critical residues in SARS-CoV-2's RBM (particularly $Asn^{501}$) are compatible with, but not ideal for, binding human ACE2, suggesting that SARS-CoV-2 uses ACE2 binding in some capacity for human-to-human transmission.

Coronavirus replication and transcription function is encoded by the so-called "replicase" gene (Ziebuhr, J., Snijder, E. J., and Gorbalenya, A. E.; Virus-encoded proteinases and proteolytic processing in the *Nidovirales*. J. Gen. Virol. 2000, 81, 853-879; and Fehr, A. R.; Perlman, S.; Coronaviruses: An Overview of Their Replication and Pathogenesis, Methods Mol. Biol. 2015; 1282: 1-23. doi: 10.1007/978-1-4939-2438-7_1), which consists of two overlapping polyproteins that are extensively processed by viral proteases. The C-proximal region is processed at eleven conserved interdomain junctions by the coronavirus main or "3C-like" protease (Ziebuhr, Snijder, Gorbalenya, 2000 and Fehr, Perlman et al., 2015). The name "3C-like" protease derives from certain similarities between the coronavirus enzyme and the well-known picornavirus 3C proteases. These include substrate preferences, use of cysteine as an active site nucleophile in catalysis, and similarities in their putative overall polypeptide folds. The SARS-CoV-2 3CL protease sequence (Accession No. YP_009725301.1) has been found to share 96.08% homology when compared with the SARS-CoV 3CL protease (Accession No. YP_009725301.1) Xu, J.; Zhao, S.; Teng, T.; Abdalla, A. E.; Zhu, W.; Xie, L.; Wang, Y.; Guo, X.; Systematic Comparison of Two Animal-to-Human Transmitted Human Coronaviruses: SARS-CoV-2 and SARS-CoV; Viruses 2020, 12, 244; doi:10.3390/v12020244. Very recently, Hilgenfeld and colleagues published a high-resolution X-ray structure of the SARS-CoV-2 coronavirus main protease (3CL) Zhang, L.; Lin, D.; Sun, X.; Rox, K.; Hilgenfeld, R.; X-ray Structure of Main Protease of the Novel Coronavirus SARS-CoV-2 Enables Design of α-Ketoamide Inhibitors; bioRxiv preprint doi: https://doi.org/10.1101/2020.02.17.952879. The structure indicates that there are differences when comparing the 3CL proteases of SARS-CoV-2 and SARS-CoV. In the SARS-CoV but not in the SARS-CoV-2 3CL protease dimer, there is a polar interaction between the two domains III involving a 2.60-Å hydrogen bond between the side-chain hydroxyl groups of residue $Thr^{285}$ of each protomer, and supported by a hydrophobic contact between the side-chain of $Ile^{286}$ and $Thr^{285}$ $C\gamma_2$. In the SARS-CoV-2 3CL, the threonine is replaced by alanine, and the isoleucine by leucine when compared with the same residues in the SARS-CoV 3CL. The Thr285Ala replacement observed in the SARS-CoV-2 3CL protease allows the two domains III to approach each other somewhat closer (the distance between the Ca atoms of residues 285 in molecules A and B is 6.77 Å in SARS-CoV 3CL protease and 5.21 Å in SARS-CoV-2 3CL protease and the distance between the centers of mass of the two domains III shrinks from 33.4 Å to 32.1 Å). In the active site of SARS-CoV-2 3CL, $Cys^{145}$ and $His^{41}$ form a catalytic dyad which when taken together with a with a buried water molecule that is hydrogen-bonded to $His^{41}$ can be considered to constitute a catalytic triad of the SARS-CoV-2 3CL protease. In view of the ongoing SARS-CoV-2 spread which has caused the current world-wide COVID-19 outbreak, it is desirable to have new methods of inhibiting SARS-CoV-2 viral replication and of treating COVID-19 in patients.

SUMMARY OF THE INVENTION

The present invention provides, in part, novel compounds which act in inhibiting or preventing SARS-CoV-2 viral replication and thus are useful in the treatment of COVID-19. The present invention also provides, in part, pharmaceutical compositions comprising the compounds and methods of treating COVID-19 and inhibiting SARS-CoV-2 viral replication by administering the compounds of the invention or pharmaceutical compositions comprising the compounds of the invention. The present invention also provides, in part, methods for preparing such compounds. Particular embodiments of the present invention include those set forth below as E1 to E47.

A first embodiment of a first aspect of the present invention, designated as E1, is a compound of Formula I

I

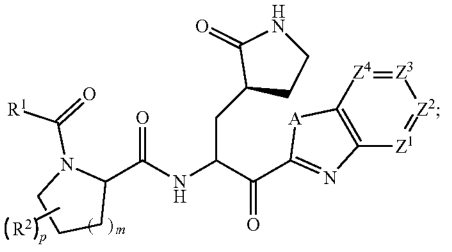

or a pharmaceutically acceptable salt thereof; wherein A is S or O; $Z^1$, $Z^2$, $Z^3$ and $Z^4$ are each independently $CR^3$ or N; $R^1$ is selected from the group consisting of $C_1$-$C_6$ alkyl, $R^{1b}$NH—$C_1$-$C_6$ alkyl-, $C_1$-$C_6$ alkoxy, ($C_1$-$C_6$ alkoxy)-$C_1$-$C_6$ alkyl, $C_2$-$C_6$ alkynyl, $C_3$-$C_6$ alkynyloxy, $C_3$-$C_{12}$ cycloalkyl optionally fused with a 5- to 6-membered heteroaryl or phenyl, ($C_3$-$C_{12}$ cycloalkyl)-$C_1$-$C_6$ alkyl, $C_3$-$C_{12}$ cycloalkoxy, ($C_3$-$C_{12}$ cycloalkoxy)-$C_1$-$C_6$ alkyl, 4- to 12-membered heterocycloalkyl which is optionally fused with a 5- to 6-membered heteroaryl or phenyl and wherein said heterocycloalkyl comprises one to four heteroatoms independently selected from N, O and $S(O)_n$, (4- to 12-membered heterocycloalkyl)-$C_1$-$C_6$ alkyl wherein said heterocycloalkyl moiety comprises one to four heteroatoms independently selected from N, O and $S(O)_n$, $C_6$-$C_{10}$ aryl optionally fused with a $C_4$-$C_6$ cycloalkyl or a 4- to 7-membered heterocycloalkyl, ($C_6$-$C_{10}$ aryl)-$C_1$-$C_6$ alkyl, 5- to 10-membered heteroaryl comprising one to five heteroatoms independently selected from N, O and S, (5- to 10-membered heteroaryl)-$C_1$-$C_6$ alkyl wherein the heteroaryl moiety comprises one to five heteroatoms independently selected from N, O and S, (5- to 10-membered heteroaryloxy)-$C_1$-$C_6$ alkyl wherein the heteroaryl moiety comprises one to five heteroatoms independently selected from N, O and S, (5- to 6-membered heteroaryl)-(5- to 6-membered heteroaryl)- wherein each heteroaryl moiety comprises one to four heteroatoms independently selected from N, O and S, (4- to 7-membered heterocycloalkyl)-(5- to 6-membered heteroaryl)- wherein the heterocycloalkyl moiety comprises one to three heteroatoms independently selected from N, O and $S(O)_n$ and the heteroaryl moiety comprises one to four heteroatoms independently selected from N, O and S, (5- to 6-membered heteroaryl)-(4- to 7-membered heterocycloalkyl)- wherein the heterocycloalkyl moiety comprises one to three heteroatoms independently selected from N, O and $S(O)_n$ and the heteroaryl moiety comprises one to four heteroatoms independently selected from N, O and S, wherein each $R^1$ group is optionally substituted with one to five $R^{1a}$; $R^{1a}$ at each occurrence is independently selected from the group consisting of oxo, halo, hydroxy, cyano, phenyl, amino, ($C_1$-$C_3$ alkyl)amino, di($C_1$-$C_3$ alkyl)amino, $C_1$-$C_6$ alkyl optionally substituted with one to five fluoro, $C_1$-$C_6$ alkoxy optionally substituted with one to five fluoro, ($C_1$-$C_3$ alkoxy)-$C_1$-$C_3$ alkyl optionally substituted with one to five fluoro, $C_3$-$C_6$ cycloalkyl optionally substituted with one to three substituents independently selected from fluoro and $C_1$-$C_3$ alkyl, $C_3$-$C_6$ cycloalkyl-$C_1$-$C_6$ alkyl, phenyl, phenyl-$C_1$-$C_6$ alkyl, ($C_1$-$C_6$ alkyl)-C(O)— and ($C_1$-$C_6$ alkyl)-$S(O)_n$—; $R^{1b}$ is selected from the group consisting of $C_1$-$C_6$ alkyl-C(O)—, $C_3$-$C_6$ cycloalkyl-C(O)—, $C_1$-$C_6$ alkyl-OC(O)—, $C_3$-$C_6$ cycloalkyl-OC(O)—, ($C_1$-$C_6$ alkyl)$_2$N—C(O)—, ($C_1$-$C_6$ alkyl)$_2$N—($C_1$-$C_6$ alkyl)-C(O)—, ($C_1$-$C_6$ alkyl)-$S(O)_2$—, ($C_3$-$C_6$ cycloalkyl)-$S(O)_2$—, (4- to 7-membered heterocycloalkyl)-OC(O)— wherein the heterocycloalkyl moiety comprises one to three heteroatoms independently selected from N, O and $S(O)_n$, 5- to 6-membered heteroaryl comprising one to three heteroatoms independently selected from N, O and S; wherein each $R^{1b}$ group is optionally substituted with one to five fluoro or with one to two $C_1$-$C_3$ alkyl; $R^2$ at each occurrence is independently selected from the group consisting of fluoro, $C_1$-$C_6$ alkyl optionally substituted with one to three fluoro, and $C_1$-$C_6$ alkoxy optionally substituted with one to three fluoro; or two $R^2$ groups when attached to adjacent carbons and taken together with the carbons to which they are attached are a fused $C_3$-$C_6$ cycloalkyl which is optionally substituted with one to four $R^{2a}$; or two $R^2$ groups when attached to the same carbon and taken together with the carbon to which they are attached are a spiro $C_3$-$C_6$ cycloalkyl which is optionally substituted with one to four $R^{2a}$; $R^{2a}$ at each occurrence is independently selected from fluoro, $C_1$-$C_3$ alkyl optionally substituted with one to five fluoro and $C_1$-$C_3$ alkoxy optionally substituted with one to five fluoro; $R^3$ at each occurrence is independently selected from hydrogen, halo, cyano, $C_1$-$C_6$ alkyl optionally substituted with one to five fluoro, $C_1$-$C_6$ alkoxy optionally substituted with one to five fluoro, and ($C_1$-$C_6$ alkyl)-$SO_2$—; m is 1 or 2; n at each occurrence is independently selected from 0, 1 and 2; and p is 0, 1, 2, 3 or 4.

E2. A compound of embodiment E1 wherein m is 1; or a pharmaceutically acceptable salt thereof.

E3 A compound of embodiment E1 wherein m is 2; or a pharmaceutically acceptable salt thereof.

E4 A compound of any one of embodiments E1 to E3 wherein $R^2$ at each occurrence is independently selected from the group consisting of fluoro, methyl, ethyl, isopropyl, tert-butyl, trifluoromethyl and tert-butoxy; or two $R^2$ groups when attached to adjacent carbons and taken together with the carbons to which they are attached are a fused cyclohexane, cyclopentane or cyclopropane ring which is optionally substituted with one to four $R^{2a}$; or two $R^2$ groups when attached to the same carbon and taken together with the carbon to which they are attached are a spirocyclopropane, spirocyclobutane, spirocyclopentane or spirocyclohexane ring which is optionally substituted with one to four $R^{2a}$; or a pharmaceutically acceptable salt thereof.

E5 A compound of any one of embodiments E1 to E4 wherein $R^{2a}$ at each occurrence is independently selected from the group consisting of fluoro, methyl, trifluoromethyl and methoxy; or a pharmaceutically acceptable salt thereof.

E6 A compound of E1 wherein m is 1 and the moiety

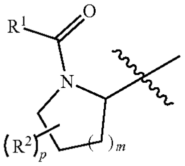

is selected from the group consisting of

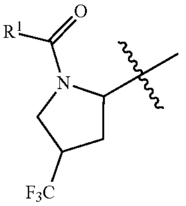,

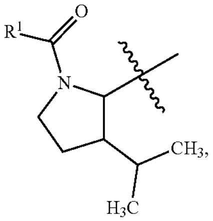

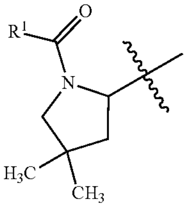,

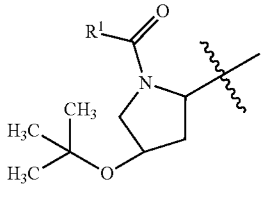,

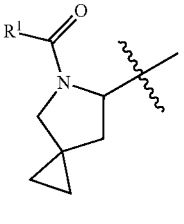,

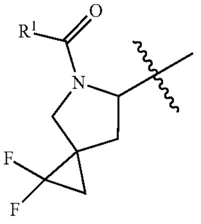,

-continued

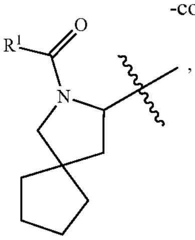,

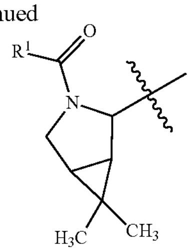,

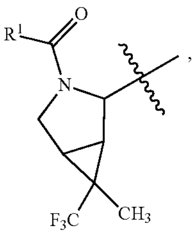,

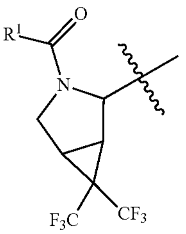,

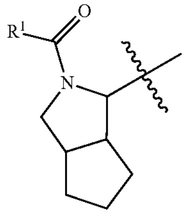, and

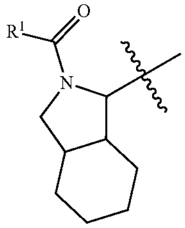;

or a pharmaceutically acceptable salt thereof.

E7 A compound of embodiment E1 wherein m is 2 and the moiety is selected from the group consisting of

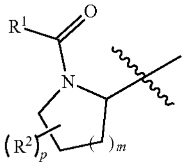

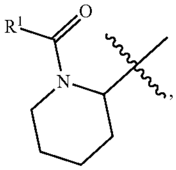,

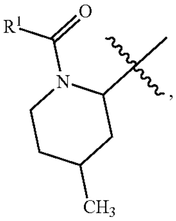,

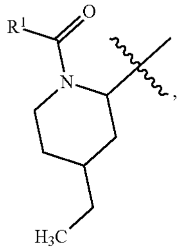,

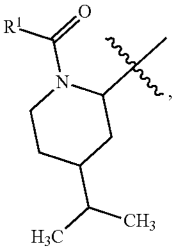, and

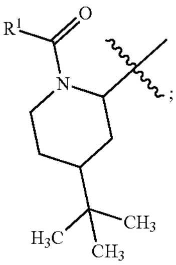;

or a pharmaceutically acceptable salt thereof.

E8 A compound of any one of embodiments E1 to E7 wherein the moiety

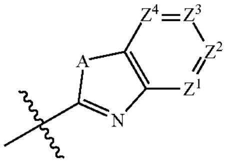

is selected from the group consisting of

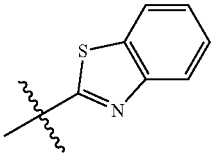

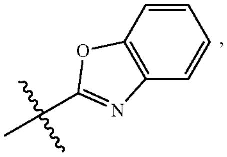

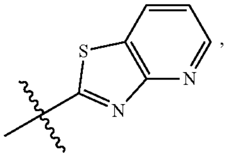

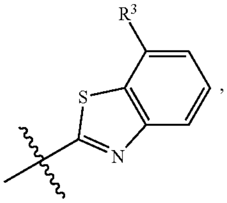

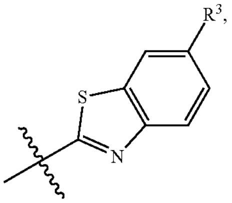

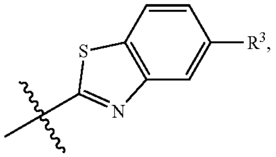

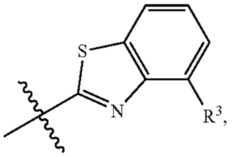

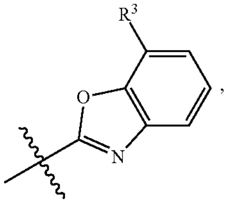

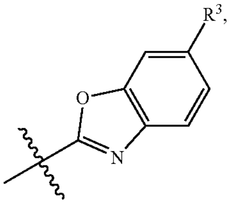

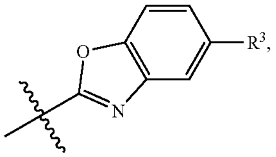

-continued

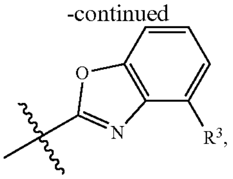

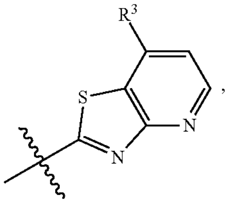

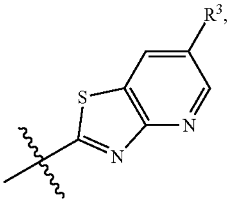

and

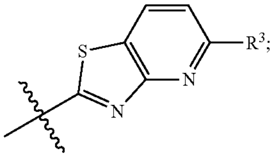

$R^3$ is selected from the group consisting of halo, cyano, $C_1$-$C_6$ alkyl optionally substituted with one to five fluoro, $C_1$-$C_6$ alkoxy optionally substituted with one to five fluoro, and ($C_1$-$C_6$ alkyl)-$SO_2$—; or a pharmaceutically acceptable salt thereof.

E9 A compound of embodiment E8 wherein $R^3$ is selected from the group consisting of chloro, cyano, methyl, trifluoromethyl, tert-butyl, methoxy and methylsulfonyl; or a pharmaceutically acceptable salt thereof.

E10 A compound of any one of embodiments E1 to E9 wherein $R^1$ is a 4- to 12-membered heterocycloalkyl which is optionally fused with a 5- to 6-membered heteroaryl or phenyl and wherein said heterocycloalkyl comprises one to four heteroatoms independently selected from N, O and $S(O)_n$, or is a (4- to 12-membered heterocycloalkyl)-$C_1$-$C_6$ alkyl wherein said heterocycloalkyl moiety comprises one to four heteroatoms independently selected from N, O and $S(O)_n$; each of which is optionally substituted with one to five $R^{1a}$; or a pharmaceutically acceptable salt thereof.

E11 A compound of embodiment E10 wherein the 4- to 12-membered heterocycloalkyl moiety in $R^1$ is selected from the group consisting of azetidinyl, pyrrolidinyl, piperidinyl, piperazinyl, morpholinyl, oxetanyl, tetrahydrofuranyl, pyranyl, 2-oxo-1,3-oxazolidinyl, oxabicyclo[2.2.1]heptyl, 1-oxa-8-azaspiro[4.5]decyl, 1,1-dioxido-1,2-thiazolidinyl and 1,1-dioxido-1,2-thiazinanyl; each of which is optionally substituted with one to three $R^{1a}$; or a pharmaceutically acceptable salt thereof.

E12 A compound of embodiment E11 wherein $R^1$ is a 4- to 12-membered heterocycloalkyl selected from

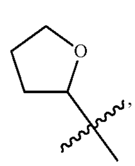, 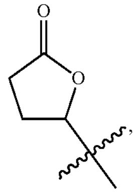, and 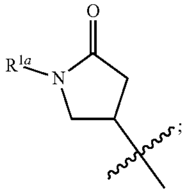;

or a pharmaceutically acceptable salt thereof.

E13 A compound of embodiment E12 wherein $R^{1a}$ is selected from the group consisting of methyl, isopropyl, tert-butyl, cyclobutyl, cyclopropylmethyl, phenyl and phenylmethyl; or a pharmaceutically acceptable salt thereof.

E14 A compound of any of embodiments E1 to E9 wherein $R^1$ is selected from the group consisting of phenyl, a 5- to 10-membered heteroaryl comprising one to five heteroatoms independently selected from N, O and S; a (5- to 10-membered heteroaryl)-$C_1$-$C_6$ alkyl wherein the heteroaryl moiety comprises one to five heteroatoms independently selected from N, O and S; and a (5- to 10-membered heteroaryloxy)-$C_1$-$C_6$ alkyl wherein the heteroaryl moiety comprises one to five heteroatoms independently selected from N, O and S; each of which is optionally substituted with one to five $R^{1a}$; or a pharmaceutically acceptable salt thereof.

E15 A compound of embodiment E14 wherein the 5- to 10-membered heteroaryl moiety in $R^1$ is selected from the group consisting of imidazolyl, pyrazolyl, oxazolyl, isoxazolyl, thiazolyl, isothiazolyl, oxadiazolyl, triazolyl, pyridinyl, pyrimidinyl, pyrazinyl, pyridazinyl, indolyl, quinolinyl, quinoxalinyl, benzotriazolyl, imidazo[1,2-a]pyridinyl, imidazo[2,1-b][1,3]thiazolyl, [1,2,4]triazolo[1,5-a]pyrimidinyl, [1,2,3]triazolo[1,5-a]pyridinyl and naphthyridinyl; each of which is optionally substituted with one to three $R^{1a}$; or a pharmaceutically acceptable salt thereof.

E16 A compound of embodiment E15 wherein $R^1$ is selected from the group consisting of indolyl, isoxazolyl, thiazolyl, thiazolylmethyl, pyrazolyl, pyrazolylmethyl, triazolyl and triazolylmethyl; each of which is optionally substituted with one to three $R^{1a}$; or a pharmaceutically acceptable salt thereof.

E17 A compound of embodiment E1 wherein $R^1$ is $C_2$-$C_6$ alkynyl or $C_3$-$C_6$ alkynyloxy; or a pharmaceutically acceptable salt thereof.

E18 A compound of embodiment E17 wherein $R^1$ is selected from the group consisting of but-3-yn-1-yl, pent-4-yn-1-yl and prop-2-yn-1-yloxy; or a pharmaceutically acceptable salt thereof.

E19 A compound of embodiment E1 wherein $R^1$ is $C_1$-$C_6$ alkoxy; or a pharmaceutically acceptable salt thereof.

E20 A compound of embodiment E19 wherein $R^1$ is selected from the group consisting of methoxy, ethoxy, prop-2-oxy and tert-butoxy; or a pharmaceutically acceptable salt thereof.

E21 A compound of embodiment E1 wherein $R^1$ is selected from the group consisting of $C_3$-$C_{12}$ cycloalkyl optionally fused with a 5- to 6-membered heteroaryl or phenyl, ($C_3$-$C_{12}$ cycloalkyl)-$C_1$-$C_6$ alkyl, $C_3$-$C_{12}$ cycloalkoxy and ($C_3$-$C_{12}$ cycloalkoxy)-$C_1$—$C_6$ alkyl; each of which is optionally substituted with one to three $R^{1a}$; or a pharmaceutically acceptable salt thereof.

E22 A compound of embodiment E21 wherein $R^1$ is cyclohexyl or 1-(cyclohexyloxy)ethyl; or a pharmaceutically acceptable salt thereof.

E23 A compound of any one of embodiments E1 to E9 wherein $R^1$ is $R^{1b}$NH—$C_1$-$C_6$ alkyl-; or a pharmaceutically acceptable salt thereof.

E24 A compound of embodiment E23 wherein $R^{1b}$NH—$C_1$-$C_6$ alkyl- is selected from

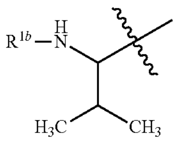 and 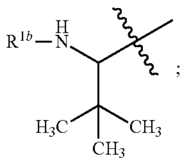;

or a pharmaceutically acceptable salt thereof.

E25 A compound of embodiment E24 wherein $R^{1b}$ is selected from the group consisting of $CH_3C(O)$—, $CF_3C(O)$—, $CH_3CH_2C(O)$—, $(CH_3)_2CHC(O)$—, $(CH_3)_3CC(O)$—, cyclopropyl-C(O)—, (3,3-difluorocyclobutyl)-C(O)—, $(CH_3)_2N$—C(O)—, $(CH_3)_2N$—$CH_2C(O)$—, $CH_3OC(O)$—, $CH_3CH_2OC(O)$—, $(CH_3)_2CHOC(O)$—, $(CH_3)_3COC(O)$—, (1-methylazetidin-3-yl)-OC(O)—, $CH_3S(O)_2$—, $CH_3CH_2S(O)_2$—, $(CH_3)_2CHS(O)_2$—, $(CH_3)_3CS(O)_2$— and (cyclopropyl)-$S(O)_2$—; or a pharmaceutically acceptable salt thereof.

E26 A compound of embodiment E25 wherein $R^{1b}$ is $CF_3C(O)$—; or a pharmaceutically acceptable salt thereof.

E27 A compound of embodiment E1 selected from the group consisting of (6S)—N-{(2R)-1-(1,3-benzothiazol-2-yl)-1-oxo-3-[(3S)-2-oxopyrrolidin-3-yl]propan-2-yl}-5-[(2R)-tetrahydrofuran-2-ylcarbonyl]-5-azaspiro[2.4]heptane-6-carboxamide;

N-{(2S)-1-(1,3-benzothiazol-2-yl)-1-oxo-3-[(3S)-2-oxopyrrolidin-3-yl]propan-2-yl}-4,4-dimethyl-1-[(2R)-tetrahydrofuran-2-ylcarbonyl]-L-prolinamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[(2R)-tetrahydrofuran-2-ylcarbonyl]-3-azabicyclo[3.1.0]hexane-2-carboxamide;

tert-butyl (1R,2S,5S)-2-({(2S)-1-(1,3-benzothiazol-2-yl)-1-oxo-3-[(3S)-2-oxopyrrolidin-3-yl]propan-2-yl}carbamoyl)-6,6-dimethyl-3-azabicyclo[3.1.0]hexane-3-carboxylate;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-{[(2R)-5-oxotetrahydrofuran-2-yl]carbonyl}-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-{[(3R)-1-methyl-5-oxopyrrolidin-3-yl]carbonyl}-3-azabicyclo[3.1.0]hexane-2-carboxamide;

N-acetyl-L-valyl-N-{(2S)-1-(1,3-benzothiazol-2-yl)-1-oxo-3-[(3S)-2-oxopyrrolidin-3-yl]propan-2-yl}-4,4-dimethyl-L-prolinamide;

N-(methoxycarbonyl)-L-valyl-N-{(2S)-1-(1,3-benzothiazol-2-yl)-1-oxo-3-[(3S)-2-oxopyrrolidin-3-yl]propan-2-yl}-4,4-dimethyl-L-prolinamide;

(2S)—N-{(2S)-1-(1,3-benzothiazol-2-yl)-1-oxo-3-[(3S)-2-oxopyrrolidin-3-yl]propan-2-yl}-1-[N-(methylsulfonyl)-L-valyl]piperidine-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-{[(3R)-5-oxo-1-(propan-2-yl)pyrrolidin-3-yl]carbonyl}-3-azabicyclo[3.1.0]hexane-2-carboxamide;

(1R,2S,5S)-3-(N-acetyl-3-methyl-L-valyl)-N-{(2S)-1-(1,3-benzothiazol-2-yl)-1-oxo-3-[(3S)-2-oxopyrrolidin-3-yl]propan-2-yl}-6,6-dimethyl-3-azabicyclo[3.1.0]hexane-2-carboxamide;

N-(cyclopropylcarbonyl)-L-valyl-N-{(2S)-1-(1,3-benzothiazol-2-yl)-1-oxo-3-[(3S)-2-oxopyrrolidin-3-yl]propan-2-yl}-4,4-dimethyl-L-prolinamide;

(6S)—N-{(2S)-1-(1,3-benzothiazol-2-yl)-1-oxo-3-[(3S)-2-oxopyrrolidin-3-yl]propan-2-yl}-5-{(2S)-3-methyl-2-[(methylsulfonyl)amino]butanoyl}-5-azaspiro[2.4]heptane-6-carboxamide;

(1R,2S,5S)—N-{(2S)-1-(1,3-benzothiazol-2-yl)-1-oxo-3-[(3S)-2-oxopyrrolidin-3-yl]propan-2-yl}-3-{[(3R)-1-(cyclopropylmethyl)-5-oxopyrrolidin-3-yl]carbonyl}-6,6-dimethyl-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-{[(3R)-1-cyclobutyl-5-oxopyrrolidin-3-yl]carbonyl}-6,6-dimethyl-3-azabicyclo[3.1.0]hexane-2-carboxamide;

(2S,4R)—N-{(2S)-1-(1,3-benzothiazol-2-yl)-1-oxo-3-[(3S)-2-oxopyrrolidin-3-yl]propan-2-yl}-4-methyl-1-[N-(methylsulfonyl)-L-valyl]piperidine-2-carboxamide;

(2S,4S)—N-{(2S)-1-(1,3-benzothiazol-2-yl)-1-oxo-3-[(3S)-2-oxopyrrolidin-3-yl]propan-2-yl}-4-methyl-1-[N-(methylsulfonyl)-L-valyl]piperidine-2-carboxamide;

N-(methylsulfonyl)-L-valyl-N-{(2S)-1-(1,3-benzothiazol-2-yl)-1-oxo-3-[(3S)-2-oxopyrrolidin-3-yl]propan-2-yl}-4,4-dimethyl-L-prolinamide;

(2S,4R)—N-{(2S)-1-(1,3-benzoxazol-2-yl)-1-oxo-3-[(3S)-2-oxopyrrolidin-3-yl]propan-2-yl}-4-methyl-1-[N-(trifluoroacetyl)-L-valyl]piperidine-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-{[(3R)-1-tert-butyl-5-oxopyrrolidin-3-yl]carbonyl}-6,6-dimethyl-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-(3-methyl-N-propanoyl-L-valyl)-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[N-(methylsulfonyl)-L-valyl]-3-azabicyclo[3.1.0]hexane-2-carboxamide;

(1S,3aR,6aS)—N-{(2S)-1-(1,3-benzothiazol-2-yl)-1-oxo-3-[(3S)-2-oxopyrrolidin-3-yl]propan-2-yl}-2-{(2S)-3-methyl-2-[(methylsulfonyl)amino]butanoyl}octahydro cyclopenta[c]pyrrole-1-carboxamide;

(1R,2S,5S)—N-{(2S)-1-(1,3-benzoxazol-2-yl)-1-oxo-3-[(3S)-2-oxopyrrolidin-3-yl]propan-2-yl}-6,6-dimethyl-3-[N-(trifluoroacetyl)-L-valyl]-3-azabicyclo[3.1.0]hexane-2-carboxamide;

(2S,4S)—N-{(2S)-1-(1,3-benzothiazol-2-yl)-1-oxo-3-[(3S)-2-oxopyrrolidin-3-yl]propan-2-yl}-4-ethyl-1-[N-(methylsulfonyl)-L-valyl]piperidine-2-carboxamide;

(2S,4R)—N-{(2S)-1-(1,3-benzothiazol-2-yl)-1-oxo-3-[(3S)-2-oxopyrrolidin-3-yl]propan-2-yl}-4-ethyl-1-[N-(methylsulfonyl)-L-valyl]piperidine-2-carboxamide;

N-(methylsulfonyl)-L-valyl-(3R)—N-{(2S)-1-(1,3-benzothiazol-2-yl)-1-oxo-3-[(3S)-2-oxopyrrolidin-3-yl]propan-2-yl}-3-propan-2-yl-L-prolinamide;

(1R,2S,5S)—N-{(2S)-1-(1,3-benzothiazol-2-yl)-1-oxo-3-[(3S)-2-oxopyrrolidin-3-yl]propan-2-yl}-3-[N-(cyclopropylcarbonyl)-3-methyl-L-valyl]-6,6-dimethyl-3-azabicyclo[3.1.0]hexane-2-carboxamide;

(2S,4R)—N-{(2S)-1-(1,3-benzothiazol-2-yl)-1-oxo-3-[(3S)-2-oxopyrrolidin-3-yl]propan-2-yl}-4-methyl-1-[N-(trifluoroacetyl)-L-valyl]piperidine-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[3-methyl-N-(2-methylpropanoyl)-L-valyl]-3-azabicyclo[3.1.0]hexane-2-carboxamide;

(2S)—N-{(2S)-1-(1,3-benzothiazol-2-yl)-1-oxo-3-[(3S)-2-oxopyrrolidin-3-yl]propan-2-yl}-4-methyl-2-{7-[(methylsulfonyl)amino]-1-oxo-1,3-dihydro-2H-isoindol-2-yl}pentanamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-{[(3R)-5-oxo-1-phenylpyrrolidin-3-yl]carbonyl}-3-azabicyclo[3.1.0]hexane-2-carboxamide;

tert-butyl {(2S)-1-[(2S,4R)-2-({(2S)-1-(1,3-benzothiazol-2-yl)-1-oxo-3-[(3S)-2-oxopyrrolidin-3-yl]propan-2-yl}carbamoyl)-4-methylpiperidin-1-yl]-3-methyl-1-oxobutan-2-yl}carbamate;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[3-methyl-N-(methylsulfonyl)-L-valyl]-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-[N-(ethylsulfonyl)-L-valyl]-6,6-dimethyl-3-azabicyclo[3.1.0]hexane-2-carboxamide;

(3S)—N-{(2S)-1-(1,3-benzothiazol-2-yl)-1-oxo-3-[(3S)-2-oxopyrrolidin-3-yl]propan-2-yl}-2-{(2S)-3-methyl-2-[(methylsulfonyl)amino]butanoyl}-2-azaspiro[4.4]nonane-3-carboxamide;

(1S,3aR,7aS)—N-{(2S)-1-(1,3-benzothiazol-2-yl)-1-oxo-3-[(3S)-2-oxopyrrolidin-3-yl]propan-2-yl}-2-{(2S)-3-methyl-2-[(methylsulfonyl)amino]butanoyl}octahydro-1H-isoindole-1-carboxamide;

(2S,4S)—N-{(2S)-1-(1,3-benzothiazol-2-yl)-1-oxo-3-[(3S)-2-oxopyrrolidin-3-yl]propan-2-yl}-1-[N-(methylsulfonyl)-L-valyl]-4-(propan-2-yl)piperidine-2-carboxamide;

(2S,4R)—N-{(2S)-1-(1,3-benzothiazol-2-yl)-1-oxo-3-[(3S)-2-oxopyrrolidin-3-yl]propan-2-yl}-1-[N-(methylsulfonyl)-L-valyl]-4-(propan-2-yl)piperidine-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[N-(trifluoroacetyl)-L-valyl]-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-{N-[(2S)-1,1,1-trifluoropropan-2-yl]-L-valyl}-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-[N-(2,2-dimethylpropanoyl)-3-methyl-L-valyl]-6,6-dimethyl-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-{[(3R)-1-benzyl-5-oxopyrrolidin-3-yl]carbonyl}-6,6-dimethyl-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-[N-(cyclopropylsulfonyl)-L-valyl]-6,6-dimethyl-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[N-(propan-2-ylsulfonyl)-D-valyl]-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[N-(propan-2-ylsulfonyl)-L-valyl]-3-azabicyclo[3.1.0]hexane-2-carboxamide;

(2S,4S)—N-{(2S)-1-(1,3-benzothiazol-2-yl)-1-oxo-3-[(3S)-2-oxopyrrolidin-3-yl]propan-2-yl}-4-tert-butyl-1-[N-(methylsulfonyl)-L-valyl]piperidine-2-carboxamide;
(2S,4R)—N-{(2S)-1-(1,3-benzothiazol-2-yl)-1-oxo-3-[(3S)-2-oxopyrrolidin-3-yl]propan-2-yl}-4-tert-butyl-1-[N-(methylsulfonyl)-L-valyl]piperidine-2-carboxamide;
(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[3-methyl-N-(trifluoroacetyl)-L-valyl]-3-azabicyclo[3.1.0]hexane-2-carboxamide;
N-(methylsulfonyl)-L-valyl-(4R)—N-{(2S)-1-(1,3-benzothiazol-2-yl)-1-oxo-3-[(3S)-2-oxopyrrolidin-3-yl]propan-2-yl}-4-tert-butoxy-L-prolinamide;
tert-butyl {(2S)-1-[(1R,2S,5S)-2-({(2S)-1-(1,3-benzothiazol-2-yl)-1-oxo-3-[(3S)-2-oxopyrrolidin-3-yl]propan-2-yl}carbamoyl)-6,6-dimethyl-3-azabicyclo[3.1.0]hex-3-yl]-3,3-dimethyl-1-oxobutan-2-yl}carbamate;
(1R,2S,5S)—N-{(2S)-1-(4-chloro-1,3-benzoxazol-2-yl)-1-oxo-3-[(3S)-2-oxopyrrolidin-3-yl]propan-2-yl}-6,6-dimethyl-3-[N-(trifluoroacetyl)-L-valyl]-3-azabicyclo[3.1.0]hexane-2-carboxamide;
(2S,4S)-4-methyl-1-[N-(methylsulfonyl)-L-valyl]-N-{(2S)-1-oxo-3-[(3S)-2-oxopyrrolidin-3-yl]-1-[4-(trifluoromethyl)-1,3-benzoxazol-2-yl]propan-2-yl}piperidine-2-carboxamide;
(2S,4R)-4-methyl-1-[N-(methylsulfonyl)-L-valyl]-N-{(2S)-1-oxo-3-[(3S)-2-oxopyrrolidin-3-yl]-1-[4-(trifluoromethyl)-1,3-benzoxazol-2-yl]propan-2-yl}piperidine-2-carboxamide;
(1R,2S,5S)—N-{(2S)-1-(1,3-benzothiazol-2-yl)-1-oxo-3-[(3S)-2-oxopyrrolidin-3-yl]propan-2-yl}-3-[N-(cyclopropylsulfonyl)-3-methyl-L-valyl]-6,6-dimethyl-3-azabicyclo[3.1.0]hexane-2-carboxamide;
(1R,2S,5S)—N-{(2S)-1-(1,3-benzothiazol-2-yl)-1-oxo-3-[(3S)-2-oxopyrrolidin-3-yl]propan-2-yl}-3-[N-(tert-butylsulfonyl)-L-valyl]-6,6-dimethyl-3-azabicyclo[3.1.0]hexane-2-carboxamide;
(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[3-methyl-N-(propan-2-ylsulfonyl)-L-valyl]-3-azabicyclo[3.1.0]hexane-2-carboxamide;
methyl {(2S)-1-[(1R,2S,5S)-6,6-dimethyl-2-({(2S)-1-oxo-3-[(3S)-2-oxopyrrolidin-3-yl]-1-[4-(trifluoromethyl)-1,3-benzoxazol-2-yl]propan-2-yl}carbamoyl)-3-azabicyclo[3.1.0]hex-3-yl]-3,3-dimethyl-1-oxobutan-2-yl}carbamate;
(2S)—N-{(2S)-1-(1,3-benzothiazol-2-yl)-1-oxo-3-[(3S)-2-oxopyrrolidin-3-yl]propan-2-yl}-6-methyl-3-[N-(methylsulfonyl)-L-valyl]-6-(trifluoromethyl)-3-azabicyclo[3.1.0]hexane-2-carboxamide;
(2S,4R)-4-methyl-1-[N-(methylsulfonyl)-L-valyl]-N-{(2S)-1-oxo-3-[(3S)-2-oxopyrrolidin-3-yl]-1-[4-(trifluoromethyl)-1,3-benzothiazol-2-yl]propan-2-yl}piperidine-2-carboxamide;
(2S,4S)-4-methyl-1-[N-(methylsulfonyl)-L-valyl]-N-{(2S)-1-oxo-3-[(3S)-2-oxopyrrolidin-3-yl]-1-[4-(trifluoromethyl)-1,3-benzothiazol-2-yl]propan-2-yl}piperidine-2-carboxamide;
(1R,2S,5S)—N-{(2S)-1-(1,3-benzothiazol-2-yl)-1-oxo-3-[(3S)-2-oxopyrrolidin-3-yl]propan-2-yl}-3-[N-(tert-butylsulfonyl)-3-methyl-L-valyl]-6,6-dimethyl-3-azabicyclo[3.1.0]hexane-2-carboxamide;
(2S,4R)-4-methyl-N-{(2S)-1-oxo-3-[(3S)-2-oxopyrrolidin-3-yl]-1-[4-(trifluoromethyl)-1,3-benzoxazol-2-yl]propan-2-yl}-1-[N-(trifluoroacetyl)-L-valyl]piperidine-2-carboxamide;
ethyl {(2S)-1-[(1R,2S,5S)-6,6-dimethyl-2-({(2S)-1-oxo-3-[(3S)-2-oxopyrrolidin-3-yl]-1-[4-(trifluoromethyl)-1,3-benzoxazol-2-yl]propan-2-yl}carbamoyl)-3-azabicyclo[3.1.0]hex-3-yl]-3,3-dimethyl-1-oxobutan-2-yl}carbamate;
(1R,2S,5S)-6,6-dimethyl-3-(3-methyl-N-propanoyl-L-valyl)-N-{(2S)-1-oxo-3-[(3S)-2-oxopyrrolidin-3-yl]-1-[4-(trifluoromethyl)-1,3-benzothiazol-2-yl]propan-2-yl}-3-azabicyclo[3.1.0]hexane-2-carboxamide;
(1R,2S,5S)-6,6-dimethyl-3-[N-(methylsulfonyl)-L-valyl]-N-{(2S)-1-oxo-3-[(3S)-2-oxopyrrolidin-3-yl]-1-[4-(trifluoromethyl)-1,3-benzothiazol-2-yl]propan-2-yl}-3-azabicyclo[3.1.0]hexane-2-carboxamide;
(1R,2S,5S)-6,6-dimethyl-3-[N-(methylsulfonyl)-L-valyl]-N-{(2S)-1-oxo-3-[(3S)-2-oxopyrrolidin-3-yl]-1-[7-(trifluoromethyl)-1,3-benzothiazol-2-yl]propan-2-yl}-3-azabicyclo[3.1.0]hexane-2-carboxamide;
(1R,2S,5S)-6,6-dimethyl-N-{(2S)-1-oxo-3-[(3S)-2-oxopyrrolidin-3-yl]-1-[4-(trifluoromethyl)-1,3-benzoxazol-2-yl]propan-2-yl}-3-[N-(trifluoroacetyl)-L-valyl]-3-azabicyclo[3.1.0]hexane-2-carboxamide;
(2S,4R)-4-methyl-N-{(2S)-1-oxo-3-[(3S)-2-oxopyrrolidin-3-yl]-1-[4-(trifluoromethyl)-1,3-benzothiazol-2-yl]propan-2-yl}-1-[N-(trifluoroacetyl)-L-valyl]piperidine-2-carboxamide;
ethyl {(2S)-1-[(1R,2S,5S)-6,6-dimethyl-2-({(2S)-1-oxo-3-[(3S)-2-oxopyrrolidin-3-yl]-1-[4-(trifluoromethyl)-1,3-benzothiazol-2-yl]propan-2-yl}carbamoyl)-3-azabicyclo[3.1.0]hex-3-yl]-3,3-dimethyl-1-oxobutan-2-yl}carbamate;
(1R,2S,5S)-6,6-dimethyl-3-[3-methyl-N-(methylsulfonyl)-L-valyl]-N-{(2S)-1-oxo-3-[(3S)-2-oxopyrrolidin-3-yl]-1-[4-(trifluoromethyl)-1,3-benzothiazol-2-yl]propan-2-yl}-3-azabicyclo[3.1.0]hexane-2-carboxamide;
(1R,2S,5S)-6,6-dimethyl-N-{(2S)-1-oxo-3-[(3S)-2-oxopyrrolidin-3-yl]-1-[4-(trifluoromethyl)-1,3-benzothiazol-2-yl]propan-2-yl}-3-[N-(trifluoroacetyl)-L-valyl]-3-azabicyclo[3.1.0]hexane-2-carboxamide;
(1R,2S,5S)—N-{(2S)-1-(1,3-benzothiazol-2-yl)-1-oxo-3-[(3S)-2-oxopyrrolidin-3-yl]propan-2-yl}-3-[N-(methylsulfonyl)-L-valyl]-6,6-bis(trifluoromethyl)-3-azabicyclo[3.1.0]hexane-2-carboxamide;
(1R,2S,5S)-6,6-dimethyl-3-[3-methyl-N-(methylsulfonyl)-L-valyl]-N-{(2S)-1-oxo-3-[(3S)-2-oxopyrrolidin-3-yl]-1-[4-(trifluoromethyl)-1,3-benzoxazol-2-yl]propan-2-yl}-3-azabicyclo[3.1.0]hexane-2-carboxamide;
(1R,2S,5S)-6,6-dimethyl-3-[N-(methylsulfonyl)-L-valyl]-N-{(2S)-1-oxo-3-[(3S)-2-oxopyrrolidin-3-yl]-1-[4-(trifluoromethyl)-1,3-benzoxazol-2-yl]propan-2-yl}-3-azabicyclo[3.1.0]hexane-2-carboxamide;
(1R,2S,5S)-6,6-dimethyl-N-{(2S)-1-oxo-3-[(3S)-2-oxopyrrolidin-3-yl]-1-[4-(trifluoromethyl)-1,3-benzoxazol-2-yl]propan-2-yl}-3-[N-(propan-2-ylsulfonyl)-L-valyl]-3-azabicyclo[3.1.0]hexane-2-carboxamide; and
(1R,2S,5S)-6,6-dimethyl-3-[3-methyl-N-(propan-2-ylsulfonyl)-L-valyl]-N-{(2S)-1-oxo-3-[(3S)-2-oxopyrrolidin-3-yl]-1-[4-(trifluoromethyl)-1,3-benzoxazol-2-yl]propan-2-yl}-3-azabicyclo[3.1.0]hexane-2-carboxamide;
or a pharmaceutically acceptable salt thereof.

E28 is a compound selected from the group consisting of
(6S)—N-{(2S)-1-(1,3-benzothiazol-2-yl)-1-oxo-3-[(3S)-2-oxopyrrolidin-3-yl]propan-2-yl}-5-{(2S)-3-methyl-2-[(methylsulfonyl)amino]butanoyl}-5-azaspiro[2.4]heptane-6-carboxamide;
(1R,2S,5S)—N-{(2S)-1-(1,3-benzothiazol-2-yl)-1-oxo-3-[(3S)-2-oxopyrrolidin-3-yl]propan-2-yl}-3-[(4-methoxy- 1H-indol-2-yl)carbonyl]-6,6-dimethyl-3-azabicyclo [3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[N-(methylsulfonyl)-L-valyl]-3-azabicyclo[3.1.0]hexane-2-carboxamide;

(1R,2S,5S)-6,6-dimethyl-3-[N-(methylsulfonyl)-L-valyl]-N-{(2S)-1-oxo-3-[(3S)-2-oxopyrrolidin-3-yl]-1-[4-(trifluoromethyl)-1,3-benzothiazol-2-yl]propan-2-yl}-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[N-(trifluoroacetyl)-L-valyl]-3-azabicyclo[3.1.0]hexane-2-carboxamide;

tert-butyl {(2S)-1-[(1R,2S,5S)-2-({(2S)-1-(1,3-benzothiazol-2-yl)-1-oxo-3-[(3S)-2-oxopyrrolidin-3-yl]propan-2-yl}carbamoyl)-6,6-dimethyl-3-azabicyclo[3.1.0]hexan-3-yl]-3,3-dimethyl-1-oxobutan-2-yl}carbamate;

(1R,2S,5S)-6,6-dimethyl-3-[N-(methylsulfonyl)-L-valyl]-N-{(2S)-1-oxo-3-[(3S)-2-oxopyrrolidin-3-yl]-1-[7-(trifluoromethyl)-1,3-benzothiazol-2-yl]propan-2-yl}-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[(2R)-tetrahydrofuran-2-ylcarbonyl]-3-azabicyclo[3.1.0] hexane-2-carboxamide;

(6S)—N-{(2S)-1-(1,3-benzothiazol-2-yl)-1-oxo-3-[(3S)-2-oxopyrrolidin-3-yl]propan-2-yl}-5-[(2R)-tetrahydrofuran-2-ylcarbonyl]-5-azaspiro[2.4]heptane-6-carboxamide;

(1R,2S,5S)—N-{(2S)-1-(1,3-benzothiazol-2-yl)-1-oxo-3-[(3S)-2-oxopyrrolidin-3-yl]propan-2-yl}-3-[N-(cyclopropylsulfonyl)-L-valyl]-6,6-dimethyl-3-azabicyclo[3.1.0] hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-[N-(tert-butylsulfonyl)-3-methyl-L-valyl]-6,6-dimethyl-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-[N-(tert-butylsulfonyl)-L-valyl]-6,6-dimethyl-3-azabicyclo[3.1.0] hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[3-methyl-N-(trifluoroacetyl)-L-valyl]-3-azabicyclo [3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[3-methyl-N-(2-methylpropanoyl)-L-valyl]-3-azabicyclo [3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-(3-methyl-N-propanoyl-L-valyl)-3-azabicyclo[3.1.0] hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-[N-(ethylsulfonyl)-L-valyl]-6,6-dimethyl-3-azabicyclo[3.1.0] hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-[N-(2,2-dimethylpropanoyl)-3-methyl-L-valyl]-6,6-dimethyl-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[3-methyl-N-(methylsulfonyl)-L-valyl]-3-azabicyclo [3.1.0]hexane-2-carboxamide;

(1R,2S,5S)-3-(N-acetyl-3-methyl-L-valyl)-N-{(2S)-1-(1,3-benzothiazol-2-yl)-1-oxo-3-[(3S)-2-oxopyrrolidin-3-yl] propan-2-yl}-6,6-dimethyl-3-azabicyclo[3.1.0]hexane-2-carboxamide; and N-{(2S)-1-(1,3-benzothiazol-2-yl)-1-oxo-3-[(3S)-2-oxopyrrolidin-3-yl]propan-2-yl}-4,4-dimethyl-1-[(2R)-tetrahydrofuran-2-ylcarbonyl]-L-prolinamide;

or a pharmaceutically acceptable salt thereof.

E29 A compound (1R,2S,5S)-6,6-dimethyl-3-[3-methyl-N-(methylsulfonyl)-L-valyl]-N-{(2S)-1-oxo-3-[(3S)-2-oxopyrrolidin-3-yl]-1-[4-(trifluoromethyl)-1,3-benzothiazol-2-yl]propan-2-yl}-3-azabicyclo[3.1.0]hexane-2-carboxamide; or a pharmaceutically acceptable salt thereof.

E30 A compound (1R,2S,5S)-6,6-Dimethyl-3-[N-(methylsulfonyl)-L-valyl]-N-{(2S)-1-oxo-3-[(3S)-2-oxopyrrolidin-3-yl]-1-[4-(trifluoromethyl)-1,3-benzothiazol-2-yl]propan-2-yl}-3-azabicyclo[3.1.0]hexane-2-carboxamide; or a pharmaceutically acceptable salt thereof.

E31 A compound (1R,2S,5S)—N-{(2S)-1-(1,3-Benzothiazol-2-yl)-1-oxo-3-[(3S)-2-oxopyrrolidin-3-yl]propan-2-yl}-6,6-dimethyl-3-[N-(trifluoroacetyl)-L-valyl]-3-azabicyclo[3.1.0]hexane-2-carboxamide; or a pharmaceutically acceptable salt thereof.

E32 A pharmaceutical composition comprising a therapeutically effective amount of a compound of any one of embodiments E1 to E31 or a pharmaceutically acceptable salt thereof, together with a pharmaceutically acceptable carrier.

E33 A pharmaceutical composition of embodiment E32 wherein the composition is in the form of an intravenous, subcutaneous, inhaled or oral dosage form.

E34 A pharmaceutical composition of embodiment E33 wherein the composition is in an oral dosage form.

E35 A pharmaceutical composition of embodiment E32 further comprising an additional therapeutic agent.

E36 A pharmaceutical composition of embodiment E32 wherein the pharmaceutical composition further comprises one or more of dexamethasone, azithromycin, and remdesivir.

E37 A method of treating COVID-19 in a patient, the method comprising administering a therapeutically effective amount of a compound of any one of embodiments E1 to E31 or a pharmaceutically acceptable salt thereof to a patient in need thereof.

E38 A method of treating COVID-19 in a patient, the method comprising administering a pharmaceutical composition of any one of embodiments E32 to E36 to a patient in need thereof.

E39 A method of inhibiting or preventing SARS-CoV-2 viral replication comprising contacting the SARS-CoV-2 coronavirus 3CL protease with a therapeutically effective amount of a compound of embodiments E1 to E31 or a pharmaceutically acceptable salt thereof.

E40 A method of inhibiting or preventing SARS-CoV-2 viral replication in a patient comprising administering to the patient in need of inhibition of or prevention of SARS-CoV-2 viral replication a therapeutically effective amount of a compound of any one of E1 to E31 or a pharmaceutically acceptable salt thereof.

E41 Use of a compound of any one of embodiments E1 to E31 or a pharmaceutically acceptable salt thereof for the treatment of COVID-19.

E42 Use of a compound of any one of embodiments E1 to E31 or a pharmaceutically acceptable salt thereof for the preparation of a medicament that is useful for the treatment of COVID-19.

E43 A compound of any one of embodiments E1 to E31 or a pharmaceutically acceptable salt thereof or a pharmaceutical composition of any one of embodiments E32 to E36, for use in treating COVID-19.

E44 A compound of any one of embodiments E1 to E31 or a pharmaceutically acceptable salt thereof or a pharmaceutical composition of any one of embodiments E32 to E36, for use as a medicament.

The present invention also provides a method of targeting SARS-CoV-2 inhibition as a means of treating indications caused by SARS-CoV-2-related viral infections.

The present invention also provides, in part, a method of identifying cellular or viral pathways interfering with the functioning of the members of which could be used for treating indications caused by SARS-CoV-2 infections by administering a SARS-CoV-2 protease inhibitor as described herein.

The present invention also provides, in part, a method of using SARS-CoV-2 protease inhibitors as described herein as tools for understanding mechanism of action of other SARS-CoV-2 inhibitors.

The present invention also provides, in part, a method of using SARS-CoV-2 3C-like protease inhibitors for carrying out gene-profiling experiments for monitoring the up- or down-regulation of genes for the purpose of identifying inhibitors for treating indications caused by SARS-CoV-2 infections such as COVID-19.

The present invention also provides, in part, a pharmaceutical composition for the treatment of COVID-19 in a mammal containing an amount of a SARS-CoV-2 3C-like protease inhibitor that is effective in treating COVID-19 and a pharmaceutically acceptable carrier.

E45 A method of treating MERS in a patient, the method comprising administering a therapeutically effective amount of a compound of any one of embodiments E1 to E31 or a pharmaceutically acceptable salt thereof to a patient in need thereof.

E46 A method of treating MERS in a patient, the method comprising administering a pharmaceutical composition of any one of embodiments E32 to E36 to a patient in need thereof.

E47 A method of inhibiting or preventing MERS viral replication comprising contacting the SARS-CoV-2 coronavirus 3CL protease with a therapeutically effective amount of a compound of any one of embodiments E1 to E31 or a pharmaceutically acceptable salt thereof.

Another embodiment of the present invention is a method of inhibiting or preventing MERS viral replication in a patient comprising administering to the patient in need of inhibition of or prevention of MERS viral replication a therapeutically effective amount of a compound of any one of embodiments E1 to E31 or a pharmaceutically acceptable salt thereof.

Each of the embodiments described above can be combined with any other embodiment described herein not inconsistent with the embodiment with which it is combined. Furthermore, each of the embodiments described herein envisions within its scope pharmaceutically acceptable salts of the compounds described herein

DETAILED DESCRIPTION OF THE INVENTION

For the purposes of the present invention, as described and claimed herein, the following terms are defined as follows:

As used herein, the terms "comprising" and "including" are used in their open, non-limiting sense. The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The term "alkyl" as used herein refers to a linear or branched-chain saturated hydrocarbyl substituent (i.e., a substituent obtained from a hydrocarbon by removal of a hydrogen); in one embodiment containing from one to six carbon atoms. Non-limiting examples of such substituents include methyl, ethyl, propyl (including n-propyl and isopropyl), butyl (including n-butyl, isobutyl, sec-butyl and tert-butyl), pentyl, isoamyl, hexyl and the like. In another embodiment containing one to three carbons and consisting of methyl, ethyl, n-propyl and isopropyl.

The term "alkynyl" as used herein refers to a linear or branched-chain saturated hydrocarbyl substituent that contains a carbon-carbon triple bond (i.e., a substituent obtained from a triple bond-containing hydrocarbon by removal of a hydrogen); in one embodiment containing from two to six carbon atoms. Non-limiting examples of such substituents include prop-2-yn-1-yl, but-3-yn-1-yl, pent-4-yn-1-yl and hex-5-yn-1-yl.

The term "alkoxy" refers to a linear or branched-chain saturated hydrocarbyl substituent attached to an oxygen radical (i.e., a substituent obtained from a hydrocarbon alcohol by removal of the hydrogen from the OH); in one embodiment containing from one to six carbon atoms. Non-limiting examples of such substituents include methoxy, ethoxy, propoxy (including n-propoxy and isopropoxy), butoxy (including n-butoxy, isobutoxy, sec-butoxy and tert-butoxy), pentoxy, hexoxy and the like. In another embodiment having one to three carbons and consisting of methoxy, ethoxy, n-propoxy and isopropoxy. An alkoxy group which is attached to an alkyl group is referred to as an alkoxyalkyl. An example of an alkoxyalkyl group is methoxymethyl.

The term "alkynyloxy" refers to a linear or branched-chain saturated hydrocarbyl substituent containing a carbon-carbon triple bond attached to an oxygen radical (i.e., a substituent obtained from a triple bond-containing hydrocarbon alcohol by removal of the hydrogen from the OH); in one embodiment containing from three to six carbon atoms. Non-limiting examples of such substituents include propynyloxy, butynyloxy and pentynyloxy and the like.

In some instances, the number of carbon atoms in a hydrocarbyl substituent (i.e., alkyl, cycloalkyl, etc.) is indicated by the prefix "$C_x$-$C_y$-" or "$C_{x-y}$", wherein x is the minimum and y is the maximum number of carbon atoms in the substituent. Thus, for example, "$C_1$-$C_6$ alkyl" or "$C_{1-6}$ alkyl" refers to an alkyl substituent containing from 1 to 6 carbon atoms. Illustrating further, $C_3$-$C_6$ cycloalkyl or $C_{3-6}$-cycloalkyl refers to a saturated cycloalkyl group containing from 3 to 6 carbon ring atoms.

The term "cycloalkyl" refers to a carbocyclic substituent obtained by removing a hydrogen from a saturated carbocyclic molecule, for example one having three to seven carbon atoms. The term "cycloalkyl" includes monocyclic saturated carbocycles. The term "$C_3$-$C_7$ cycloalkyl" means a radical of a three- to seven-membered ring system which includes the groups cyclopropyl, cyclobutyl, cyclopentyl, cyclohexyl, and cycloheptyl. The term "$C_3$-$C_6$ cycloalkyl" means a radical of a three- to six-membered ring system which includes the groups cyclopropyl, cyclobutyl, cyclopentyl and cyclohexyl. The cycloalkyl groups can also be bicyclic or spirocyclic carbocycles. For example, the term "$C_3$-$C_{12}$ cycloalkyl" includes monocyclic carbocycles and bicyclic and spirocyclic cycloalkyl moieties such as bicyclopentyl, bicyclohexyl, bicycloheptyl, bicyclooctyl, bicyclononyl, spiropentyl, spirohexyl, spiroheptyl, spirooctyl and spirononyl.

The term "$C_3$-$C_6$ cycloalkoxy" refers to a three- to six-membered cycloalkyl group attached to an oxygen radical. Examples include cyclopropoxy, cyclobutoxy, cyclopentoxy and cyclohexoxy.

The term "aryl" refers to a carbocyclic aromatic system. The term "$C_6$-$C_1$a aryl" refers to cabocyclic aromatic systems with 3 to 10 atoms and includes phenyl and naphthyl.

In some instances, the number of atoms in a cyclic substituent containing one or more heteroatoms (i.e., heteroaryl or heterocycloalkyl) is indicated by the prefix "x- to y-membered", wherein x is the minimum and y is the maximum number of atoms forming the cyclic moiety of the substituent. Thus, for example, "4- to 6-membered heterocycloalkyl" refers to a heterocycloalkyl containing from 4 to 6 atoms, including one to three heteroatoms, in the cyclic moiety of the heterocycloalkyl. Likewise the phrase "5- to 6-membered heteroaryl" refers to a heteroaryl containing from 5 to 6 atoms, and "5- to 10-membered heteroaryl" refers to a heteroaryl containing from 5 to 10 atoms, each including one or more heteroatoms, in the cyclic moiety of the heteroaryl. Furthermore the phrases "5-membered heteroaryl" and "6-membered heteroaryl" refer to a five-membered heteroaromatic ring system and a six-membered heteroaromatic ring system, respectively. The heteroatoms present in these ring systems are selected from N, O and S.

The term "hydroxy" or "hydroxyl" refers to —OH. When used in combination with another term(s), the prefix "hydroxy" indicates that the substituent to which the prefix is attached is substituted with one or more hydroxy substituents. Compounds bearing a carbon to which one or more hydroxy substituents include, for example, alcohols, enols and phenol. The term cyano refers to a —CN group. The term "oxo" means an oxygen which is attached to a carbon by a double bond (i.e., when $R^3$ is oxo then $R^3$ together with the carbon to which it is attached are a C═O moiety).

The term "halo" or "halogen" refers to fluorine (which may be depicted as —F), chlorine (which may be depicted as —Cl), bromine (which may be depicted as —Br), or iodine (which may be depicted as —I).

The term "heterocycloalkyl" refers to a substituent obtained by removing a hydrogen from a saturated or partially saturated ring structure containing a total of the specified number of atoms, such as 4 to 6 ring atoms or 4 to 12 atoms, wherein at least one of the ring atoms is a heteroatom (i.e., oxygen, nitrogen, or sulfur), with the remaining ring atoms being independently selected from the group consisting of carbon, oxygen, nitrogen, and sulfur. The sulfur may be oxidized [i.e., S(O) or $S(O)_2$] or not. In a group that has a heterocycloalkyl substituent, the ring atom of the heterocycloalkyl substituent that is bound to the group may be a nitrogen heteroatom, or it may be a ring carbon atom. Similarly, if the heterocycloalkyl substituent is in turn substituted with a group or substituent, the group or substituent may be bound to a nitrogen heteroatom, or it may be bound to a ring carbon atom. It is to be understood that a heterocyclic group may be monocyclic, bicyclic, polycyclic or spirocyclic.

The term "heteroaryl" refers to an aromatic ring structure containing the specified number of ring atoms in which at least one of the ring atoms is a heteroatom (i.e., oxygen, nitrogen, or sulfur), with the remaining ring atoms being independently selected from the group consisting of carbon, oxygen, nitrogen, and sulfur. Examples of heteroaryl substituents include 6-membered heteroaryl substituents such as pyridyl, pyrazyl, pyrimidinyl, and pyridazinyl; and 5-membered heteroaryl substituents such as triazolyl, imidazolyl, furanyl, thiophenyl, pyrazolyl, pyrrolyl, oxazolyl, isoxazolyl, thiazolyl, 1,2,3-, 1,2,4-, 1,2,5-, or 1,3,4-oxadiazolyl and isothiazolyl. The heteroaryl group can also be a bicyclic heteroaromatic group such as indolyl, benzofuranyl, benzothienyl, benzimidazolyl, benzothiazolyl, benzoxazolyl, benzoisoxazolyl, oxazolopyridinyl, imidazopyridinyl, imidazopyrimidinyl and the like. In a group that has a heteroaryl substituent, the ring atom of the heteroaryl substituent that is bound to the group may be one of the heteroatoms, or it may be a ring carbon atom. Similarly, if the heteroaryl substituent is in turn substituted with a group or substituent, the group or substituent may be bound to one of the heteroatoms, or it may be bound to a ring carbon atom. The term "heteroaryl" also includes pyridyl N-oxides and groups containing a pyridine N-oxide ring. In addition, the heteroaryl group may contain an oxo group such as the one present in a pyridone group. Further examples include furyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, pyridin-2(1H)-onyl, pyridazin-2(1H)-onyl, pyrimidin-2(1H)-onyl, pyrazin-2(1H)-onyl, imidazo[1,2-a]pyridinyl, and pyrazolo[1,5-a]pyridinyl. The heteroaryl can be further substituted as defined herein.

Examples of single-ring heteroaryls and heterocycloalkyls include furanyl, dihydrofuranyl, tetrahydrofuranyl, thiophenyl, dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiaoxadiazolyl, oxathiazolyl, oxadiazolyl (including oxadiazolyl, 1,2,4-oxadiazolyl, 1,2,5-oxadiazolyl, or 1,3,4-oxadiazolyl), pyranyl (including 1,2-pyranyl or 1,4-pyranyl), dihydropyranyl, pyridinyl, piperidinyl, diazinyl (including pyridazinyl, pyrimidinyl, piperazinyl, triazinyl (including s-triazinyl, as-triazinyl and v-triazinyl), oxazinyl (including 2H-1,2-oxazinyl, 6H-1,3-oxazinyl, or 2H-1,4-oxazinyl), isoxazinyl (including o-isoxazinyl or p-isoxazinyl), oxazolidinyl, isoxazolidinyl, oxathiazinyl (including 1,2,5-oxathiazinyl or 1,2,6-oxathiazinyl), oxadiazinyl (including 2H-1,2,4-oxadiazinyl or 2H-1,2,5-oxadiazinyl), and morpholinyl.

The term "heteroaryl" can also include, when specified as such, ring systems having two rings wherein such rings may be fused and wherein one ring is aromatic and the other ring is not fully part of the conjugated aromatic system (i.e., the heteroaromatic ring can be fused to a cycloalkyl or heterocycloalkyl ring). Non-limiting examples of such ring systems include 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl. It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

If substituents are described as "independently" having more than one variable, each instance of a substituent is selected independent of the other(s) from the list of variables available. Each substituent therefore may be identical to or different from the other substituent(s).

If substituents are described as being "independently selected" from a group, each instance of a substituent is selected independent of the other(s). Each substituent therefore may be identical to or different from the other substituent(s).

As used herein, the term "Formula I" may be hereinafter referred to as a "compound(s) of the invention," "the present invention," and "compound of Formula I." Such terms are also defined to include all forms of the compound of Formula I, including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components, which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

The compounds of the invention have asymmetric carbon atoms. The carbon-carbon bonds of the compounds of the invention may be depicted herein using a solid line ( ), a solid wedge ( ), or a dotted wedge ( ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of Formula I may exhibit the phenomenon of tautomerism; such tautomers are also regarded as compounds of the invention. All such tautomeric forms, and mixtures thereof, are included within the scope of compounds of Formula I. Tautomers exist as mixtures of a tautomeric set in solution. In solid form, usually one tautomer predominates. Even though one tautomer may be described, the present invention includes all tautomers of the compounds of Formula I and salts thereof.

The phrase "pharmaceutically acceptable salts(s)", as used herein, unless otherwise indicated, includes salts of acidic or basic groups which may be present in the compounds described herein. The compounds used in the methods of the invention that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isethionate, lactate, lactobionate, laurate, malate, maleate, mandelate, mesylate, methylsulfate, mucate, napsylate, nitrate, oleate, oxalate, pamoate (embonate), palmitate, pantothenate, phosphate/diphosphate, polygalacturonate, salicylate, stearate, subacetate, succinate, tannate, tartrate, teoclate, tosylate, triethiodode, and valerate salts.

With respect to the compounds of the invention used in the methods of the invention, if the compounds also exist as tautomeric forms then this invention relates to those tautomers and the use of all such tautomers and mixtures thereof.

The subject invention also includes compounds and methods of treatment of COVID-19 and methods of inhibiting SARS-CoV-2 with isotopically labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$ $^{17}O$, $^{31}P$, $^{32}P$ $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or isotopes of other atoms are with the scope of this invention. Certain isotopically labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds used in the methods of this invention and prodrugs thereof can generally be prepared by carrying out the procedures for preparing the compounds disclosed in the art by substituting a readily available isotopically labelled reagent for a non-isotopically labelled reagent.

This invention also encompasses methods using pharmaceutical compositions and methods of treating COVID-19 infections through administering prodrugs of compounds of the invention. Compounds having free amido or hydroxy groups can be converted into prodrugs. Prodrugs include compounds wherein an amino acid residue, or a polypeptide chain of two or more (e.g., two, three or four) amino acid residues is covalently joined through an ester bond to a hydroxy of compounds used in the methods of this invention. The amino acid residues include but are not limited to the 20 naturally occurring amino acids commonly designated by three letter symbols and also include 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem., 1996, 29, 10. Free amines can also be derivatized as amides, sulfonamides or phosphonamides. All of these prodrug moieties may incorporate groups including but not limited to ether, amine and carboxylic acid functionalities.

The compounds of the present invention can be used in the methods of the invention in combination with other drugs. For example, dosing a SARS-CoV-2 coronavirus-infected patient (i.e. a patient with COVID-19) with the SARS-CoV-2 coronavirus 3CL protease inhibitor of the invention and an interferon, such as interferon alpha, or a pegylated interferon, such as PEG-Intron or Pegasus, may provide a greater clinical benefit than dosing either the interferon, pegylated interferon or the SARS-CoV-2 coronavirus inhibitor alone. Other additional agents that can be used in the methods of the present invention include dexamethasone, azithromycin and remdesivir. Examples of greater clinical benefits could include a larger reduction in COVID-19 symptoms, a faster time to alleviation of symptoms, reduced lung pathology, a larger reduction in the amount of SARS-CoV-2 coronavirus in the patient (viral load), and decreased mortality.

The SARS-CoV-2 coronavirus infects cells which express p-glycoprotein. Some of the SARS-CoV-2 coronavirus 3CL protease inhibitors of the invention are p-glycoprotein substrates. Compounds which inhibit the SARS-CoV-2 coronavirus which are also p-glycoprotein substrates may be dosed with a p-glycoprotein inhibitor. Examples of p-glycoprotein inhibitors are verapamil, vinblastine, ketoconazole, nelfinavir, ritonavir or cyclosporine. The p-glycoprotein inhibitors act by inhibiting the efflux of the SARS-CoV-2 coronavirus inhibitors of the invention out of the cell. The inhibition of the p-glycoprotein-based efflux will prevent reduction of intracellular concentrations of the SARS-CoV-2 coronavirus inhibitor due to p-glycoprotein efflux. Inhibition of the p-glycoprotein efflux will result in larger intracellular concentrations of the SARS-CoV-2 coronavirus inhibitors. Dosing a SARS-CoV-2 coronavirus-infected patient with the SARS-CoV-2 coronavirus 3CL protease inhibitors of the invention and a p-glycoprotein inhibitor may lower the amount of SARS-CoV-2 coronavirus 3CL protease inhibitor required to achieve an efficacious dose by increasing the intracellular concentration of the SARS-CoV-2 coronavirus 3CL protease inhibitor.

Among the agents that may be used to increase the exposure of a mammal to a compound of the present invention are those that can act as inhibitors of at least one isoform of the cytochrome P450 (CYP450) enzymes. The isoforms of CYP450 that may be beneficially inhibited include, but are not limited to CYP1A2, CYP2D6, CYP2C9, CYP2C19 and CYP3A4. The compounds used in the methods of the invention include compounds that may be CYP3A4 substrates and are metabolized by CYP3A4. Dosing a SARS-CoV-2 coronavirus-infected patient with a SARS-CoV-2 coronavirus inhibitor which is a CYP3A4 substrate, such as SARS-CoV-2 coronavirus 3CL protease inhibitor, and a CYP3A4 inhibitor, such as ritonavir, nelfinavir or delavirdine, will reduce the metabolism of the SARS-CoV-2 coronavirus inhibitor by CYP3A4. This will result in reduced clearance of the SARS-CoV-2 coronavirus inhibitor and increased SARS-CoV-2 coronavirus inhibitor plasma concentrations. The reduced clearance and higher plasma concentrations may result in a lower efficacious dose of the SARS-CoV-2 coronavirus inhibitor. Additional therapeutic agents that can be used in combination with the SARS-CoV-2 inhibitors in the methods of the present invention include the following:

PLpro inhibitors, Ribavirin, Valganciclovir, #-Thymidine, Aspartame, Oxprenolol, Doxycycline, Acetophenazine, Iopromide, Riboflavin, Reproterol, 2,2'-Cyclocytidine, Chloramphenicol, Chlorphenesin carbamate, Levodropropizine, Cefamandole, Floxuridine, Tigecycline, Pemetrexed, L(+)-Ascorbic acid, Glutathione, Hesperetin, Ademetionine, Masoprocol, Isotretinoin, Dantrolene, Sulfasalazine Anti-bacterial, Silybin, Nicardipine, Sildenafil, Platycodin, Chrysin, Neohesperidin, Baicalin, Sugetriol-3,9-diacetate, (−)-Epigallocatechin gallate, Phaitanthrin D, 2-(3,4-Dihydroxyphenyl)-2-[[2-(3,4-dihydroxyphenyl)-3,4-dihydro-5,7-dihydroxy-2H-1-benzopyran-3-yl]oxy]-3,4-dihydro-2H-1-benzopyran-3,4,5,7-tetrol, 2,2-di(3-indolyl)-3-indolone, (S)-(1S,2R,4aS,5R,8aS)-1-Formamido-1,4a-dimethyl-6-methylene-5-((E)-2-(2-oxo-2,5-dihydrofuran-3-yl)ethenyl)decahydronaphthalen-2-yl-2-amino-3-phenylpropanoate, Piceatannol, Rosmarinic acid, and Magnolol.

3CLpro inhibitors, Lymecycline, Chlorhexidine, Alfuzosin, Cilastatin, Famotidine, Almitrine, Progabide, Nepafenac, Carvedilol, Amprenavir, Tigecycline, Montelukast, Carminic acid, Mimosine, Flavin, Lutein, Cefpiramide, Phenethicillin, Candoxatril, Nicardipine, Estradiol valerate, Pioglitazone, Conivaptan, Telmisartan, Doxycycline, Oxytetracycline, (1S,2R,4aS,5R,8aS)-1-Formamido-1,4a-dimethyl-6-methylene-5-((E)-2-(2-oxo-2,5-dihydrofuran-3-yl)ethenyl)decahydronaphthalen-2-yl5-((R)-1,2-dithiolan-3-yl) pentanoate, Betulonal, Chrysin-7-O-β-glucuronide, Andrographiside, (1S,2R,4aS,5R,8aS)-1-Formamido-1,4a-dimethyl-6-methylene-5-((E)-2-(2-oxo-2,5-dihydrofuran-3-yl)ethenyl)decahydronaphthalen-2-yl 2-nitrobenzoate, 2β-Hydroxy-3,4-seco-friedelolactone-27-oic acid (S)-(1S, 2R,4aS,5R,8aS)-1-Formamido-1,4a-dimethyl-6-methylene-5-((E)-2-(2-oxo-2,5-dihydrofuran-3-yl)ethenyl) decahydronaphthalen-2-yl-2-amino-3-phenylpropanoate, Isodecortinol, Cerevisterol, Hesperidin, Neohesperidin, Andrograpanin, 2-((1R,5R,6R,8aS)-6-Hydroxy-5-(hydroxymethyl)-5,8a-dimethyl-2-methylenedecahydronaphthalen-1-yl)ethyl benzoate, Cosmosiin, Cleistocaltone A, 2,2-Di(3-indolyl)-3-indolone, Biorobin, Gnidicin, Phyllaemblinol, Theaflavin 3,3'-di-O-gallate, Rosmarinic acid, Kouitchenside I, Oleanolic acid, Stigmast-5-en-3-ol, Deacetylcentapicrin, and Berchemol.

RdRp inhibitors, Valganciclovir, Chlorhexidine, Ceftibuten, Fenoterol, Fludarabine, Itraconazole, Cefuroxime, Atovaquone, Chenodeoxycholic acid, Cromolyn, Pancuronium bromide, Cortisone, Tibolone, Novobiocin, Silybin, Idarubicin Bromocriptine, Diphenoxylate, Benzylpenicilloyl G, Dabigatran etexilate, Betulonal, Gnidicin, 2,6,30,6-Dihydroxy-3,4-seco-friedelolactone-27-lactone, 14-Deoxy-11,12-didehydroandrographolide, Gniditrin, Theaflavin 3,3'-di-O-gallate, (R)-((1R,5aS,6R,9aS)-1,5a-Dimethyl-7-methylene-3-oxo-6-((E)-2-(2-oxo-2,5-dihydrofuran-3-yl) ethenyl)decahydro-1H-benzo[c]azepin-1-yl)methyl2-amino-3-phenylpropanoate, 2β-Hydroxy-3,4-seco-friedelolactone-27-oic acid, 2-(3,4-Dihydroxyphenyl)-2-[[2-(3,4-dihydroxyphenyl)-3,4-dihydro-5,7-dihydroxy-2H-1-benzopyran-3-yl]oxy]-3,4-dihydro-2H-1-benzopyran-3,4,5,7-tetrol, Phyllaemblicin B, 14-hydroxycyperotundone, Andrographiside, 2-((1R,5R,6R,8aS)-6-Hydroxy-5-(hydroxymethyl)-5,8a-dimethyl-2-methylenedecahydro naphthalen-1-yl)ethyl benzoate, Andrographolide, Sugetriol-3,9-diacetate, Baicalin, (1S,2R,4aS,5R,8aS)-1-Formamido-1,4a-dimethyl-6-methylene-5-((E)-2-(2-oxo-2,5-dihydrofuran-3-yl)ethenyl)decahydronaphthalen-2-yl 5-((R)-1,2-dithiolan-3-yl)pentanoate, 1,7-Dihydroxy-3-methoxyxanthone, 1,2,6-Trimethoxy-8-[(6-O-β-D-xylopyranosyl-β-D-glucopyranosyl)oxy]-9H-xanthen-9-one, and 1,8-Dihydroxy-6-methoxy-2-[(6-O-β-D-xylopyranosyl-β-D-glucopyranosyl)oxy]-9H-xanthen-9-one, 8-(#6-D-Glucopyranosyloxy)-1,3,5-trihydroxy-9H-xanthen-9-one, Additional therapeutic agents that can be used in the methods of the invention include Diosmin, Hesperidin, MK-3207, Venetoclax, Dihydroergocristine, Bolazine, R428, Ditercalinium, Etoposide, Teniposide, UK-432097, Irinotecan, Lumacaftor, Velpatasvir, Eluxadoline, Ledipasvir, Lopinavir/Ritonavir+Ribavirin, Alferon, and prednisone. Other additional agents useful in the methods of the present invention include dexamethasone, azithromycin and remdesivir.

Other additional agents that can be used in the methods of the present invention include α-ketoamides compounds designated as 11r, 13a and 13b, shown below, as described in Zhang, L.; Lin, D.; Sun, X.; Rox, K.; Hilgenfeld, R.; X-ray Structure of Main Protease of the Novel Coronavirus SARS-CoV-2 Enables Design of α-Ketoamide Inhibitors; bioRxiv preprint doi: https://doi.org/10.1101/2020.02.17.952879

11r

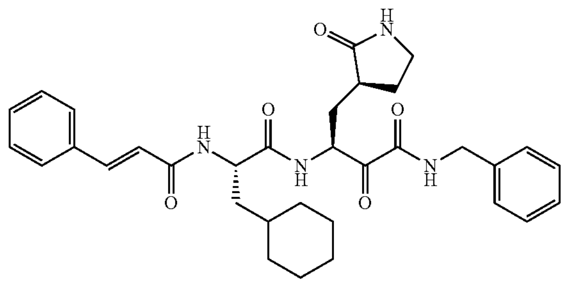

13a

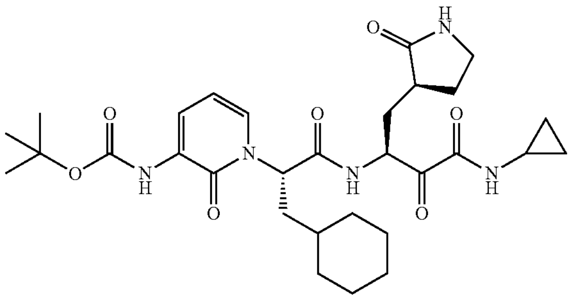

13b

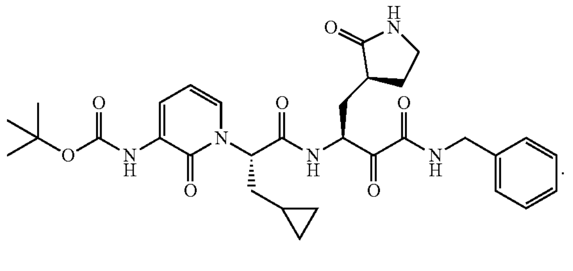

Additional agents that can be used in the methods of the present invention include RIG 1 pathway activators such as those described in U.S. Pat. No. 9,884,876.

The term "SARS-CoV-2 inhibiting agent" means any SARS-CoV-2-related coronavirus 3C-like protease inhibitor compound described herein or a pharmaceutically acceptable salt, hydrate, prodrug, active metabolite or solvate thereof or a compound which inhibits replication of SARS-CoV-2 in any manner.

The term "interfering with or preventing" SARS-CoV-2-related coronavirus ("SARS-CoV-2") viral replication in a cell means to reduce SARS-CoV-2 replication or production of SARS-CoV-2 components necessary for progeny virus in a cell as compared to a cell not being transiently or stably transduced with the ribozyme or a vector encoding the ribozyme. Simple and convenient assays to determine if SARS-CoV-2 viral replication has been reduced include an ELISA assay for the presence, absence, or reduced presence of anti-SARS-CoV-2 antibodies in the blood of the subject (Nasoff, et al., PNAS 88:5462-5466, 1991), RT-PCR (Yu, et al., in Viral Hepatitis and Liver Disease 574-577, Nishioka, Suzuki and Mishiro (Eds.); Springer-Verlag, Tokyo, 1994). Such methods are well known to those of ordinary skill in the art. Alternatively, total RNA from transduced and infected "control" cells can be isolated and subjected to analysis by dot blot or northern blot and probed with SARS-CoV-2-specific DNA to determine if SARS-CoV-2 replication is reduced. Alternatively, reduction of SARS-CoV-2 protein expression can also be used as an indicator of inhibition of SARS-CoV-2 replication. A greater than fifty percent reduction in SARS-CoV-2 replication as compared to control cells typically quantitates a prevention of SARS-CoV-2 replication.

If a SARS-CoV-2 inhibitor compound used in the method of the invention is a base, a desired salt may be prepared by any suitable method known to the art, including treatment of the free base with an inorganic acid (such as hydrochloric acid, hydrobromic acid, sulfuric acid, nitric acid, phosphoric acid, and the like), or with an organic acid (such as acetic acid, maleic acid, succinic acid, mandelic acid, fumaric acid, malonic acid, pyruvic acid, oxalic acid, glycolic acid, salicylic acid, pyranosidyl acid (such as glucuronic acid or galacturonic acid), alpha-hydroxy acid (such as citric acid or tartaric acid), amino acid (such as aspartic acid or glutamic acid), aromatic acid (such as benzoic acid or cinnamic acid), sulfonic acid (such as p-toluenesulfonic acid or ethanesulfonic acid), and the like.

If a SARS-CoV-2 inhibitor compound used in the method of the invention is an acid, a desired salt may be prepared by any suitable method known to the art, including treatment of the free acid with an inorganic or organic base [such as an amine (primary, secondary, or tertiary)], an alkali metal hydroxide, or alkaline earth metal hydroxide. Illustrative examples of suitable salts include organic salts derived from amino acids (such as glycine and arginine), ammonia, primary amines, secondary amines, tertiary amines, and cyclic amines (such as piperidine, morpholine, and piperazine), as well as inorganic salts derived from sodium, calcium, potassium, magnesium, manganese, iron, copper, zinc, aluminum and lithium.

In the case of SARS-CoV-2 inhibitor compounds, prodrugs, salts, or solvates that are solids, it is understood by those skilled in the art that the compound, prodrugs, salts, and solvates used in the method of the invention, may exist in different polymorph or crystal forms, all of which are intended to be within the scope of the present invention and specified formulas. In addition, the compound, salts, prodrugs and solvates used in the method of the invention may exist as tautomers, all of which are intended to be within the broad scope of the present invention.

Solubilizing agents may also be used with the compounds of the invention to increase the compounds' solubility in water of physiologically acceptable solutions. These solubilizing agents include cyclodextrins, propylene glycol, diethylacetamide, polyethylene glycol, Tween, ethanol and micelle-forming agents. Offered solubilizing agents are cyclodextrins, particularly beta-cyclodextrins and in particular hydroxypropyl beta-cyclodextrin and sulfobutylether beta-cyclodextrin.

In some cases, the SARS-CoV-2 inhibitor compounds, salts, prodrugs and solvates used in the method of the invention may have chiral centers. When chiral centers are present, the compound, salts, prodrugs and solvates may exist as single stereoisomers, racemates, and/or mixtures of enantiomers and/or disastereomers. All such single stereoisomers, racemates, and mixtures thereof are intended to be within the broad scope of the present invention.

As generally understood by those skilled in the art, an optically pure compound is one that is enantiomerically pure. As used herein, the term "optically pure" is intended to mean a compound comprising at least a sufficient activity. Preferably, an optically pure amount of a single enantiomer to yield a compound having the desired pharmacological pure compound of the invention comprised at least 90% of a single isomer (80% enantiomeric excess), more preferably at least 95% (90% e.e.), even more preferably at least 97.5% (95%) e.e.), and most preferably at least 99% (98% e.e.).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. In a preferred embodiment of the present invention, "treating" or "treatment" means at least the mitigation of a disease condition in a human, that is alleviated by the inhibition of the activity of the SARS-CoV-2 3C-like protease which is the main protease of SARS-CoV-2, the causative agent for COVID-19. For patients suffering from COVID-19, fever, fatigue, and dry cough are the main manifestations of the disease, while nasal congestion, runny nose, and other symptoms of the upper respiratory tract are rare. Beijing Centers for Diseases Control and Prevention indicated that the typical case of COVID-19 has a progressive aggravation process. COVID-19 can be classified into light, normal, severe, and critical types based on the severity of the disease. National Health Commission of the People's Republic of China. Diagnosis and Treatment of Pneumonia Caused by 2019-nCoV (Trial Version 4). Available online: http://www.nhc.gov.cn/jkj/s3577/202002/573340613ab243b3a7f61df260551dd4/files/c7 91e5a7ea5149f680fdcb34dac0f54e.pdf: (1) Mild cases—the clinical symptoms were mild, and no pneumonia was found on the chest computed tomography (CT); (2) normal cases—fever, respiratory symptoms, and patients found to have imaging manifestations of pneumonia; (3) severe cases—one of the following three conditions: Respiratory distress, respiratory rate ≥30 times/min (in resting state, refers to oxygen saturation ≤93%), partial arterial oxygen pressure (PaO2)/oxygen absorption concentration (FiO2) ≤5300 mmHg (1 mm Hg=0.133 kPa); (4) critical cases—one of the following three conditions: Respiratory failure and the need for mechanical ventilation, shock, or the associated failure of other organs requiring the intensive care unit. The current clinical data shows that the majority of deaths occurred in the older patients. However, severe cases have been documented in young adults who have unique factors, particularly those with chronic diseases, such as diabetes or hepatitis B. Those with a long-term use of hormones or immunosuppressants, and decreased immune function, are likely to get severely infected.

Methods of treatment for mitigation of a disease condition such as COVID-19 include the use of one or more of the compounds of the invention in any conventionally acceptable manner. According to certain preferred embodiments of the invention, the compound or compounds used in the methods of the present invention are administered to a mammal, such as a human, in need thereof. Preferably, the mammal in need thereof is infected with a coronavirus such as the causative agent of COVID-19, namely SARS-CoV-2.

The present invention also includes prophylactic methods, comprising administering an effective amount of a SARS-CoV-2 inhibitor of the invention, or a pharmaceutically acceptable salt, prodrug, pharmaceutically active metabolite, or solvate thereof to a mammal, such as a human at risk for infection by SARS-CoV-2. According to certain preferred embodiments, an effective amount of one or more compounds of the invention, or a pharmaceutically acceptable salt, prodrug, pharmaceutically active metabolite, or solvate thereof is administered to a human at risk for infection by SARS-CoV-2, the causative agent for COVID-19. The prophylactic methods of the invention include the use of one or more of the compounds in the invention in any conventionally acceptable manner.

Certain of the compounds used in the methods of the invention, for example dexamethasone, azithromycin and remdesivir are known and can be made by methods known in the art.

Recent evidence indicates that a new coronavirus SARS-CoV-2 is the causative agent of COVID-19. The nucleotide sequence of the SARS-CoV-2 coronavirus as well as the recently determined L- and S-subtypes have recently been determined and made publicly available.

The activity of the inhibitor compounds as inhibitors of SARS-CoV-2 viral activity may be measured by any of the suitable methods available in the art, including in vivo and in vitro assays. The activity of the compounds of the present invention as inhibitors of coronavirus 3C-like protease activity (such as the 3C-like protease of the SARS-CoV-2 coronavirus) may be measured by any of the suitable methods known to those skilled in the art, including in vivo and in vitro assays. Examples of suitable assays for activity measurements include the antiviral cell culture assays described herein as well as the antiprotease assays described herein, such as the assays described in the Experimental section.

Administration of the SARS-CoV-2 inhibitor compounds and their pharmaceutically acceptable prodrugs, salts, active metabolites, and solvates may be performed according to any of the accepted modes of administration available to those skilled in the art. Illustrative examples of suitable modes of administration include oral, nasal, pulmonary, parenteral, topical, intravenous, injected, transdermal, and rectal. Oral, intravenous, subcutaneous and nasal deliveries are preferred.

A SARS-CoV-2-inhibiting agent may be administered as a pharmaceutical composition in any suitable pharmaceutical form. Suitable pharmaceutical forms include solid, semisolid, liquid, or lyophilized formulations, such as tablets, powders, capsules, suppositories, suspensions, liposomes, and aerosols. The SARS-CoV-2-inhibiting agent may be prepared as a solution using any of a variety of methodologies. For example, SARS-CoV-2-inhibiting agent can be dissolved with acid (e.g., 1 M HCl) and diluted with a sufficient volume of a solution of 5% dextrose in water (D5W) to yield the desired final concentration of SARS-CoV-2-inhibiting agent (e.g., about 15 mM). Alternatively, a solution of D5W containing about 15 mM HCl can be used to provide a solution of the SARS-CoV-2-inhibiting agent at the appropriate concentration. Further, the SARS-CoV-2-inhibiting agent can be prepared as a suspension using, for example, a 1% solution of carboxymethylcellulose (CMC).

Acceptable methods of preparing suitable pharmaceutical forms of the pharmaceutical compositions are known or may be routinely determined by those skilled in the art. For example, pharmaceutical preparations may be prepared following conventional techniques of the pharmaceutical chemist involving steps such as mixing, granulating, and compressing when necessary for tablet forms, or mixing, filling and dissolving the ingredients as appropriate, to give the desired products for intravenous, oral, parenteral, topical, intravaginal, intranasal, intrabronchial, intraocular, intraaural, and/or rectal administration.

Pharmaceutical compositions of the invention may also include suitable excipients, diluents, vehicles, and carriers, as well as other pharmaceutically active agents, depending upon the intended use. Solid or liquid pharmaceutically acceptable carriers, diluents, vehicles, or excipients may be employed in the pharmaceutical compositions. Illustrative solid carriers include starch, lactose, calcium sulfate dihydrate, terra alba, sucrose, talc, gelatin, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., solution), or a nonaqueous or aqueous liquid suspension.

A dose of the pharmaceutical composition may contain at least a therapeutically effective amount of a SARS-CoV-2-inhibiting agent and preferably is made up of one or more pharmaceutical dosage units. The selected dose may be administered to a mammal, for example, a human patient, in need of treatment mediated by inhibition of SARS-CoV-2 related coronavirus activity, by any known or suitable method of administering the dose, including topically, for example, as an ointment or cream; orally; rectally, for example, as a suppository; parenterally by injection; intravenously; or continuously by intravaginal, intranasal, intrabronchial, intraaural, or intraocular infusion. The term patient means animals, including mammals and particularly humans. The patient can be administered the compounds The phrases "therapeutically effective amount" and "effective amount" are intended to mean the amount of an inventive agent that, when administered to a patient such as a mammal in need of treatment, that is sufficient to effect treatment for injury or disease conditions alleviated by the inhibition of coronavirus replication, such as SARS-CoV-2 viral replication. The amount of a given SARS-CoV-2-inhibiting agent used in the method of the invention that will be therapeutically effective will vary depending upon factors such as the particular SARS-CoV-2-inhibiting agent, the disease condition and the severity thereof, the identity and characteristics of the mammal in need thereof, which amount may be routinely determined by those skilled in the art.

It will be appreciated that the actual dosages of the SARS-CoV-2-inhibiting agents used in the pharmaceutical compositions of this invention will be selected according to the properties of the particular agent being used, the particular composition formulated, the mode of administration and the particular site, and the host and condition being treated. Optimal dosages for a given set of conditions can be ascertained by those skilled in the art using conventional dosage-determination tests. For oral administration, e.g., a dose that may be employed is from about 0.01 to about 1000 mg/kg body weight, preferably from about 0.1 to about 500 mg/kg body weight, and even more preferably from about 1 to about 500 mg/kg body weight, with courses of treatment repeated at appropriate intervals. For intravenous dosing a dose of up to 5 grams per day may be employed. Intravenous administration can occur for intermittent periods during a day or continuously over a 24-hour period.

The terms "cytochrome P450-inhibiting amount" and "cytochrome P450 enzyme activity-inhibiting amount", as used herein, refer to an amount of a compound required to decrease the activity of cytochrome P450 enzymes or a particular cytochrome P450 enzyme isoform in the presence of such compound. Whether a particular compound decreases cytochrome P450 enzyme activity, and the amount of such a compound required to do so, can be determined by methods know to those of ordinary skill in the art and the methods described herein.

Protein functions required for coronavirus replication and transcription are encoded by the so-called "replicase" gene.

Two overlapping polyproteins are translated from this gene and extensively processed by viral proteases. The C-proximal region is processed at eleven conserved interdomain junctions by the coronavirus main or "3C-like" protease. The name "3C-like" protease derives from certain similarities between the coronavirus enzyme and the well-known picornavirus 3C proteases. These include substrate preferences, use of cysteine as an active site nucleophile in catalysis, and similarities in their putative overall polypeptide folds. A comparison of the amino acid sequence of the SARS-CoV-2-associated coronavirus 3C-like protease to that of other known coronaviruses such as SARS-CoV shows the amino acid sequences have approximately 96% shared homology.

Amino acids of the substrate in the protease cleavage site are numbered from the N to the C terminus as follows: -P3-P2-P1-P1'-P2'-P3', with cleavage occurring between the P1 and P1' residues (Schechter & Berger, 1967). Substrate specificity is largely determined by the P2, P1 and P1' positions. Coronavirus main protease cleavage site specificities are highly conserved with a requirement for glutamine at P1 and a small amino acid at P1' [*Journal of General Virology,* 83, pp. 595-599 (2002)].

The compounds of the present invention can be prepared according to the methods set forth in Reaction Schemes 1 to 6 below.

The schemes provided below further illustrate and exemplify the compounds of the present invention and methods of preparing such compounds. It is to be understood that the scope of the present invention is not limited in any way by the scope of the following examples and preparations. In the following examples, molecules with a single chiral center may exist as a single enantiomer or a racemic mixture. Those molecules with two or more chiral centers may exist as a single enantiomer, a racemic or otherwise mixture of two enantiomers, or as various mixtures of diastereomers. Such enantiomers, racemates, and diastereomers may be obtained and/or separated by methods known to those skilled in the art. It will be appreciated by one skilled in the art that certain synthetic manipulations may epimerize or racemize a stereocenter, and synthetic conditions may be selected to either promote or discourage such epimerization or racemization.

Scheme 1 illustrates a synthetic sequence for the preparation of compounds of Formula I as shown, wherein a compound of Formula 1 (Thanigaimalai, P. et al., *Eur. J. Med. Chem.* 2013, 68, 372-384) is treated with a heteroaryl compound of Formula 2 that has been deprotonated with a suitable organometallic reagent such as n-butyllithium or lithium diisopropylamide in a reaction-compatible solvent such as diethyl ether, MTBE or THF to afford a heteroaryl ketone of Formula 3. It is understood by those skilled in the art that the selection of specific reaction conditions such as time, temperature, solvent and organometallic reagent may be adjusted depending on the nature of the heterocyclic compound of Formula 2. The compound of Formula 3 may be N-deprotected to provide an amine of Formula 4 using methods well known to those skilled in the art for effecting such deprotections. Frequently, acidic reagents such as hydrogen chloride, methanesulfonic acid, or trifluoroacetic acid are used, typically in a reaction-compatible solvent such as dichloromethane ($CH_2Cl_2$), 1,4-dioxane, 1,2-dichloroethane, or acetonitrile ($CH_3CN$). One skilled in the art will appreciate that the compound of Formula 4 will frequently be obtained as an acid addition salt. The compound of Formula 4 may then be transformed into a compound of Formula I by treatment with a carboxylic acid compound of Formula 5 under appropriate conditions. The carboxylic acid compounds of Formula 5 are either known in the literature or can be readily prepared using procedures well known to those skilled in the art. Methods for coupling the amine of Formula 4 with the carboxylic acid compound of Formula 5 are well known to those skilled in the art. For example, when X=a halogen atom (i.e. chloro), the carboxylic acid compound is known as an acid chloride and the reaction is conducted in the presence of a base to consume the hydrogen halide HX produced as a by-product of the reaction. Examples of suitable bases include, but are not limited to, tertiary amines such as N-methylmorpholine, 2,6-dimethylpyridine, or N,N-diisopropylethylamine, or inorganic bases such as magnesium oxide (MgO), sodium carbonate ($Na_2CO_3$), or potassium bicarbonate ($KHCO_3$). Suitable solvents include, but are not limited to, $CH_2Cl_2$, N,N-dimethylformamide (DMF), tetrahydrofuran (THF), or $CH_3CN$. When X=OH, it is customary to use a reagent or combination of reagents to facilitate the reaction of the carboxylic acid compound of Formula 5. One skilled in the art may choose to use, for example, a coupling reagent such as HATU or a carbodiimide reagent such as 1-ethyl-3-(3-dimethylaminopropyl)carbodiimide (EDC) or N,N'-dicyclohexyl carbodiimide (DCC), optionally in the presence of an auxiliary nucleophile such as hydroxybenzotriazole (HOBt) or (2-hydroxypyridine-N-oxide) HOPO. Further, when X=OH, one skilled in the art may choose to use reagents that are suitable for the formation of mixed carboxyl/carbonic anhydrides, such as carbonyl diimidazole (CDI), isobutyl or ethyl chloroformate, frequently in the presence of a base such as described above. Suitable solvents include, but are not limited to, $CH_2Cl_2$, DMF, THF, or $CH_3CN$. Another approach commonly used by those skilled in the art when X=OH is to treat the carboxylic acid compound of Formula 5 with a carboxylic acid chloride, for example $Me_3CCOCl$, in the presence of a base such as described above to generate a mixed carboxylic anhydride of the Formula 5 wherein X=O(O)CCMe$_3$. Suitable solvents include, but are not limited to, $CH_2Cl_2$, THF, or $CH_3CN$.

Scheme 1

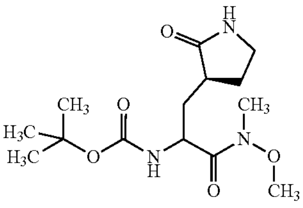

1

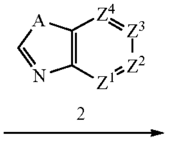

2

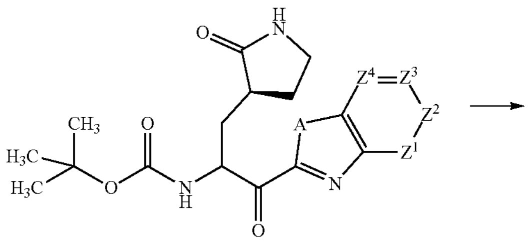

3

-continued

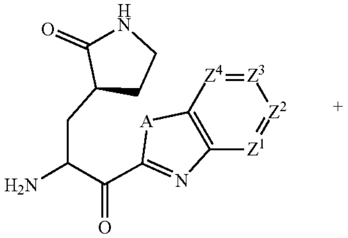

4

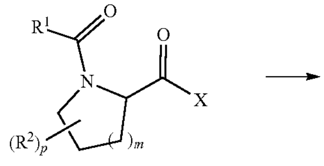

5

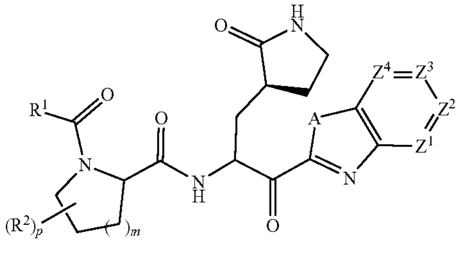

Formula I

Scheme 2 illustrates a synthetic sequence for the preparation of compounds of Formula I as shown, wherein an amine of Formula 4 is coupled with a carboxylic acid compound of Formula 6 under appropriate conditions to afford a compound of Formula 7. Such methods are well known to those skilled in the art and are described in detail for the coupling of the amine of Formula 4 and the carboxylic acid compound of Formula 5 in Scheme 1. The compound of Formula 7 may be N-deprotected to provide an amine of Formula 8 using methods well known to those skilled in the art for effecting such deprotections as described for N-deprotection of the compound of Formula 3 in Scheme 1. The compound of Formula 8 may then be coupled to a carboxylic acid compound of Formula 9 to afford the compound of Formula I. This transformation may be carried out using similar synthetic reaction conditions as for the formation of the compound of Formula 7.

Scheme 2

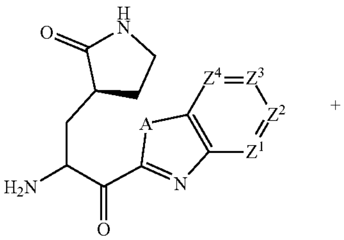

4

-continued

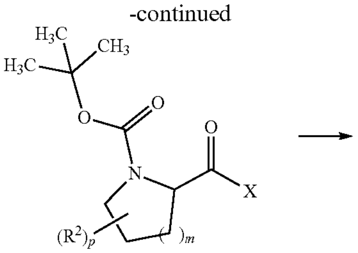

6

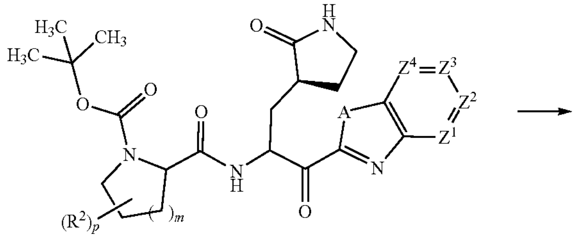

7

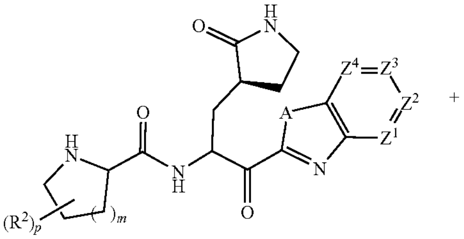

8

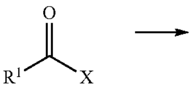

9

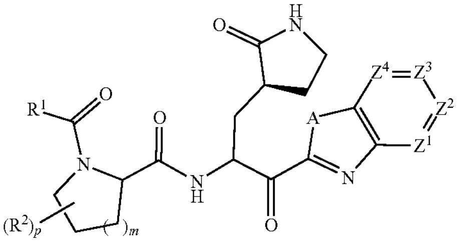

Formula I

Scheme 3 illustrates a synthetic sequence for the preparation of compounds of Formula I as shown, wherein an amine of Formula 8 is coupled with a carboxylic acid compound of Formula 10 (wherein R' can be an alkyl group such as isopropyl or tert-butyl) under appropriate conditions to afford a compound of Formula 11. Such methods are well known to those skilled in the art and are described in detail for the coupling of the amine of Formula 4 and the carboxylic acid compound of Formula 5 in Scheme 1. The compound of Formula 11 may be N-deprotected to provide an amine of Formula 12 using methods well known to those skilled in the art for effecting such deprotections as described for N-deprotection of the compound of Formula 3 in Scheme 1. The compound of Formula 12 may then be coupled to a carboxylic acid compound of Formula 13 (wherein R"C(O) falls within the definition of $R^{1b}$) to afford the compound of Formula I wherein $R^1$ is a group which falls within the definition of $R^{1b}NHC_1$-$C_6$ alkyl-. This transformation may be carried out using similar reaction conditions as for the formation of the compound of Formula 11.

Scheme 3

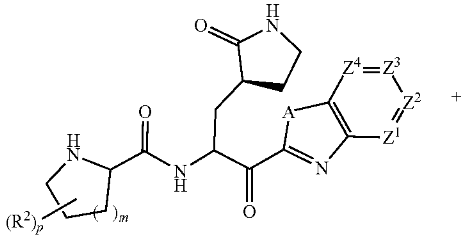

8

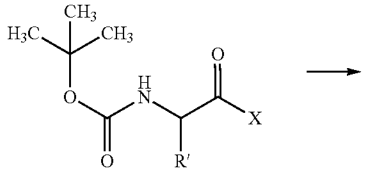

10

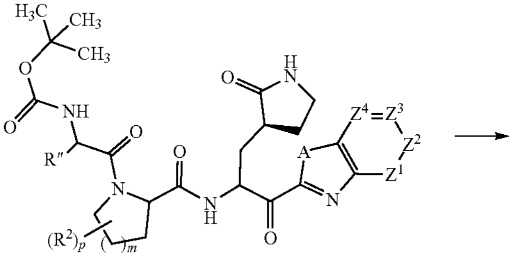

11

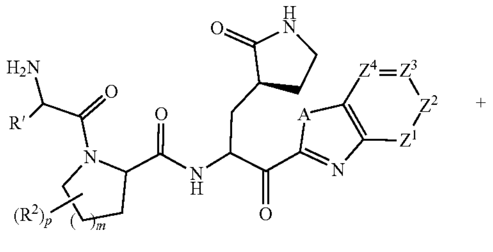

12

-continued

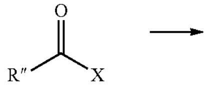

13

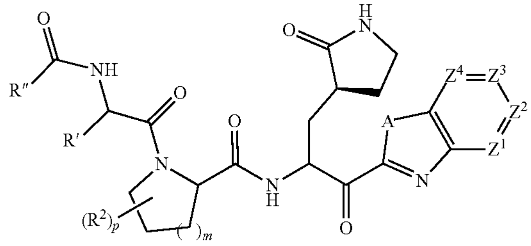

Formula I, where $R^1$ =

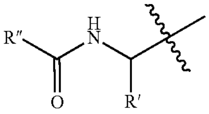

Scheme 4 illustrates synthetic sequences for the preparation of compounds of Formula I as shown, wherein an amine of Formula 12 is reacted with a sulfonyl chloride compound of Formula 14, a chloroformate of Formula 15, or a carbamoyl chloride of Formula 16 under appropriate reaction conditions that are well known to those skilled in the art. The reactions are conducted in the presence of a base to consume the hydrogen halide HX produced as a by-product. Examples of suitable bases include, but are not limited to, tertiary amines such as N-methylmorpholine and N,N-diisopropylethylamine, and suitable solvents include, but are not limited to, $CH_2Cl_2$, DMF, THF, or $CH_3CN$. In each reaction sequence described in this Scheme R' can be an alkyl group such as isopropyl and tert-butyl as described for $R^{1b}NH—C_1-C_6$ alkyl and the moieties $R''S(O)_2—$, R''OC(O)— and $(R'')_2NC(O)$ are within the definition of $R^{1b}$ as described herein.

Scheme 4

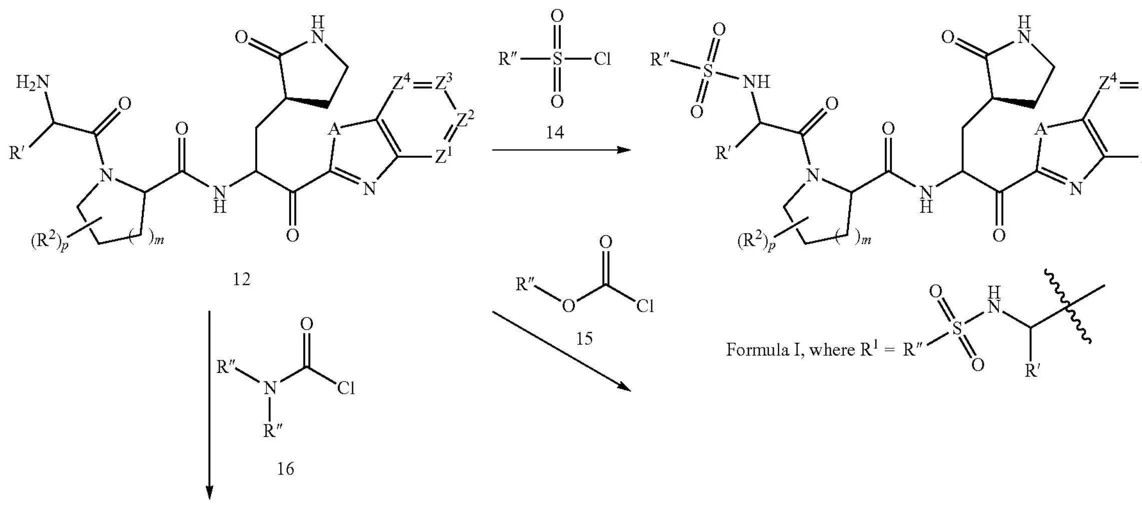

12

14

15

16

Formula I, where $R^1$ = R''

-continued

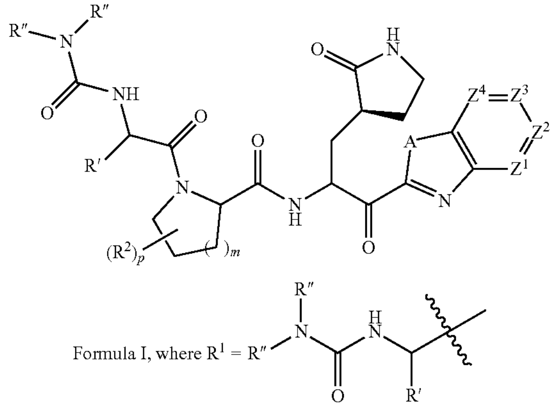

Formula I, where $R^1$ = R″

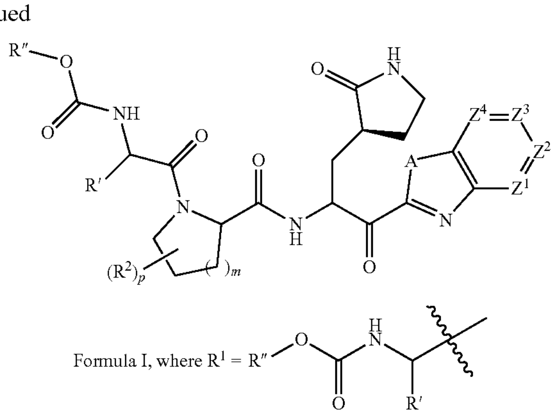

Formula I, where $R^1$ = R″

Scheme 5 illustrates an alternative synthetic sequence for the preparation of compounds of Formula I as shown. The compound of Formula 1 (Thanigaimalai, P. et al., *Eur. J. Med. Chem.* 2013, 68, 372-384) may be N-deprotected to provide an amine of Formula 17 using methods well known to those skilled in the art for effecting such deprotections and as described for N-deprotection of the compound of Formula 3 in Scheme 1. The compound of Formula 17 may then be coupled to a carboxylic acid compound of Formula 5 to afford the compound of Formula 18. This transformation may be carried out using similar conditions as described for the coupling the compound of Formula 4 and the compound of Formula 5 in Scheme 1. The compound of Formula 18 is then reacted with a heteroaryl compound of Formula 2 that has been deprotonated with a suitable organometallic reagent such as n-butyllithium or lithium diisopropylamide in a reaction-compatible solvent such as diethyl ether, methyl tert-butyl ether (MTBE), or THF. It is understood by those skilled in the art that the specific reaction conditions such as time, temperature, solvent and organometallic reagent may be adjusted depending on the nature of the heterocyclic compound of Formula 2.

Scheme 5

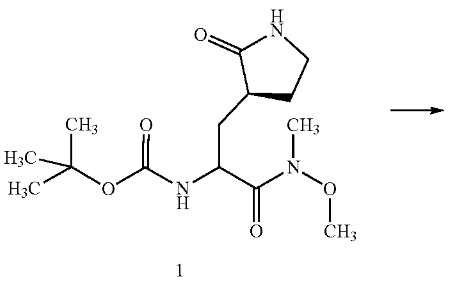

1

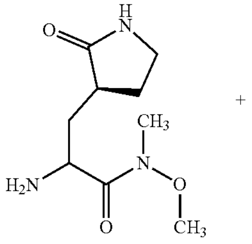

17

-continued

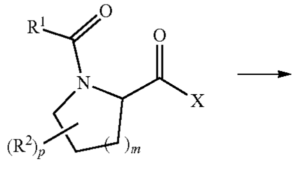

5

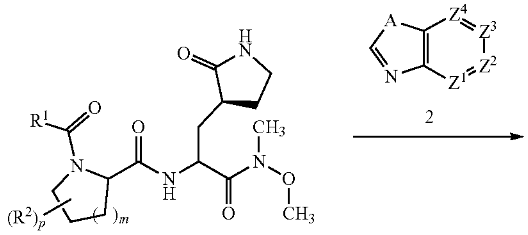

18

2

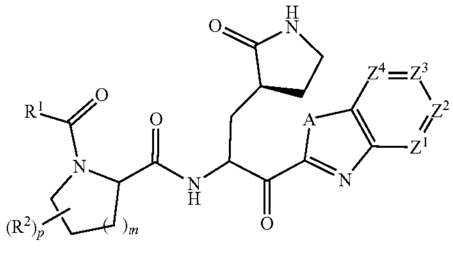

Formula I

Scheme 6 illustrates an alternative synthetic sequence for the preparation of compounds of Formula 3 as shown. The compound of Formula 19 (WO 2018/042343) is reacted with a heteroaryl compound of Formula 2 that has been deprotonated with a suitable organometallic reagent such as n-butyllithium or diisopropylamide in a reaction-compatible solvent such as diethyl ether, MTBE or THF. It is understood by those skilled in the art that the specific reaction conditions such as time, temperature, solvent and organometallic reagent may be adjusted depending on the nature of the heterocyclic compound of Formula 2. The resultant alcohol of Formula 20 may then be oxidized to afford the compound of Formula 3. Such transformations are well known to those skilled in the art. For example, this may be carried out using Dess-Martin periodinane in the presence of a base such as $NaHCO_3$ in a reaction-compatible solvent such as $CH_2Cl_2$.

Scheme 6

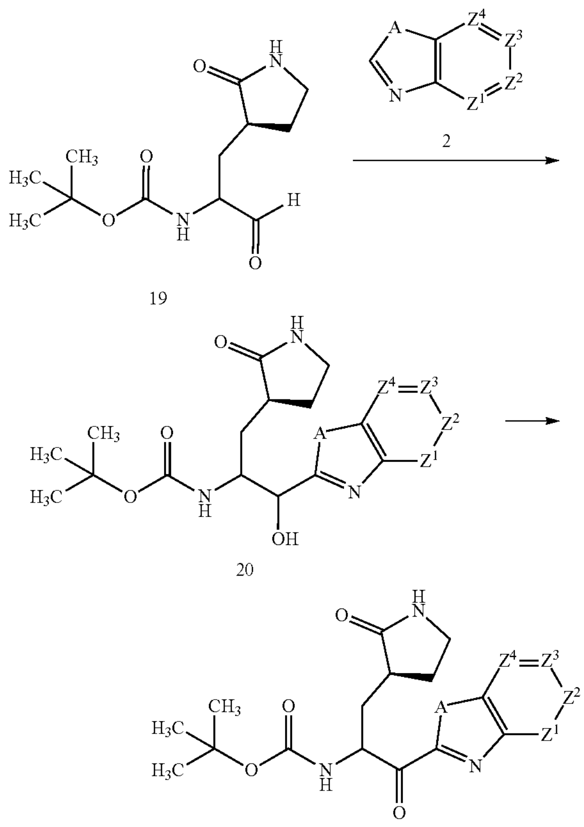

2

19

20

3

One skilled in the art will recognize that still further permutations of order of the bond-forming steps and functional group manipulations in Schemes 1 through 6 may be applied with appropriate considerations. Such permutations in the selection of step order are well known in the chemical literature and one skilled in the art may consult the chemical literature for further guidance if desired. One skilled in the art will recognize that other selections of protecting groups and reagents for effecting the various transformations may be made.

EXAMPLES

Experimental Procedures

The following illustrate the synthesis of various compounds of the present invention. Additional compounds within the scope of this invention may be prepared using the methods illustrated in these Examples, either alone or in combination with techniques generally known in the art. All starting materials in these Preparations and Examples are either commercially available or can be prepared by methods known in the art or as described herein.

Reactions were performed in air or, when oxygen- or moisture-sensitive reagents or intermediates were employed, under an inert atmosphere (nitrogen or argon). When appropriate, reaction apparatuses were dried under dynamic vacuum using a heat gun, and anhydrous solvents (Sure-Seal™ products from Aldrich Chemical Company, Milwaukee, Wisconsin or DriSolv™ products from EMD Chemicals, Gibbstown, NJ) were employed. In some cases, commercial solvents were passed through columns packed with 4 Å molecular sieves, until the following QC standards for water were attained: a) <100 ppm for dichloromethane, toluene, N,N-dimethylformamide, and tetrahydrofuran; b) <180 ppm for methanol, ethanol, 1,4-dioxane, and diisopropylamine. For very sensitive reactions, solvents were further treated with metallic sodium, calcium hydride, or molecular sieves, and distilled just prior to use. Other commercial solvents and reagents were used without further purification. For syntheses referencing procedures in other Examples or Methods, reaction conditions (reaction time and temperature) may vary. Products were generally dried under vacuum before being carried on to further reactions or submitted for biological testing.

When indicated, reactions were heated by microwave irradiation using Biotage Initiator or Personal Chemistry Emrys Optimizer microwaves. Reaction progress was monitored using thin-layer chromatography (TLC), liquid chromatography-mass spectrometry (LCMS), high-performance liquid chromatography (H PLC), and/or gas chromatography-mass spectrometry (GCMS) analyses. TLC was performed on pre-coated silica gel plates with a fluorescence indicator (254 nm excitation wavelength) and visualized under UV light and/or with $I_2$, $KMnO_4$, $COCl_2$, phosphomolybdic acid, and/or ceric ammonium molybdate stains. LCMS data were acquired on an Agilent 1100 Series instrument with a Leap Technologies autosampler, Gemini C18 columns, acetonitrile/water gradients, and either trifluoroacetic acid, formic acid, or ammonium hydroxide modifiers. The column eluent was analyzed using a Waters ZQ mass spectrometer scanning in both positive and negative ion modes from 100 to 1200 Da. Other similar instruments were also used. HPLC data were generally acquired on an Agilent 1100 Series instrument, using the columns indicated, acetonitrile/water gradients, and either trifluoroacetic acid or ammonium hydroxide modifiers. GCMS data were acquired using a Hewlett Packard 6890 oven with an HP 6890 injector, HP-1 column (12 m×0.2 mm×0.33 μm), and helium carrier gas. The sample was analyzed on an HP 5973 mass selective detector scanning from 50 to 550 Da using electron ionization. Purifications were performed by medium performance liquid chromatography (MPLC) using Isco CombiFlash Companion, AnaLogix IntelliFlash 280, Biotage SP1, or Biotage Isolera One instruments and pre-packed Isco RediSep or Biotage Snap silica cartridges. Chiral purifications were performed by chiral supercritical fluid chromatography (SFC), generally using Berger or Thar instruments; columns such as ChiralPAK-AD, -AS, —IC, Chiralcel-OD, or -OJ columns; and $CO_2$ mixtures with methanol, ethanol, 2-propanol, or acetonitrile, alone or modified using trifluoroacetic acid or propan-2-amine. UV detection was used to trigger fraction collection. For syntheses referencing procedures in other Examples or Methods, purifications may vary: in general, solvents and the solvent ratios used for eluents/gradients were chosen to provide appropriate $R_f$s or retention times.

Mass spectrometry data are reported from LCMS analyses. Mass spectrometry (MS) was performed via atmospheric pressure chemical ionization (APCI), electrospray Ionization (ESI), electron impact ionization (EI) or electron scatter (ES) ionization sources. Proton nuclear magnetic spectroscopy ($^1H$ NMR) chemical shifts are given in parts per million downfield from tetramethylsilane and were recorded on 300, 400, 500, or 600 MHz Varian, Bruker, or Jeol spectrometers. Chemical shifts are expressed in parts per million (ppm, δ) referenced to the deuterated solvent residual peaks (chloroform, 7.26 ppm; $CD_2HOD$, 3.31 ppm; acetonitrile-$d_2$, 1.94 ppm; dimethyl sulfoxide-$d_5$, 2.50 ppm; DHO, 4.79 ppm). The peak shapes are described as follows: s, singlet; d, doublet; t, triplet; q, quartet; quin, quintet; m, multiplet; br s, broad singlet; app, apparent. Analytical SFC data were generally acquired on a Berger analytical instrument as described above. Optical rotation data were acquired on a PerkinElmer model 343 polarimeter using a 1 dm cell. Microanalyses were performed by Quantitative Technologies Inc. and were within 0.4% of the calculated values.

Unless otherwise noted, chemical reactions were performed at room temperature (about 23 degrees Celsius).

Unless noted otherwise, all reactants were obtained commercially and used without further purification, or were prepared using methods known in the literature.

The terms “concentrated”, “evaporated”, and “concentrated in vacuo” refer to the removal of solvent at reduced pressure on a rotary evaporator with a bath temperature less than 60° C. The abbreviation “min” and “h” stand for “minutes” and “hours” respectively. The term “TLC” refers to thin-layer chromatography, “room temperature or ambient temperature” means a temperature between 18 to 25° C., “GCMS” refers to gas chromatography-mass spectrometry, “LCMS” refers to liquid chromatography-mass spectrometry, “UPLC” refers to ultra-performance liquid chromatography and “HPLC” refers to high-performance liquid chromatography, “SFC” refers to supercritical fluid chromatography.

Other abbreviations used herein include: br=broad; ° C.=degrees Celsius; d=doublet; dd=doublet of doublets; ddd=doublet of doublet of doublets; DMSO=dimethylsulfoxide; g=gram; Hz=hertz; L=liter; M=molar; m=multiplet; mg=milligram; MHz=megahertz; mL=milliliter, L=microliter, mmol=millimole; s=singlet;

Hydrogenation may be performed in a Parr shaker under pressurized hydrogen gas, or in Thales-nano H-Cube flow hydrogenation apparatus at full hydrogen and a flow rate between 1-2 mL/min at specified temperature.

HPLC, UPLC, LCMS, GCMS, and SFC retention times were measured using the methods noted in the procedures.

In some examples, chiral separations were carried out to separate enantiomers or diastereomers of certain compounds of the invention (in some examples, the separated enantiomers are designated as ENT-1 and ENT-2, according to their order of elution; similarly, separated diastereomers are designated as DIAST-1 and DIAST-2, according to their order of elution). In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated either by the absence of drawn or described stereochemistry, or by the presence of (+/−) adjacent to the structure; in this latter case, the indicated stereochemistry represents just one of the two enantiomers that make up the racemic mixture.

The compounds and intermediates described below were named using the naming convention provided with ACD/ChemSketch 2019.1.1, File Version C05H41, Build 110712 (Advanced Chemistry Development, Inc., Toronto, Ontario, Canada). The naming convention provided with ACD/ChemSketch 2019.1.1 is well known by those skilled in the art and it is believed that the naming convention provided with ACD/ChemSketch 2019.1.1 generally comports with the IUPAC (International Union for Pure and Applied Chemistry) recommendations on Nomenclature of Organic Chemistry and the CAS Index rules.

The $^1H$ NMR spectra of some of the compounds herein indicate a mixture of rotamers, due to the presence of amide and/or carbamate functionality, and have been tabulated to reflect the presence of more than one rotamer.

Example 1

(6S)—N-{(2S)-1-(1,3-Benzothiazol-2-yl)-1-oxo-3-[(3S)-2-oxopyrrolidin-3-yl]propan-2-yl}-5-{(2S)-3-methyl-2-[(methylsulfonyl)amino]butanoyl}-5-azaspiro[2.4]heptane-6-carboxamide (1)

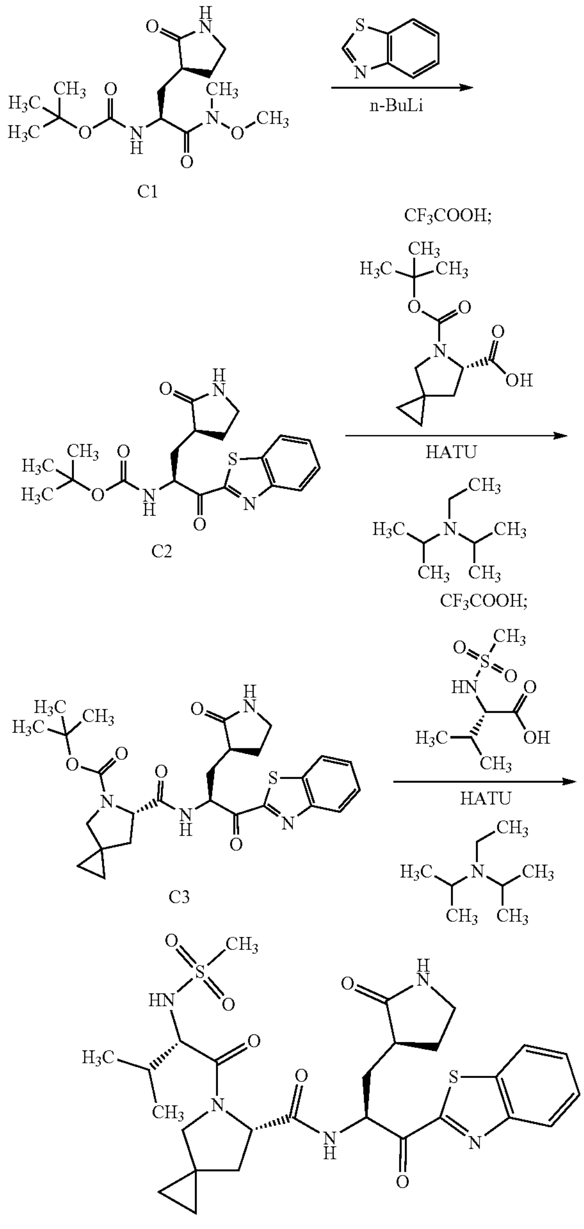

C1

C2

C3

1

Step 1. Synthesis of tert-butyl {(2S)-1-(1,3-benzothiazol-2-yl)-1-oxo-3-[(3S)-2-oxopyrrolidin-3-yl] propan-2-yl}carbamate (C2)

A solution of n-butyllithium in hexane (2.5 M; 20.9 mL, 52.2 mmol) was added in a drop-wise manner to a −78° C. solution of 1,3-benzothiazole (8.06 g, 59.6 mmol) in tetrahydrofuran (120 mL). After the reaction mixture had been stirred for 2 hours, a solution of tert-butyl {(2S)-1-[methoxy(methyl)amino]-1-oxo-3-[(3S)-2-oxopyrrolidin-3-yl]propan-2-yl}carbamate (C1; see Hoffman, R. L. et al., PCT Int. Appl. 2005113580, Dec. 1, 2005 and Thanigaimalai, P. et al., *Eur. J. Med. Chem.* 2013, 68, 372-384; 4.70 g, 14.9 mmol) in tetrahydrofuran (70 mL) was added to the −78° C. reaction mixture, and stirring was continued for 3 hours. LCMS analysis at this point indicated conversion to C2: LCMS m/z 390.2 $[M+H]^+$. Saturated aqueous ammonium chloride solution was added, and the resulting mixture was stirred at 0° C. for 20 minutes, whereupon it was diluted with ethyl acetate, washed sequentially with water and saturated aqueous sodium chloride solution, dried over sodium sulfate, filtered, and concentrated in vacuo. Silica gel chromatography (Gradient: 0% to 100% ethyl acetate in heptane, then 100% ethyl acetate until C2 had eluted) afforded C2 as a light-yellow solid. Yield: 4.20 g, 10.8 mmol, 72%. $^1$H NMR (400 MHz, chloroform-d) δ 8.20-8.15 (m, 1H), 8.01-7.97 (m, 1H), 7.61-7.52 (m, 2H), 5.81 (br d, J=8 Hz, 1H), 5.65-5.55 (m, 1H), 5.54-5.45 (m, 1H), 3.44-3.36 (m, 2H), 2.72-2.59 (m, 2H), 2.23-2.04 (m, 3H), 1.45 (s, 9H).

Step 2. Synthesis of tert-butyl (6S)-6-({(2S)-1-(1,3-benzothiazol-2-yl)-1-oxo-3-[(3S)-2-oxopyrrolidin-3-yl]propan-2-yl}carbamoyl)-5-azaspiro[2.4]heptane-5-carboxylate (C3)

Trifluoroacetic acid (0.41 mL, 5.3 mmol) was added to a 0° C. solution of C2 (83.0 mg, 0.213 mmol) in dichloromethane (1.4 mL). The resulting mixture was stirred at 0° C. for 75 minutes, whereupon it was concentrated in vacuo. The residue was dissolved in N,N-dimethylformamide (2 mL) at 0° C. and treated with N,N-diisopropylethylamine (0.111 mL, 0.637 mmol). In a separate vessel, (6S)-5-(tert-butoxycarbonyl)-5-azaspiro[2.4]heptane-6-carboxylic acid (51.4 mg, 0.213 mmol), 0-(7-azabenzotriazol-1-yl)-N,N,N'N'-tetramethyluronium hexafluorophosphate (HATU; 89.1 mg, 0.234 mmol), and a drop of N,N-diisopropylethylamine were combined in N,N-dimethylformamide (0.5 mL). The resulting solution was added to the 0° C. solution of deprotected C2, and then allowed to warm to room temperature overnight. The reaction mixture was diluted with ethyl acetate, washed sequentially with 10% aqueous potassium bisulfate solution, 5% aqueous sodium bicarbonate solution, and saturated aqueous sodium chloride solution, dried over sodium sulfate, filtered, and concentrated in vacuo. Silica gel chromatography (0% to 100% ethyl acetate in heptane) provided C3 as a solid. Yield: 85 mg, 0.166 mmol, 78%. LCMS m/z 513.3 $[M+H]^+$. $^1$H NMR (400 MHz, chloroform-d) δ [8.60-8.46 (m) and 7.91-7.78 (m), total 1H], 8.16 (d, J=8.0 Hz, 1H), 7.96 (br d, J=8 Hz, 1H), 7.60-7.48 (m, 2H), [6.93-6.75 (m) and 6.35-6.20 (m), total 1H], 5.89-5.70 (m, 1H), 4.52-4.32 (m, 1H), 3.64-3.44 (m, 1H), 3.44-3.31 (m, 2H), 3.19 (d, J=10.3 Hz, 1H), 2.68-2.47 (m, 2H), [2.45-2.17 (m) and 2.17-1.74 (m), total 5H], 1.44 (s, 9H), 0.67-0.44 (m, 4H).

Step 3. Synthesis of (6S)—N-{(2S)-1-(1,3-benzothiazol-2-yl)-1-oxo-3-[(3S)-2-oxopyrrolidin-3-yl] propan-2-yl}-5-{(2S)-3-methyl-2-[(methylsulfonyl) amino]butanoyl}-5-azaspiro[2.4]heptane-6-carboxamide (1)

Trifluoroacetic acid (0.18 mL, 2.3 mmol) was added to a 0° C. solution of C3 (48 mg, 94 μmol) in dichloromethane (1.4 mL). The resulting mixture was stirred at 0° C. for 1 hour, whereupon it was concentrated in vacuo, dissolved in N,N-dimethylformamide (2 mL) at 0° C., and treated with N,N-diisopropylethylamine (48.9 uL, 0.281 mmol). In a separate vessel, N-(methanesulfonyl)-L-valine (18.3 mg, 93.7 μmol), 0-(7-azabenzotriazol-1-yl)-N,N,N'N'-tetramethyluronium hexafluorophosphate (HATU; 39.2 mg, 0.103 mmol), and a drop of N,N-diisopropylethylamine were combined in N,N-dimethylformamide (0.5 mL); the resulting solution was added to the 0° C. solution of deprotected C3. The reaction mixture was allowed to warm to room temperature overnight, whereupon it was diluted with ethyl acetate and sequentially washed with 10% aqueous potassium bisulfate solution, 5% aqueous sodium bicarbonate solution, and saturated aqueous sodium chloride solution. The organic layer was then dried over sodium sulfate, filtered, concentrated in vacuo, and purified using reversed-phase HPLC (Column: Waters Sunfire C18, 19×100 mm, 5 μm; Mobile phase A: water containing 0.05% trifluoroacetic acid; Mobile phase B: acetonitrile containing 0.05% trifluoroacetic acid; Gradient: 20% to 60% B over 8.5 minutes, then 60% to 95% B over 0.5 minute, then 95% B for 1.0 minute; Flow rate: 25 mL/minute) to provide (6S)—N-{(2S)-1-(1,3-benzothiazol-2-yl)-1-oxo-3-[(3S)-2-oxopyrrolidin-3-yl]propan-2-yl}-5-{(2S)-3-methyl-2-[(methylsulfonyl)amino]butanoyl}-5-azaspiro[2.4]heptane-6-carboxamide (1). Yield: 23.4 mg, 39.7 μmol, 42%. LCMS m/z 590.5 $[M+H]^+$. $^1$H NMR (400 MHz, chloroform-d) δ [9.32 (br d, J=5.0 Hz) and 8.01-7.91 (m), total 1H], [8.22 (br d, J=7.9 Hz) and 8.17 (br d, J=7.6 Hz), total 1H], 7.98 (br d, J=7.8 Hz, 1H), 7.64-7.50 (m, 2H), 5.88-5.68 (m, 2H), [5.46-5.32 (m) and 5.24 (d, J=9.6 Hz), total 1H], [4.76-4.67 (m) and 4.54 (dd, J=8.3, 3.2 Hz), total 1H], [3.91 (dd, J=9.6, 5.4 Hz) and 3.80 (dd, J=9.6, 4.0 Hz), total 1H], [3.63-3.44 (m) and 3.44-3.33 (m), total 4H], [3.04-2.96 (m) and 2.82-2.71 (m), total 1H], [2.94 (s) and 2.88 (s), total 3H], [2.62-2.44 (m) and 2.43-2.35 (m), total 2H], 2.27-1.88 (m, 5H, assumed; partially obscured by water peak), 1.09-1.02 (m, 3H), [0.94 (d, J=6.7 Hz) and 0.88 (d, J=6.7 Hz), total 3H], 0.76-0.54 (m, 4H).

Example 2

(1R,2S,5S)—N-{(2S)-1-(1,3-Benzothiazol-2-yl)-1-oxo-3-[(3S)-2-oxopyrrolidin-3-yl]propan-2-yl}-3-[(4-methoxy-1H-indol-2-yl)carbonyl]-6,6-dimethyl-3-azabicyclo[3.1.0]hexane-2-carboxamide (2)

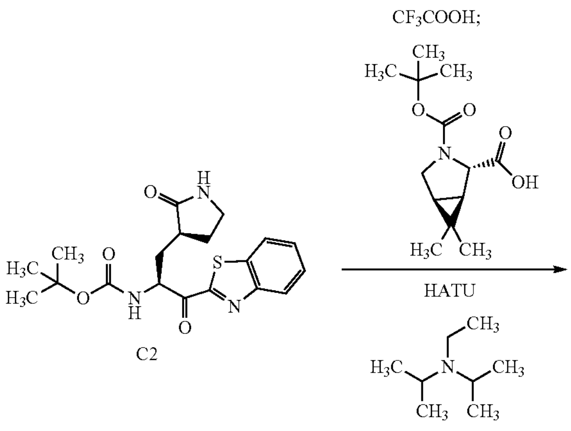

C2

-continued

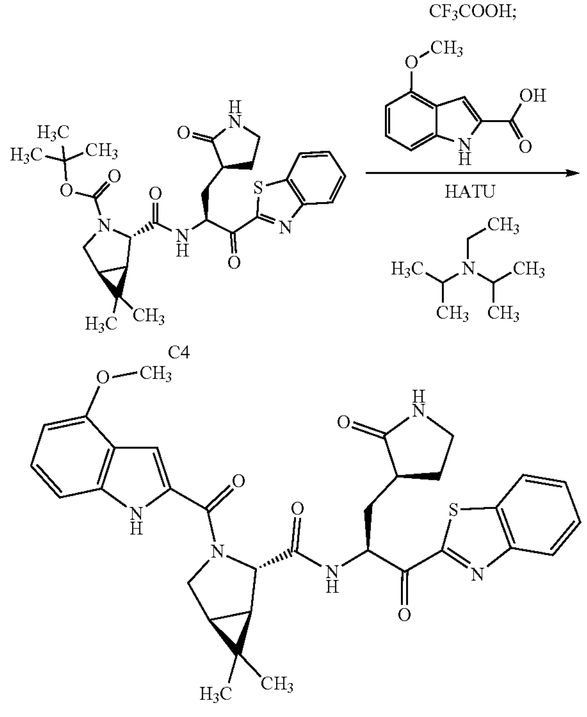

C4

2

Step 1. Synthesis of tert-butyl (1R,2S,5S)-2-({(2S)-1-(1,3-benzothiazol-2-yl)-1-oxo-3-[(3S)-2-oxopyrrolidin-3-yl]propan-2-yl}carbamoyl)-6,6-dimethyl-3-azabicyclo[3.1.0]hexane-3-carboxylate (C4)

Trifluoroacetic acid (0.41 mL, 5.3 mmol) was added to a 0° C. solution of C2 (83 mg, 0.21 mmol) in dichloromethane (1.4 mL). The reaction mixture was stirred at 0° C. for one hour, whereupon LCMS analysis indicated that deprotection was complete: LCMS m/z 290.1 $[M+H]^+$. Concentration in vacuo provided the trifluoroacetic acid salt of the amine, which was dissolved in N,N-dimethylformamide (2 mL), cooled to 0° C. and treated with N,N-diisopropylethylamine (0.111 mL, 0.637 mmol). In a separate vial, a mixture of (1R,2S,5S)-3-(tert-butoxycarbonyl)-6,6-dimethyl-3-azabicyclo[3.1.0]hexane-2-carboxylic acid (54.4 mg, 0.213 mmol), 0-(7-azabenzotriazol-1-yl)-N,N,N'N'-tetramethyluronium hexafluorophosphate (HATU; 89.1 mg, 0.234 mmol), and a drop of N,N-diisopropylethylamine in N,N-dimethylformamide (0.5 mL) was stirred at room temperature until a solution was obtained. This solution was added to the 0° C. solution of the amine salt, and the reaction mixture was allowed to warm to room temperature overnight. Ethyl acetate was added, and the resulting mixture was washed sequentially with 10% aqueous potassium bisulfate solution, 5% aqueous sodium bicarbonate solution, and saturated aqueous sodium chloride solution, dried over sodium sulfate, filtered, and concentrated under reduced pressure. Silica gel chromatography (Gradient: 0% to 100% ethyl acetate in heptane) provided C4 as a clear yellow oil. Yield: 93 mg, 0.18 mmol, 86%. LCMS m/z 527.3 $[M+H]^+$. $^1H$ NMR (400 MHz, chloroform-d) δ [8.34-8.27 (m) and 7.73 (d, J=7.8 Hz), total 1H], 8.21-8.15 (m, 1H), 7.97 (br d, J=7.8 Hz, 1H), 7.62-7.51 (m, 2H), [6.29-6.14 (m), 5.94-5.78 (m), and 5.78-5.69 (m), total 2H], [4.16 (s) and 4.08 (s), total 1H], 3.73-3.63 (m, 1H), [3.58 (d, component of AB quartet, J=11.5 Hz) and 3.45 (d, J=11.2 Hz), total 1H], 3.43-3.34 (m, 2H), 2.70-2.55 (m, 2H), 2.31-1.97 (m, 3H), 1.57-1.31 (m, 2H), [1.39 (s) and 1.38 (s), total 9H], [1.03 (s) and 1.02 (s), total 3H], [0.92 (s) and 0.91 (s), total 3H].

Step 2. Synthesis of (1R,2S,5S)—N-{(2S)-1-(1,3-benzothiazol-2-yl)-1-oxo-3-[(3S)-2-oxopyrrolidin-3-yl]propan-2-yl}-3-[(4-methoxy-1H-indol-2-yl)carbonyl]-6,6-dimethyl-3-azabicyclo[3.1.0]hexane-2-carboxamide (2)

Trifluoroacetic acid (0.18 mL, 2.3 mmol) was added to a 0° C. solution of $C_4$ (50 mg, 95 μmol) in dichloromethane (1.4 mL). After the reaction mixture had been stirred at 0° C. for 1.5 hours, LCMS analysis indicated the presence of the deprotected material: LCMS m/z 427.3 $[M+H]^+$. The reaction mixture was concentrated in vacuo, cooled to 0° C., dissolved in N,N-dimethylformamide (2 mL) and treated with N,N-diisopropylethylamine (49.6 μL, 0.285 mmol). To this 0° C. mixture was added a solution of 4-methoxy-1H-indole-2-carboxylic acid (18.2 mg, 95.2 μmol), O-(7-azabenzotriazol-1-yl)-N,N,N',N'-tetramethyluronium hexafluorophosphate (HATU; 39.7 mg, 0.104 mmol), and a drop of N,N-diisopropylethylamine in N,N-dimethylformamide (0.5 mL). After 2 hours, the reaction mixture was diluted with ethyl acetate, washed sequentially with 10% aqueous potassium bisulfate solution, 5% aqueous sodium bicarbonate solution, and saturated aqueous sodium chloride solution, dried over sodium sulfate, filtered, and concentrated under reduced pressure. Purification via reversed-phase HPLC (Column: Waters Sunfire C18, 19×100 mm, 5 μm; Mobile phase A: water containing 0.05% trifluoroacetic acid; Mobile phase B: acetonitrile containing 0.05% trifluoroacetic acid; Gradient: 30% to 70% B over 8.5 minutes, then 70% to 95% B over 0.5 minute, then 95% B for 1.0 minute; Flow rate: 25 mL/minute) afforded (1R,2S,5S)—N-{(2S)-1-(1,3-benzothiazol-2-yl)-1-oxo-3-[(3S)-2-oxopyrrolidin-3-yl]propan-2-yl}-3-[(4-methoxy-1H-indol-2-yl)carbonyl]-6,6-dimethyl-3-azabicyclo[3.1.0]hexane-2-carboxamide (2). Yield: 18.4 mg, 30.7 μmol, 32%. LCMS m/z 600.5 $[M+H]^+$. Retention time: 2.91 minutes (Column: Waters Atlantis C18, 4.6×50 mm, 5 μm; Mobile phase A: water containing 0.05% trifluoroacetic acid; Mobile phase B: acetonitrile containing 0.05% trifluoroacetic acid; Gradient: 5% to 95% B over 4.0 minutes, then 95% B for 1.0 minute; Flow rate: 2 mL/minute).

Example 3

(1R,2S,5S)—N-{(2S)-1-(1,3-Benzothiazol-2-yl)-1-oxo-3-[(3S)-2-oxopyrrolidin-3-yl]propan-2-yl}-6,6-dimethyl-3-[N-(methylsulfonyl)-L-valyl]-3-azabicyclo[3.1.0]hexane-2-carboxamide (3)

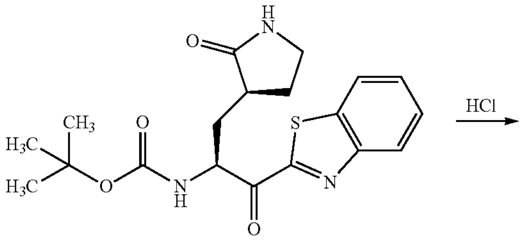

C2

-continued

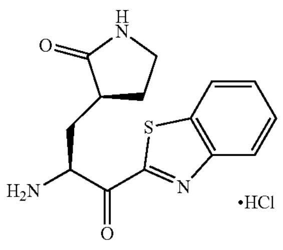

C5

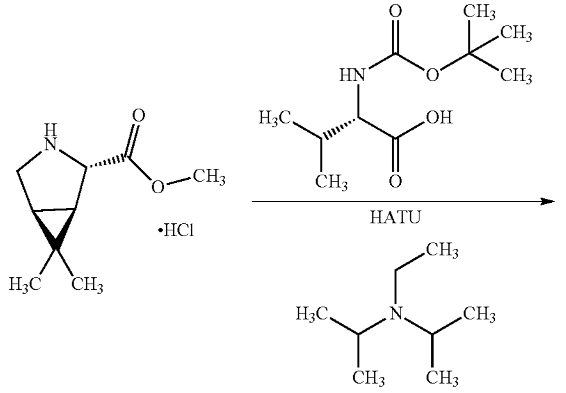

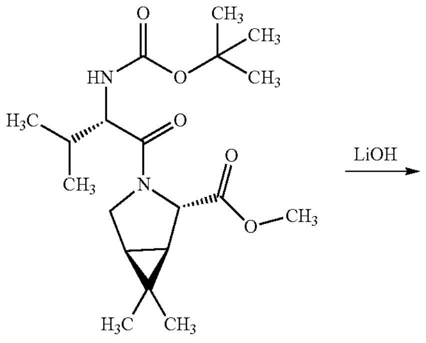

C6

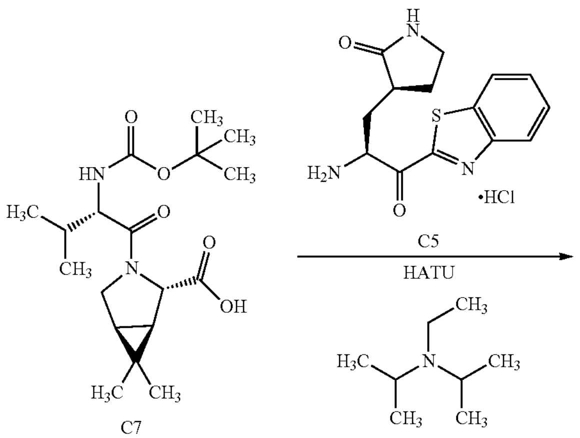

C5

C7

-continued

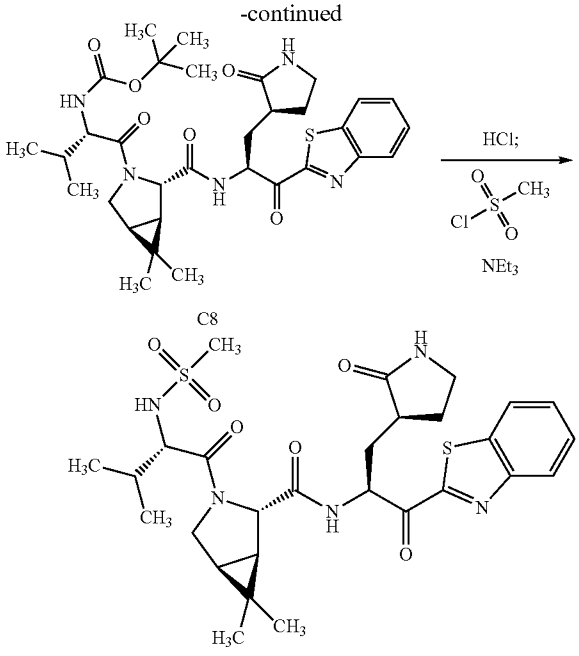

C8

3

Step 1. Synthesis of (3S)-3-[(2S)-2-amino-3-(1,3-benzothiazol-2-yl)-3-oxopropyl]pyrrolidin-2-one, hydrochloride salt (C5)

A solution of C2 (230 mg, 0.591 mml) in dichloromethane (4 mL) was treated with a solution of hydrogen chloride in 1,4-dioxane (4 M; 1.48 mL, 5.92 mmol), followed by ethyl acetate (0.3 mL). The reaction mixture was stirred for 1 hour at room temperature, whereupon it was concentrated in vacuo. Trituration of the residue with diethyl ether afforded C5 as a bright yellow solid. Yield: assumed quantitative. LCMS m/z 290.2 $[M+H]^+$.

Step 2. Synthesis of methyl (1R,2S,5S)-3-[N-(tert-butoxycarbonyl)-L-valyl]-6,6-dimethyl-3-azabicyclo [3.1.0]hexane-2-carboxylate (C6)

A 0° C. mixture of N-(tert-butoxycarbonyl)-L-valine (4.23 g, 19.5 mmol), methyl (1R,2S,5S)-6,6-dimethyl-3-azabicyclo[3.1.0]hexane-2-carboxylate, hydrochloride salt (4.00 g, 19.4 mmol) and N,N-dimethylformamide (97 mL) was treated with O-(7-azabenzotriazol-1-yl)-N,N,N',N'-tetramethyluronium hexafluorophosphate (HATU; 8.13 g, 21.4 mmol). After the reaction mixture had been stirred for 5 minutes, N,N-diisopropylethylamine (8.47 mL, 48.6 mmol) was added and stirring was continued at 0° C. for 2 hours. The reaction mixture was then diluted with aqueous citric acid solution (1 N; 20 mL) and water (40 mL), stirred for 2 minutes, and diluted with ethyl acetate (250 mL). The organic layer was washed with water (3×150 mL), and the combined aqueous layers were extracted with ethyl acetate (100 mL). The combined organic layers were then washed with saturated aqueous sodium chloride solution, dried over sodium sulfate, filtered and concentrated in vacuo. Silica gel chromatography (Gradient: 0% to 100% ethyl acetate in heptane) provided C6 as a gum. Yield: 5.80 g, 15.7 mmol, 81%. LCMS m/z 369.3 $[M+H]^+$. $^1H$ NMR (400 MHz, chloroform-d) δ 5.06 (d, J=9.7 Hz, 1H), 4.45 (s, 1H), 4.12

(dd, J=9.7, 7.8 Hz, 1H), 3.95 (d, component of AB quartet, J=10.2 Hz, 1H), 3.86 (dd, component of ABX system, J=10.1, 4.8 Hz, 1H), 3.74 (s, 3H), 2.04-1.93 (m, 1H), 1.50-1.41 (m, 2H), 1.40 (s, 9H), 1.05 (s, 3H), 1.00 (d, J=6.7 Hz, 3H), 0.95 (d, J=6.8 Hz, 3H), 0.93 (s, 3H).

Step 3. Synthesis of (1R,2S,5S)-3-[N-(tert-butoxycarbonyl)-L-valyl]-6,6-dimethyl-3-azabicyclo[3.1.0]hexane-2-carboxylic acid (C7)

Aqueous lithium hydroxide solution (1 M; 8.14 mL, 8.14 mmol) was added drop-wise to a 0° C. solution of C6 (2.00 g, 5.43 mmol) in a mixture of tetrahydrofuran and methanol (1:1, 30 mL). The reaction mixture was stirred at 0° C. for 2 hours, and then at room temperature for 4 hours, whereupon aqueous lithium hydroxide solution (1 M; 1.67 mL, 1.67 mmol) was added and stirring was continued for 15 minutes. Aqueous lithium hydroxide solution (1 M; 3 mL, 3 mmol) was added once more; after a further 15 minutes, the reaction pH was adjusted to 3 by addition of 1 M hydrochloric acid. The resulting mixture was diluted with water (30 mL), and the aqueous layer was extracted with ethyl acetate (2×75 mL). The combined organic layers were dried over sodium sulfate, filtered, and concentrated in vacuo to afford C7 as an off-white solid. Yield: 1.90 g, 5.36 mmol, 99%. LCMS m/z 355.3 $[M+H]^+$. $^1H$ NMR (400 MHz, DMSO-$d_6$) δ 12.60 (br s, 1H), 7.03 (d, J=8.6 Hz, 1H), 4.10 (s, 1H), 3.98 (d, J=10.3 Hz, 1H), 3.80 (dd, J=9, 9 Hz, 1H), 3.74 (dd, J=10.3, 5.3 Hz, 1H), 1.93-1.81 (m, 1H), 1.54-1.46 (m, 1H), 1.41-1.35 (m, 1H), 1.34 (s, 9H), 1.01 (s, 3H), 0.90-0.83 (m, 9H).

Step 4. Synthesis of tert-butyl {(2S)-1-[(1R,2S,5S)-2-({(2S)-1-(1,3-benzothiazol-2-yl)-1-oxo-3-[(3S)-2-oxopyrrolidin-3-yl]propan-2-yl}carbamoyl)-6,6-dimethyl-3-azabicyclo[3.1.0]hexan-3-yl]-3-methyl-1-oxobutan-2-yl}carbamate (C8)

To a 0° C. solution of C7 (80.8 mg, 0.228 mmol), O-(7-azabenzotriazol-1-yl)-N,N,N,N'-tetramethyluronium hexafluorophosphate (HATU; 86.7 mg, 0.228 mmol), and N,N-diisopropylethylamine (54 μL, 0.31 mmol) in N,N-dimethylformamide (2 mL) was added C5 (60 mg, 0.18 mmol). N,N-Diisopropylethylamine (54 μL, 0.31 mmol) was added, and the reaction mixture was allowed to stir and warm to room temperature overnight. It was then diluted with ethyl acetate, washed sequentially with 10% aqueous potassium bisulfate solution, 5% aqueous sodium bicarbonate solution, and saturated aqueous sodium chloride solution, dried over sodium sulfate, filtered, and concentrated in vacuo. Chromatography on silica gel (Gradient: 0% to 100% ethyl acetate in heptane) afforded C8 as an oil. Yield: 91 mg, 0.14 mmol, 78%. LCMS m/z 626.4 $[M+H]^+$. $^1H$ NMR (400 MHz, chloroform-d), characteristic peaks: δ [8.34 (d, J=7.1 Hz) and 7.78 (d, J=7.3 Hz), total 1H], 8.21-8.13 (m, 1H), 7.98 (br d, J=8 Hz, 1H), 7.62-7.49 (m, 2H), [5.96-5.77 (m) and 5.15 (d, J=9.4 Hz), total 2H], 3.98-3.85 (m, 2H), 3.42-3.27 (m, 2H), [2.77-2.65 (m) and 2.64-2.53 (m), total 2H], 2.25-1.89 (m, 4H), 1.40 (s, 9H), 1.08-1.01 (m, 3H), 1.00-0.87 (m, 9H).

Step 5. Synthesis of (1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[N-(methylsulfonyl)-L-valyl]-3-azabicyclo[3.1.0]hexane-2-carboxamide (3)

A solution of hydrogen chloride in 1,4-dioxane (4 M; 0.364 mL, 1.46 mmol) was added to a solution of C8 (91 mg, 0.14 mmol) in dichloromethane (1 mL), and the reaction mixture was stirred at room temperature for 2 hours, whereupon a solution of hydrogen chloride in 1,4-dioxane (4 M, 0.1 mL, 0.4 mmol) was again added. Stirring was continued for an additional 2 hours, and then the reaction mixture was concentrated in vacuo, dissolved in dichloromethane (1 mL), and cooled to 0° C. To this was added triethylamine (60.5 μL, 0.434 mmol), followed by methanesulfonyl chloride (12.4 μL, 0.160 mmol), and the reaction mixture was stirred at 0° C. for 2.5 hours. It was then partitioned between 10% aqueous potassium bisulfate solution and ethyl acetate; the organic layer was washed with saturated aqueous sodium chloride solution, dried over sodium sulfate, filtered, and concentrated in vacuo. Silica gel chromatography (Gradient: 0% to 100% ethyl acetate in heptane) afforded (1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[N-(methylsulfonyl)-L-valyl]-3-azabicyclo[3.1.0]hexane-2-carboxamide (3) as a white solid. Yield: 18 mg, 30 μmol, 21%. LCMS m/z 604.5 $[M+H]^+$. $^1H$ NMR (400 MHz, chloroform-d), characteristic peaks: δ [9.50 (br d, J=4.8 Hz) and 8.01-7.91 (m), total 1H], [8.22 (d, J=8.0 Hz), 8.17 (d, J=7.8 Hz), total 1H], 7.98 (br d, J=7.8 Hz, 1H), 7.64-7.50 (m, 2H), 5.92-5.79 (m, 1H), [5.77-5.69 (m) and 5.21 (d, J=9.7 Hz), total 1H], [4.41 (s) and 4.22 (s), total 1H], 3.96-3.79 (m, 2H), [3.75 (dd, J=9.8, 3.1 Hz) and 3.69 (d, J=10.1 Hz), total 1H], [3.56 (d, J=12.2 Hz) and 3.50 (ddd, J=10, 10, 6.5 Hz), total 1H], [3.45-3.29 (m) and 3.14-3.03 (m), total 2H], 2.88 (s, 3H), [2.64-2.47 (m) and 2.45-2.36 (m), total 2H], 1.60-1.46 (m, 2H), 1.12-0.92 (m, 9H), [0.89 (d, J=6.7 Hz) and 0.79 (d, J=6.7 Hz), total 3H].

Example 4

(1R,2S,5S)-6,6-Dimethyl-3-[N-(methylsulfonyl)-L-valyl]-N-{(2S)-1-oxo-3-[(3S)-2-oxopyrrolidin-3-yl]-1-[4-(trifluoromethyl)-1,3-benzothiazol-2-yl]propan-2-yl}-3-azabicyclo[3.1.0]hexane-2-carboxamide (4)

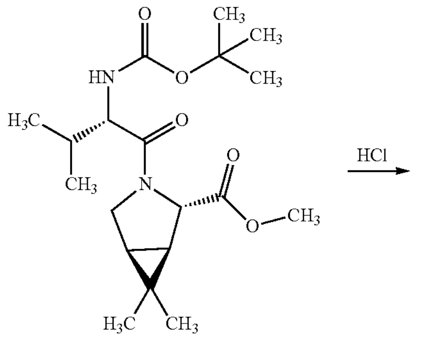

C6

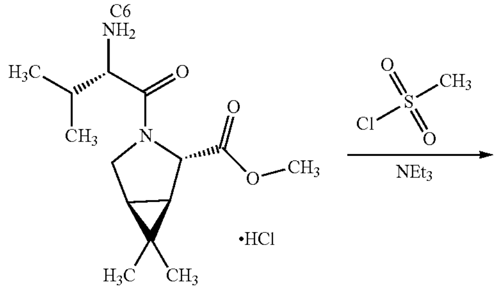

C9

-continued

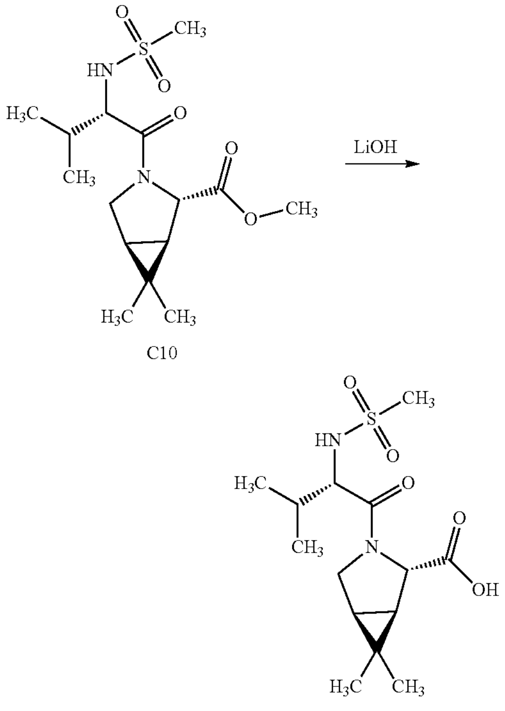

C10

C11

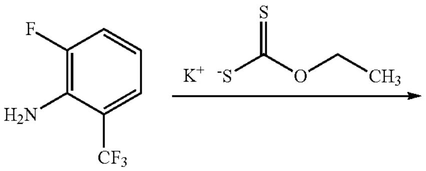

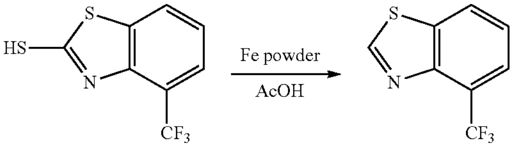

C12

C13

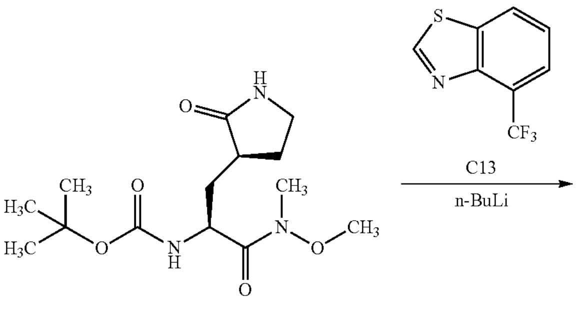

C1

-continued

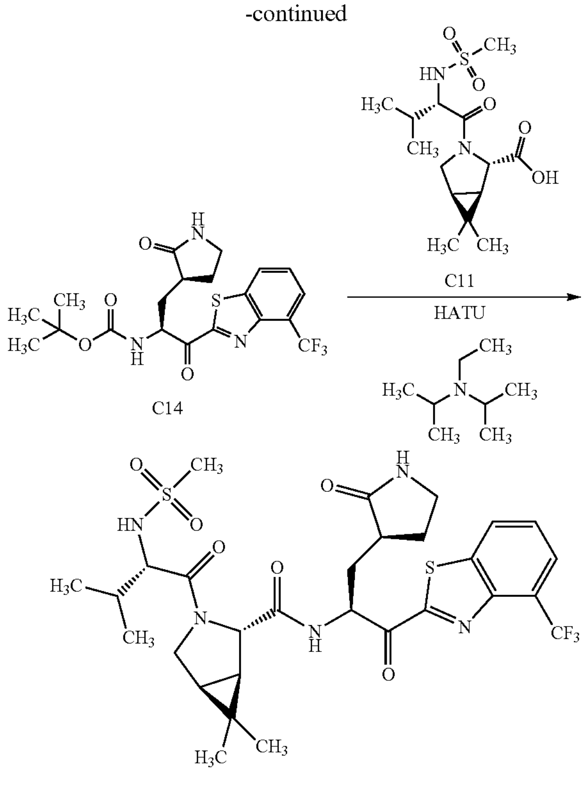

C14

4

Step 1. Synthesis of methyl (1R,2S,5S)-6,6-dimethyl-3-L-valyl-3-azabicyclo[3.1.0]hexane-2-carboxylate, hydrochloride salt (C9)

A solution of hydrogen chloride in 1,4-dioxane (4 M; 15 mL, 60 mmol) was added to a 0° C. solution of C6 (1.00 g, 2.71 mmol) in ethyl acetate (50 mL). The reaction mixture was stirred at 0° C. for 2 hours, whereupon additional hydrogen chloride in 1,4-dioxane solution (4 M; 10 mL, 40 mmol) was added, and stirring was continued at 0° C. for 3 hours, then at room temperature for 1 hour. The reaction mixture was then treated with a solution of hydrogen chloride in 1,4-dioxane (4 M; 10 mL, 40 mmol) and methanol (15 mL) and allowed to stir overnight at room temperature. Concentration in vacuo afforded C9 as a gum, which was progressed directly to the following step. LCMS m/z 269.3 $[M+H]^+$. $^1H$ NMR (400 MHz, DMSO-$d_6$) δ 8.24 (br s, 3H), 4.27 (s, 1H), 3.81-3.61 (m, 3H), 3.67 (s, 3H), 2.21-2.06 (m, 1H), 1.63-1.55 (m, 1H), 1.49 (d, component of AB quartet, J=7.6 Hz, 1H), 1.09-0.88 (m, 12H).

Step 2. Synthesis of methyl (1R,2S,5S)-6,6-dimethyl-3-[N-(methylsulfonyl)-L-valyl]-3-azabicyclo[3.1.0]hexane-2-carboxylate (C10)

Methanesulfonyl chloride (0.223 mL, 2.88 mmol) was added in a drop-wise manner to a 0° C. solution of C9 (from the previous step; s2.71 mmol) and triethylamine (1.10 mL, 7.89 mmol) in dichloromethane (30 mL). After the reaction mixture had been stirred for 2 hours at 0° C., it was diluted with hydrochloric acid (1 M; 20 mL, 20 mmol) and extracted with dichloromethane (2×20 mL). The combined organic layers were dried over sodium sulfate, filtered, concentrated in vacuo, and purified via silica gel chromatography (Gradient: 0% to 100% ethyl acetate in heptane), providing C10 as a clear gum. Yield: 667 mg, 1.92 mmol, 71% over 2 steps. LCMS m/z 347.3 $[M+H]^+$. $^1H$ NMR (400 MHz, DMSO-$d_6$) δ 7.34 (d, J=8.8 Hz, 1H), 4.22 (s, 1H), 3.81-3.70 (m, 3H), 3.65 (s, 3H), 2.82 (s, 3H), 1.93-1.81 (m, 1H), 1.61-1.53 (m, 1H), 1.43 (d, component of AB quartet, J=7.6 Hz, 1H), 1.01 (s, 3H), 0.95 (d, J=6.7 Hz, 3H), 0.93-0.89 (m, 6H).

Step 3. Synthesis of (1R,2S,5S)-6,6-dimethyl-3-[N-(methylsulfonyl)-L-valyl]-3-azabicyclo[3.1.0]hexane-2-carboxylic acid (C11)

Lithium hydroxide monohydrate (162 mg, 3.85 mmol) was added to a solution of C10 (667 mg, 1.92 mmol) in a mixture of tetrahydrofuran, methanol, and water (3:3:1, 19 mL). After the reaction mixture had been stirred at room temperature for 3 hours, it was adjusted to pH 3 to 4 by addition of 1 M hydrochloric acid. The resulting mixture was extracted with ethyl acetate (2×40 mL) and with dichloromethane (30 mL); the combined organic layers were dried over sodium sulfate, filtered, and concentrated in vacuo to afford C11 as a solid. Yield: 550 mg, 1.65 mmol, 86%. LCMS m/z 333.3 $[M+H]^+$. $^1H$ NMR (400 MHz, DMSO-$d_6$) δ 12.66 (br s, 1H), 7.30 (d, J=8.9 Hz, 1H), 4.14 (s, 1H), 3.80-3.69 (m, 3H), 2.81 (s, 3H), 1.94-1.82 (m, 1H), 1.57-1.50 (m, 1H), 1.41 (d, component of AB quartet, J=7.6 Hz, 1H), 1.02 (s, 3H), 0.96 (d, J=6.7 Hz, 3H), 0.93-0.88 (m, 6H).

Step 4. Synthesis of 4-(trifluoromethyl)-1,3-benzothiazole-2-thiol (C12)

To a solution of 2-fluoro-6-(trifluoromethyl)aniline (20.0 g, 112 mmol) in N,N-dimethylformamide (220 mL) was added potassium O-ethyl carbonodithioate (39.4 g, 246 mmol). The reaction mixture was heated at 120° C. overnight, whereupon LCMS analysis indicated the presence of C12: LCMS m/z 236.0 $[M+H]^+$. After the reaction mixture had cooled to room temperature, it was diluted with water (1.0 L), and the resulting solution was treated with hydrochloric acid (1 M; 200 mL, 200 mmol). The precipitated solid was isolated via filtration, dissolved in ethyl acetate, dried over magnesium sulfate, filtered, and concentrated in vacuo, affording C12 as a pale pink solid. Yield: 18.0 g, 76.5 mmol, 68%. $^1H$ NMR (400 MHz, chloroform-d) δ 9.89 (br s, 1H), 7.65-7.56 (m, 2H), 7.37 (dd, J=8, 8 Hz, 1H).

Step 5. Synthesis of 4-(trifluoromethyl)-1,3-benzothiazole (C13)

Iron powder (37.4 g, 670 mmol) was added portion-wise to a 110° C. solution of C12 (18.2 g, 77.4 mmol) in acetic acid (450 mL). After the reaction mixture had been stirred at 110° C. for 3 hours, LCMS analysis indicated the presence of C13: LCMS m/z 204.0 $[M+H]^+$. The reaction mixture was cooled to room temperature and filtered; the filtrate was concentrated in vacuo. The residue was dissolved in ethyl acetate, washed sequentially with saturated aqueous sodium bicarbonate solution and with saturated aqueous sodium chloride solution, dried over magnesium sulfate, filtered, and concentrated under reduced pressure. Silica gel chromatography (Gradient: 0% to 20% ethyl acetate in heptane) provided C13 as a solid. Yield: 12.5 g, 61.5 mmol, 79%. $^1H$ NMR (400 MHz, chloroform-d) δ 9.19 (s, 1H), 8.18 (d, J=8.1 Hz, 1H), 7.84 (d, J=7.6 Hz, 1H), 7.54 (dd, J=8, 8 Hz, 1H).

Step 6. Synthesis of tert-butyl {(2S)-1-oxo-3-[(3S)-2-oxopyrrolidin-3-yl]-1-[4-(trifluoromethyl)-1,3-benzothiazol-2-yl]propan-2-yl}carbamate (C14)

A solution of n-butyllithium (2.5 M; 18.6 mL, 46.5 mmol) was added in a drop-wise manner to a −78° C. solution of C13 (10.8 g, 53.2 mmol) in tetrahydrofuran (130 mL). The reaction mixture was stirred at −78° C. for 1 hour, whereupon a solution of C1 (4.20 g, 13.3 mmol) in tetrahydrofuran (36 mL) was added at −78° C. After 1 hour, the reaction was quenched by addition of saturated aqueous ammonium chloride solution, and stirred at 0° C. for 20 minutes. It was then diluted with ethyl acetate, washed sequentially with water and saturated aqueous sodium chloride solution, dried over sodium sulfate, filtered, and concentrated in vacuo. Chromatography on silica gel (Gradient: 0% to 100% ethyl acetate in heptane) provided C14 as a white solid. Yield: 4.40 g, 9.62 mmol, 72%. LCMS m/z 458.2 $[M+H]^+$. $^1H$ NMR (400 MHz, chloroform-d) δ 8.20 (d, J=8.2 Hz, 1H), 7.89 (d, J=7.5 Hz, 1H), 7.64 (dd, J=8, 8 Hz, 1H), 5.75 (br s, 1H), 5.66-5.55 (m, 2H), 3.48-3.36 (m, 2H), 2.75-2.60 (m, 2H), 2.35-2.16 (m, 2H), 2.12-2.00 (m, 1H), 1.45 (s, 9H).

Step 7. Synthesis of (1R,2S,5S)-6,6-dimethyl-3-[N-(methylsulfonyl)-L-valyl]-N-{(2S)-1-oxo-3-[(3S)-2-oxopyrrolidin-3-yl]-1-[4-(trifluoromethyl)-1,3-benzothiazol-2-yl]propan-2-yl}-3-azabicyclo[3.1.0]hexane-2-carboxamide (4)

A solution of hydrogen chloride in 1,4-dioxane (4 M; 1.1 mL, 4.4 mmol) was added to a 0° C. solution of C14 (100 mg, 0.219 mmol) in dichloromethane (1 mL); after 10 minutes, methanol was added to dissolve the solids present, and the reaction mixture was allowed to stir at room temperature for 1 hour. It was then concentrated in vacuo, dissolved in N,N-dimethylformamide (1 mL), cooled to 0° C., and treated with N,N-diisopropylethylamine (0.190 mL, 1.09 mmol). In a separate vial, C11 (72.7 mg, 0.219 mmol), O-(7-azabenzotriazol-1-yl)-N,N,N,N'-tetramethyluronium hexafluorophosphate (HATU; 91.4 mg, 0.240 mmol), and a drop of N,N-diisopropylethylamine were combined in N,N-dimethylformamide; the resulting solution was added in a drop-wise manner to the 0° C. solution of deprotected C14. The reaction mixture was allowed to warm to room temperature and stir for 1 hour, whereupon it was diluted with ethyl acetate, washed with water and with saturated aqueous sodium chloride solution, dried over sodium sulfate, filtered, and concentrated in vacuo. Silica gel chromatography (Gradient: 0% to 100% ethyl acetate in heptane) afforded (1R,2S,5S)-6,6-dimethyl-3-[N-(methylsulfonyl)-L-valyl]-N-{(2S)-1-oxo-3-[(3S)-2-oxopyrrolidin-3-yl]-1-[4-(trifluoromethyl)-1,3-benzothiazol-2-yl]propan-2-yl}-3-azabicyclo[3.1.0]hexane-2-carboxamide (4) as a light-brown solid. Yield: 35 mg, 52 μmol, 24%. LCMS m/z 672.3 $[M+H]^+$. $^1H$ NMR (400 MHz, chloroform-d), characteristic peaks: δ [9.34 (br d, J=5.0 Hz) and 7.93-7.85 (m), total 2H], 8.19 (d, J=8.2 Hz, 1H), 7.63 (dd, J=8, 8 Hz, 1H), [6.17 (s) and 5.94 (s), total 1H], [5.80 (ddd, J=11.6, 7.2, 2.8 Hz), 5.74-5.63 (m), and 5.38 (d, J=9.7 Hz), total 2H], [4.47 (s) and 4.26 (s), total 1H], 3.95-3.86 (m, 1H), [3.83 (dd, J=12.3, 5.4 Hz) and 3.79-3.65 (m), total 2H], [3.56 (d, J=12.2 Hz) and 3.48 (ddd, J=9.6, 9.6, 6.8 Hz), total 1H], 3.43-3.31 (m, 1H), [3.10-3.00 (m) and 2.78-2.67 (m), total 1H], 2.84 (s, 3H), 2.62-2.48 (m, 1H), [2.39 (dd, J=14.2, 3.6, 3.4 Hz) and 2.29 (ddd, J=14.0, 9.0, 3.0 Hz), total 1H], [1.09-1.04 (m) and 1.02 (d, J=6.7 Hz), total 6H], [0.96 (s) and 0.95 (s), total 3H], [0.89 (d, J=6.7 Hz) and 0.76 (d, J=6.8 Hz), total 3H].

Example 5

(1R,2S,5S)—N-{(2S)-1-(1,3-Benzothiazol-2-yl)-1-oxo-3-[(3S)-2-oxopyrrolidin-3-yl]propan-2-yl}-6,6-dimethyl-3-[N-(trifluoroacetyl)-L-valyl]-3-azabicyclo[3.1.0]hexane-2-carboxamide (5)

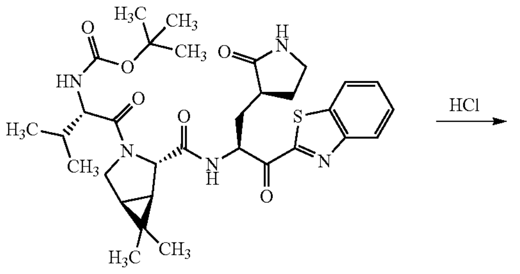

C8

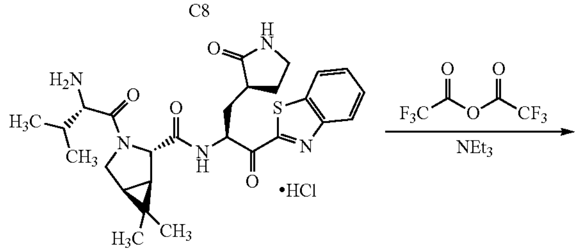

C15

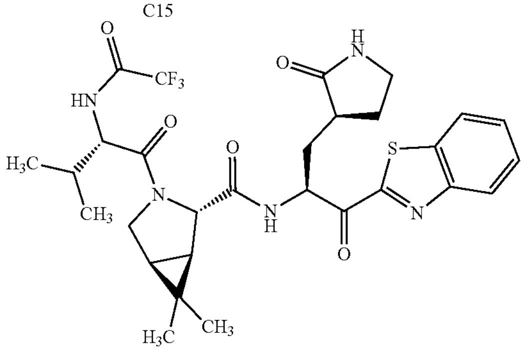

5

Step 1. Synthesis of (1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-L-valyl-3-azabicyclo[3.1.0]hexane-2-carboxamide, hydrochloride salt (C15)

A solution of hydrogen chloride in 1,4-dioxane (4 M; 1.21 mL, 4.84 mmol) was added to a solution of C8 (303 mg, 0.484 mmol) in dichloromethane (3 mL). After the reaction mixture had been stirred at room temperature for 1 hour, LCMS analysis indicated conversion to C15: LCMS m/z 526.3 $[M+H]^+$. Solvents were removed by concentration in vacuo, and the residue was triturated with diethyl ether, providing C15 as a yellow solid. Yield: 250 mg, 0.445 mmol, 92%.

Step 2. Synthesis of (1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[N-(trifluoroacetyl)-L-valyl]-3-azabicyclo[3.1.0]hexane-2-carboxamide (5)

To a 0° C. solution of C15 (20 mg, 36 μmol) in dichloromethane (0.4 mL) was added triethylamine (15.8 μL, 0.113 mmol), followed by trifluoroacetic anhydride (5.1 μL, 36 μmol). The reaction mixture was stirred at 0° C. for 2 hours, whereupon it was treated with methanol (2 mL), stirred for an additional 15 minutes, and concentrated in vacuo. Purification via reversed-phase HPLC (Column: Waters Sunfire C18, 19×100 mm, 5 μm; Mobile phase A: water containing 0.05% trifluoroacetic acid (v/v); Mobile phase B: acetonitrile containing 0.05% trifluoroacetic acid (v/v); Gradient: 30% to 60% B over 8.5 minutes, then 60% to 95% B over 0.5 minutes, then 95% B for 1.0 minute; Flow rate: 25 mL/minute) afforded (1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[N-(trifluoroacetyl)-L-valyl]-3-azabicyclo[3.1.0]hexane-2-carboxamide (5). Yield: 5.6 mg, 9.0 μmol, 25%. LCMS m/z 622.7 $[M+H]^+$. Retention time: 3.01 minutes (Analytical conditions. Column: Waters Atlantis C18, 4.6×50 mm, 5 μm; Mobile phase A: water containing 0.05% trifluoroacetic acid (v/v); Mobile phase B: acetonitrile containing 0.05% trifluoroacetic acid (v/v); Gradient: 5% to 95% B over 4.0 minutes, then 95% B for 1.0 minute; Flow rate: 2 mL/minute).

Alternate Synthesis of Example 5

(1R,2S,5S)—N-{(2S)-1-(1,3-Benzothiazol-2-yl)-1-oxo-3-[(3S)-2-oxopyrrolidin-3-yl]propan-2-yl}-6,6-dimethyl-3-[N-(trifluoroacetyl)-L-valyl]-3-azabicyclo[3.1.0]hexane-2-carboxamide (5)

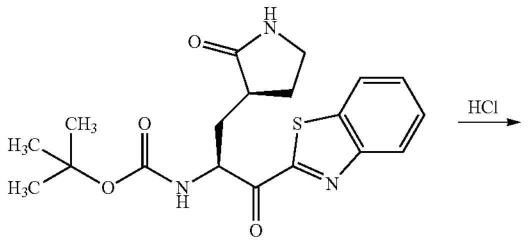

C2

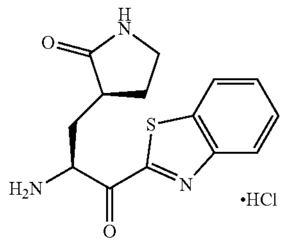

C5

-continued

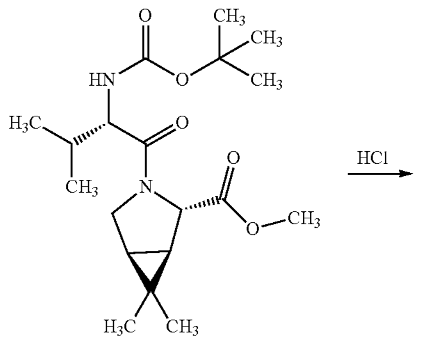

C6

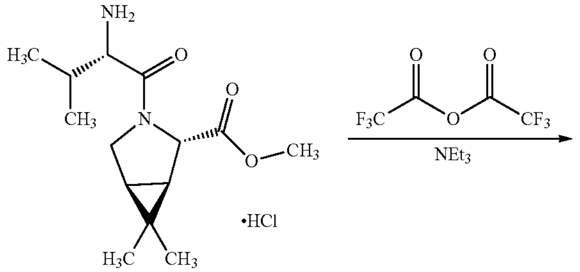

C9

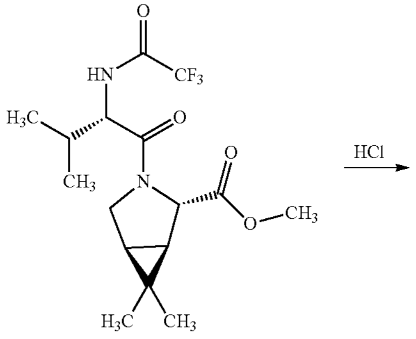

C16

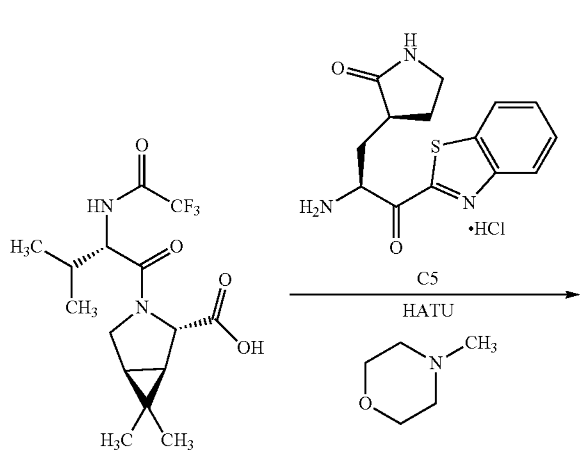

C17

-continued

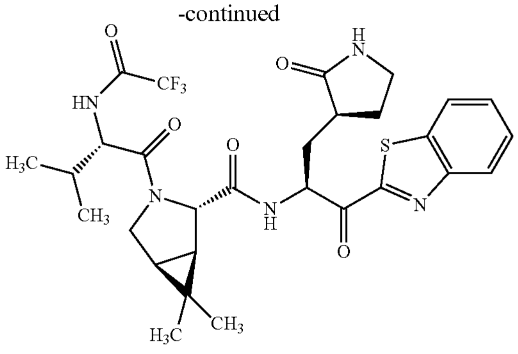

5

Step 1. Synthesis of (3S)-3-[(2S)-2-amino-3-(1,3-benzothiazol-2-yl)-3-oxopropyl]pyrrolidin-2-one, hydrochloride salt (C5)

A solution of C2 (1.5 g, 3.8 mmol) in dichloromethane (26 mL) was treated with a solution of hydrogen chloride in 1,4-dioxane (4 M; 9.6 mL, 38 mmol), followed by methanol (approximately 1 mL) to assist in solubilization. After the reaction mixture had been stirred at room temperature for 1 hour, it was concentrated in vacuo; trituration of the residue with diethyl ether provided C5 as a bright yellow solid. Yield: 1.11 g, 3.41 mmol, 90%. LCMS m/z 290.1 $[M+H]^+$. $^1H$ NMR (400 MHz, methanol-$d_4$) δ 8.30-8.24 (m, 1H), 8.22-8.16 (m, 1H), 7.75-7.64 (m, 2H), 5.34 (dd, J=10.0, 2.3 Hz, 1H), 3.51-3.37 (m, 2H), 3.11-2.98 (m, 1H), 2.56 (ddd, J=15.2, 4.7, 2.3 Hz, 1H), 2.51-2.41 (m, 1H), 2.10-1.89 (m, 2H).

Step 2. Synthesis of methyl (1R,2S,5S)-6,6-dimethyl-3-L-valyl-3-azabicyclo[3.1.0]hexane-2-carboxylate, hydrochloride salt (C9)

A solution of hydrogen chloride in 1,4-dioxane (4 M; 17.3 mL, 69.2 mmol) was added to a solution of C6 (2.55 g, 6.92 mmol) in dichloromethane (28 mL). The reaction mixture was stirred at room temperature for 1.5 hours, whereupon additional hydrogen chloride in 1,4-dioxane (4 M; 3 mL, 12 mmol) was added. After 45 minutes, hydrogen chloride in 1,4-dioxane (4 M; 10 mL, 40 mmol) was again added; 45 minutes later, methanol (5 mL) was added to aid in solubilization. After 30 additional minutes, the reaction mixture was concentrated in vacuo. The residue was triturated with diethyl ether to afford C9 as a white solid (2.39 g). LCMS m/z 269.3 $[M+H]^+$. $^1H$ NMR (400 MHz, methanol-$d_4$) δ 4.45 (s, 1H), 4.06 (d, J=4.9 Hz, 1H), 3.89 (dd, J=10.5, 5.3 Hz, 1H), 3.77-3.72 (m, 1H), 3.75 (s, 3H), 2.36-2.24 (m, 1H), 1.62 (dd, component of ABX system, J=7.5, 5.2 Hz, 1H), 1.55 (d, component of AB quartet, J=7.5 Hz, 1H), 1.16 (d, J=7.0 Hz, 3H), 1.09 (s, 3H), 1.04 (d, J=6.9 Hz, 3H), 1.01 (s, 3H).

Step 3. Synthesis of methyl (1R,2S,5S)-6,6-dimethyl-3-[N-(trifluoroacetyl)-L-valyl]-3-azabicyclo[3.1.0]hexane-2-carboxylate (C16)

Triethylamine (1.55 mL, 11.1 mmol) was added to a 0° C. solution of C9 (1.0 g, 3.3 mmol) in dichloromethane (37 mL), followed by drop-wise addition of trifluoroacetic anhydride (0.57 mL, 4.0 mmol) over 30 minutes. The reaction mixture was stirred at 0° C. for 30 minutes, whereupon it was diluted with dichloromethane (100 mL), washed sequentially with 10% aqueous potassium bisulfate solution (50 mL) and saturated aqueous sodium chloride solution (30 mL), dried over sodium sulfate, filtered, and concentrated in vacuo to provide C16 as a light-yellow oil. Yield: 1.2 g, 3.3 mmol, quantitative. LCMS m/z 365.2 $[M+H]^+$. $^1H$ NMR (400 MHz, chloroform-d) δ 7.04 (br d, J=8.8 Hz, 1H), 4.54 (dd, J=8.9, 6.3 Hz, 1H), 4.46 (s, 1H), 3.91 (dd, J=10.1, 5.0 Hz, 1H), 3.80-3.73 (m, 1H), 3.76 (s, 3H), 2.25-2.13 (m, 1H), 1.55-1.47 (m, 2H), 1.09-1.03 (m, 6H), 0.94 (d, J=6.8 Hz, 3H), 0.92 (s, 3H).

Step 4. Synthesis of (1R,2S,5S)-6,6-dimethyl-3-[N-(trifluoroacetyl)-L-valyl]-3-azabicyclo[3.1.0]hexane-2-carboxylic acid (C17)

Concentrated hydrochloric acid (0.57 mL, 6.6 mmol) was added to a solution of C16 (1.25 g, 3.43 mmol) in a mixture of acetic acid (40.8 mL) and water (8.2 mL). The reaction mixture was heated at 55° C. for 3 days, whereupon it was partitioned between water (50 mL) and ethyl acetate (100 mL). The aqueous layer was extracted with ethyl acetate (2×50 mL), and the combined organic layers were washed with saturated aqueous sodium chloride solution (50 mL), dried over sodium sulfate, filtered, and concentrated in vacuo to afford C17 as a white foam. Yield: 1.00 g, 2.85 mmol, 83%. LCMS m/z 351.2 $[M+H]^+$. $^1H$ NMR (400 MHz, chloroform-d), characteristic peaks: δ 4.56-4.44 (m, 2H), 2.24-2.12 (m, 1H), [1.66 (d, component of AB quartet, J=7.5 Hz) and 1.59-1.47 (m), total 2H], 1.10-1.01 (m, 6H), 0.96-0.91 (m, 6H).

Step 5. Synthesis of (1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[N-(trifluoroacetyl)-L-valyl]-3-azabicyclo[3.1.0]hexane-2-carboxamide (5)

To a 0° C. solution of C17 (1.00 g, 2.85 mmol) in acetonitrile (15 mL) was added C5 (935 mg, 2.87 mmol), followed by O-(7-azabenzotriazol-1-yl)-N,N,N'N'-tetramethyluronium hexafluorophosphate (HATU; 1.20 g, 3.16 mmol). 4-Methylmorpholine (870 mg, 8.60 mmol) was then added drop-wise, and the reaction mixture was allowed to stir and warm slowly to room temperature over 2 hours as the ice bath melted. Volatiles were removed in vacuo, and the residue was dissolved in ethyl acetate (120 mL), washed sequentially with 10% aqueous potassium bisulfate solution (50 mL) and saturated aqueous sodium chloride solution (50 mL), dried over sodium sulfate, filtered, and concentrated in vacuo. Repeated purifications via silica gel chromatography (Gradient: 0% to 10% methanol in dichloromethane; Gradient: 20% to 100% ethyl acetate in heptane; Gradient: 0% to 60% ethyl acetate in dichloromethane) afforded (1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[N-(trifluoroacetyl)-L-valyl]-3-azabicyclo[3.1.0]hexane-2-carboxamide (5) as a white solid. Yield: 390 mg, 0.627 mmol, 22%. LCMS m/z 622.3 $[M+H]^+$. $^1H$ NMR (400 MHz, methanol-$d_4$) δ 9.06 (br d, J=7.8 Hz, 1H), 8.25-8.17 (m, 1H), 8.16-8.08 (m, 1H), 7.68-7.56 (m, 2H), 5.77 (ddd, J=11.4, 7.9, 3.4 Hz, 1H), 4.41 (s, 1H), 4.29 (d, J=9.5 Hz, 1H), 3.97 (d, J=3.1 Hz, 2H), 3.40-3.3 (m, 2H, assumed; partially obscured by solvent peak), 2.90-2.78 (m, 1H), 2.56-2.45 (m, 1H), 2.25-2.03 (m, 4H), 1.57 (dt, J=7.6, 3.1 Hz, 1H), 1.49 (d, component of AB quartet. J=7.7 Hz, 1H), 1.08-1.04 (m, 3H), 1.03 (d, J=6.8 Hz, 3H), 1.00-0.95 (m, 6H).

Example 6 tert-Butyl {(2S)-1-[(1R,2S,5S)-2-({(2S)-1-(1,3-benzothiazol-2-yl)-1-oxo-3-[(3S)-2-oxopyrrolidin-3-yl]propan-2-yl}carbamoyl)-6,6-dimethyl-3-azabicyclo[3.1.0]hexan-3-yl]-3,3-dimethyl-1-oxobutan-2-yl}carbamate (6)

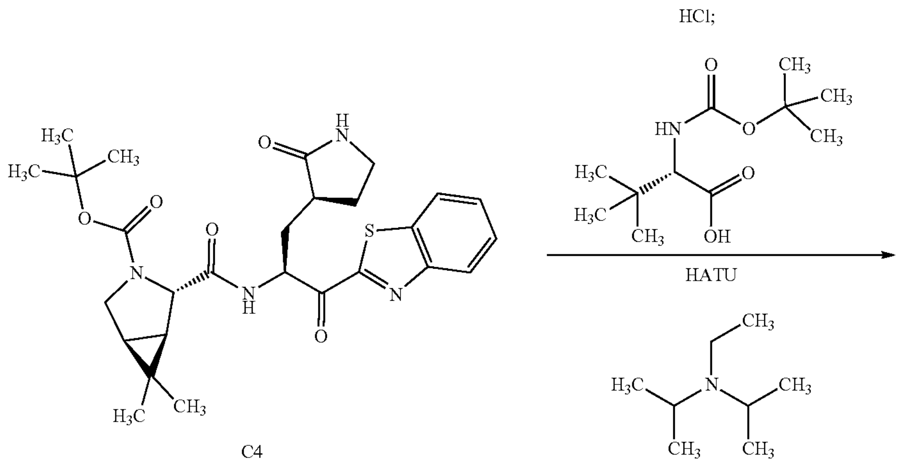

C4

-continued

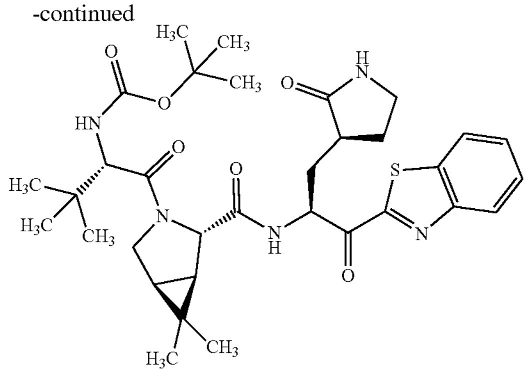

6

A solution of C4 (150 mg, 0.285 mmol) in dichloromethane (2.8 mL) was treated with a solution of hydrogen chloride in 1,4-dioxane (4 M; 0.712 mL, 2.85 mmol), and the reaction mixture was stirred at room temperature for 1 hour. It was then concentrated in vacuo, dissolved in N,N-dimethylformamide (2.5 mL), and cooled to 0° C. In a separate flask, N-(tert-butoxycarbonyl)-3-methyl-L-valine (65.9 mg, 0.285 mmol), 0-(7-azabenzotriazol-1-yl)-N,N, N'N'-tetramethyluronium hexafluorophosphate (HATU; 108 mg, 0.284 mmol), and a drop of N,N-diisopropylethylamine (0.149 mL, 0.855 mmol) in N,N-dimethylformamide (0.5 mL) was stirred at 0° C. for 20 minutes. The solution of deprotected C4 was added drop-wise to the activated N-(tert-butoxycarbonyl)-3-methyl-L-valine solution and the reaction mixture was allowed to warm to room temperature overnight. It was then diluted with ethyl acetate, washed sequentially with 10% aqueous potassium bisulfate solution, 5% aqueous sodium bicarbonate solution, and saturated aqueous sodium chloride solution, dried over sodium sulfate, filtered, and concentrated in vacuo. Silica gel chromatography (Gradient: 0% to 100% ethyl acetate in heptane), followed by further chromatographic purification of mixed fractions (Gradient: 40% to 80% ethyl acetate in heptane) afforded tert-butyl {(2S)-1-[(1R,2S,5S)-2-({(2S)-1-(1,3-benzothiazol-2-yl)-1-oxo-3-[(3S)-2-oxopyrrolidin-3-yl]propan-2-yl}carbamoyl)-6,6-dimethyl-3-azabicyclo[3.1.0]hexan-3-yl]-3,3-dimethyl-1-oxobutan-2-yl}carbamate (6) as a light-yellow solid. Yield: 118 mg, 0.184 mmol, 65%. LCMS m/z 640.3 $[M+H]^+$. $^1H$ NMR (400 MHz, chloroform-d), characteristic peaks: δ 8.18 (d, J=7.8 Hz, 1H), 7.98 (br d, J=7.7 Hz, 1H), [7.66 (br d, J=7.6 Hz) and 7.62-7.50 (m), total 3H], 5.92-5.82 (m, 1H), 5.70-5.55 (m, 1H), 5.26-5.14 (m, 1H), 4.40 (s, 1H), 4.22 (d, J=10.2 Hz, 1H), 3.98 (d, component of AB quartet, J=10.6 Hz, 1H), 3.89 (dd, component of ABX system, J=10.3, 5.3 Hz, 1H), 3.43-3.29 (m, 2H), 2.76-2.65 (m, 1H), 2.65-2.53 (m, 1H), 2.24-2.16 (m, 2H), 1.40 (s, 9H), 1.04 (s, 3H), 1.01 (s, 9H), [0.92 (s) and 0.90 (s), total 3H].

Example 7

(1R,2S,5S)-6,6-Dimethyl-3-[N-(methylsulfonyl)-L-valyl]-N-{(2S)-1-oxo-3-[(3S)-2-oxopyrrolidin-3-yl]-1-[7-(trifluoromethyl)-1,3-benzothiazol-2-yl]propan-2-yl}-3-azabicyclo[3.1.0]hexane-2-carboxamide (7)

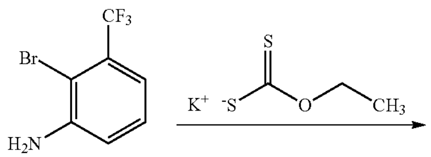

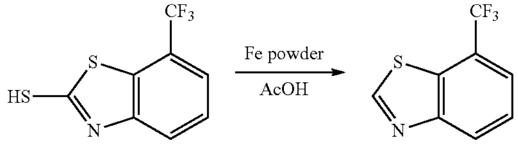

C18 C19

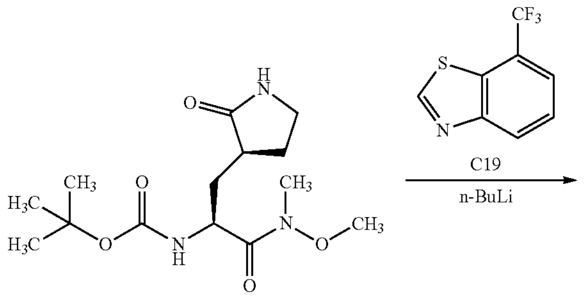

C1

-continued

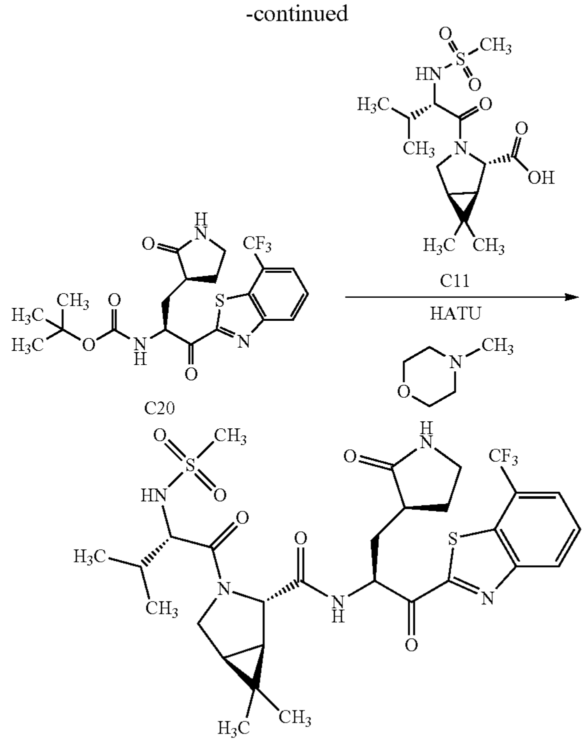

C20

7

Step 1. Synthesis of 7-(trifluoromethyl)-1,3-benzothiazole-2-thiol (C18)

A solution of 2-bromo-3-(trifluoromethyl)aniline (3.00 g, 12.5 mmol) and potassium O-ethyl carbonodithioate (4.41 g, 27.5 mmol) in N,N-dimethylformamide (20 mL) was heated at 120° C. overnight, whereupon it was cooled to room temperature and treated with water (140 mL) and hydrochloric acid (1 M; 30 mL, 30 mmol). The resulting precipitate was isolated via filtration and dissolved in ethyl acetate; the solution was dried over sodium sulfate, filtered, and concentrated in vacuo to afford C18 as a light-pink solid. Yield: 2.97 g, quantitative. LCMS m/z 236.0 $[M+H]^+$. $^1H$ NMR (400 MHz, chloroform-d) δ 10.64 (br s, 1H), 7.55 (d, component of AB quartet, J=7.6 Hz, 1H), 7.48 (dd, J=8.0, 7.7 Hz, 1H), 7.42 (d, component of AB quartet, J=7.9 Hz, 1H).

Step 2. Synthesis of 7-(trifluoromethyl)-1,3-benzothiazole (C19)

Iron powder (7.05 g, 126 mmol) was added portion-wise to a solution of C18 (from the previous step; 2.97 g, 12.5 mmol) in acetic acid (90 mL). After the reaction mixture had been heated at 110° C. for 18 hours, it was cooled and filtered; the filter cake was washed with ethyl acetate, and the combined filtrates were concentrated in vacuo. The residue was dissolved in ethyl acetate (180 mL), washed with saturated aqueous sodium bicarbonate solution (300 mL) and with saturated aqueous sodium chloride solution (300 mL), dried over sodium sulfate, filtered, and concentrated under reduced pressure to afford C19 as a light-yellow solid (3.4 g). A portion of this material was used in the following step. $^1H$ NMR (400 MHz, chloroform-d) δ 9.12 (s, 1H), 8.33 (d, J=8.2 Hz, 1H), 7.77 (d, component of AB quartet, J=7.5 Hz, 1H), 7.65 (dd, J=8, 8 Hz, 1H).

Step 3. Synthesis of tert-butyl {(2S)-1-oxo-3-[(3S)-2-oxopyrrolidin-3-yl]-1-[7-(trifluoromethyl)-1,3-benzothiazol-2-yl]propan-2-yl}carbamate (C20)

n-Butyllithium (2.5 M; 5.86 mL, 14.6 mmol) was added in a drop-wise manner to a −78° C. solution of C19 (from the previous step; 3.4 g, 512.5 mmol) in tetrahydrofuran (33 mL). After 2 hours, a solution of C1 (1.32 g, 4.18 mmol) in tetrahydrofuran (21 mL) was added to the −78° C. reaction mixture, and stirring was continued for 4.5 hours. Saturated aqueous ammonium chloride solution was added, and the resulting mixture was stirred at 0° C. for 20 minutes, whereupon it was diluted with ethyl acetate, washed with water and with saturated aqueous sodium chloride solution, dried over sodium sulfate, filtered, and concentrated in vacuo. Chromatography on silica gel (Gradient: 0% to 100% ethyl acetate in heptane) provided C20 as a yellow solid. Yield: 300 mg, 0.656 mmol, 16%. LCMS m/z 458.3 $[M+H]^+$. $^1H$ NMR (400 MHz, chloroform-d), characteristic peaks: δ 8.42-8.32 (m, 1H), 7.86 (d, J=7.5 Hz, 1H), 7.70 (dd, J=7.9, 7.8 Hz, 1H), 3.45-3.29 (m, 2H), 1.44 (s, 9H).

Step 4. Synthesis of (1R,2S,5S)-6,6-dimethyl-3-[N-(methylsulfonyl)-L-valyl]-N-{(2S)-1-oxo-3-[(3S)-2-oxopyrrolidin-3-yl]-1-[7-(trifluoromethyl)-1,3-benzothiazol-2-yl]propan-2-yl}-3-azabicyclo[3.1.0]hexane-2-carboxamide (7)

A solution of hydrogen chloride in 1,4-dioxane (4 M; 0.11 mL, 0.44 mmol) was added to a solution of C20 (20 mg, 44 μmol) in dichloromethane (0.3 mL). The reaction mixture was stirred at room temperature for 3.25 hours, whereupon it was concentrated in vacuo, dissolved in acetonitrile (0.3 mL), and cooled to 0° C. To this was added C11 (14.5 mg, 43.6 μmol) and O-(7-azabenzotriazol-1-yl)-N,N,N'N'-tetramethyluronium hexafluorophosphate (HATU; 16.6 mg, 43.7 μmol). 4-Methylmorpholine (14.4 μL, 0.131 mmol) was then added drop-wise and the reaction mixture was allowed to stir and warm to room temperature overnight. After the reaction mixture had been concentrated under reduced pressure, it was diluted with ethyl acetate, washed with 10% aqueous potassium bisulfate solution and with saturated aqueous sodium chloride solution, dried over sodium sulfate, filtered, and concentrated in vacuo. Reversed-phase HPLC (Column: Waters Sunfire C18, 19×100 mm, 5 μm; Mobile phase A: water containing 0.05% trifluoroacetic acid (v/v); Mobile phase B: acetonitrile containing 0.05% trifluoroacetic acid (v/v); Gradient: 30% to 70% B over 8.5 minutes, then 70% to 95% B over 0.5 minutes, then 95% B for 1.0 minute; Flow rate: 25 mL/minute) provided (1R,2S,5S)-6,6-dimethyl-3-[N-(methylsulfonyl)-L-valyl]-N-{(2S)-1-oxo-3-[(3S)-2-oxopyrrolidin-3-yl]-1-[7-(trifluoromethyl)-1,3-benzothiazol-2-yl]propan-2-yl}-3-azabicyclo[3.1.0]hexane-2-carboxamide (7). Yield: 4.7 mg, 7.0 μmol, 16%. LCMS m/z 672.6 $[M+H]^+$. Retention time: 3.04 minutes (Analytical conditions. Column: Waters Atlantis C18, 4.6×50 mm, 5 μm; Mobile phase A: water containing 0.05% trifluoroacetic acid (v/v); Mobile phase B: acetonitrile containing 0.05% trifluoroacetic acid (v/v); Gradient: 5% to 95% B over 4.0 minutes, then 95% B for 1.0 minute; Flow rate: 2 mL/minute).

TABLE 1

| Method of synthesis, structure, and physicochemical data for Examples 8-20. | | | |
|---|---|---|---|
| Example Number | Method of synthesis; Non-commercial starting materials | Structure | $^1$H NMR (400 MHz, $CDCl_3$) δ; Mass spectrum, observed ion m/z $[M + H]^+$ or HPLC retention time; Mass spectrum m/z $[M + H]^+$ (unless otherwise indicated) |
| 8 | Example 2; C4 | 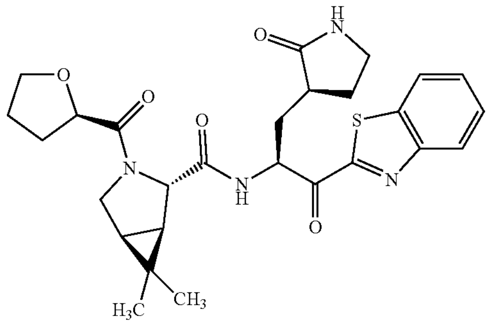 [SMILES: CC1(C)[C@@H]2[C@@H](C(=O)N[C@@H](C[C@@H]3CCNC3=O)C(=O)c3nc4ccccc4s3)N(C(=O)[C@H]3CCCO3)C[C@@H]21] | 2.40 minutes[1]; 525.2 |
| 9 | Example 1; C3 | 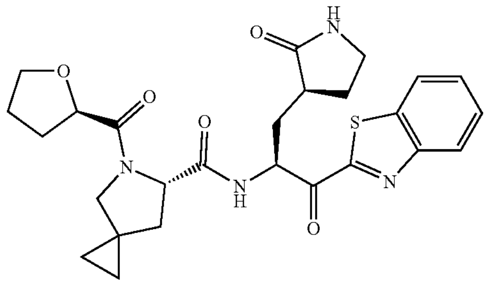 [SMILES: O=C1NCC[C@H]1C[C@H](NC(=O)[C@@H]1CC2(CC2)CN1C(=O)[C@H]1CCCO1)C(=O)c1nc2ccccc2s1] | 2.22 minutes[1]; 511.2 |
| 10 | Example 3; C8 | 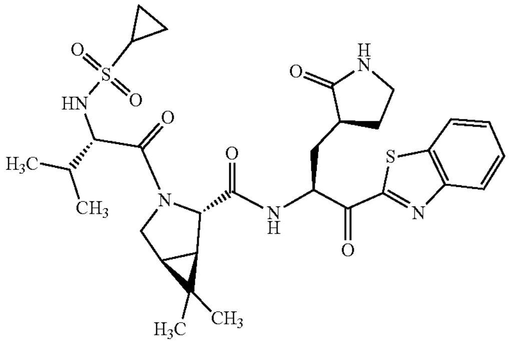 [SMILES: CC(C)[C@H](NS(=O)(=O)C1CC1)C(=O)N1C[C@H]2[C@@H]([C@H]1C(=O)N[C@@H](C[C@@H]1CCNC1=O)C(=O)c1nc3ccccc3s1)C2(C)C] | 2.55 minutes[2]; 630.5 |
| 11 | 6[3] | 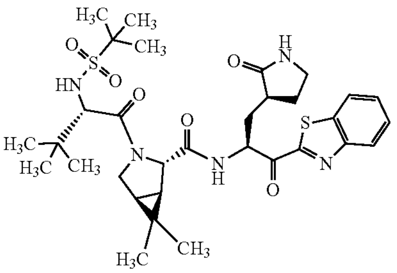 [SMILES: CC(C)(C)[C@H](NS(=O)(=O)C(C)(C)C)C(=O)N1C[C@H]2[C@@H]([C@H]1C(=O)N[C@@H](C[C@@H]1CCNC1=O)C(=O)c1nc3ccccc3s1)C2(C)C] | 3.12 minutes[1]; 660.6 |

TABLE 1-continued
Method of synthesis, structure, and physicochemical data for Examples 8-20.
| Example Number | Method of synthesis; Non-commercial starting materials | Structure | $^1$H NMR (400 MHz, $CDCl_3$) δ; Mass spectrum, observed ion m/z $[M + H]^+$ or HPLC retention time; Mass spectrum m/z $[M + H]^+$ (unless otherwise indicated) |
|---|---|---|---|
| 12 | C15[4] | 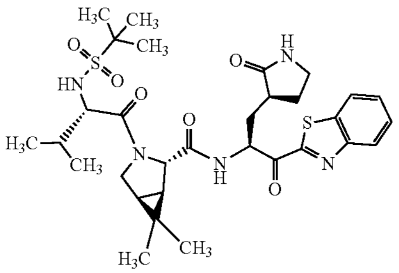 [SMILES: CC(C)[C@H](NS(=O)(=O)C(C)(C)C)C(=O)N1C[C@H]2[C@@H]([C@H]1C(=O)N[C@@H](C[C@@H]1CCNC1=O)C(=O)c1nc3ccccc3s1)C2(C)C] | 3.05 minutes[1]; 646.7 |
| 13 | 6[5] | 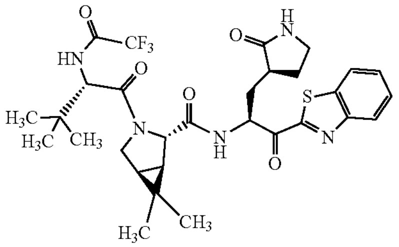 [SMILES: CC(C)(C)[C@H](NC(=O)C(F)(F)F)C(=O)N1C[C@H]2[C@@H]([C@H]1C(=O)N[C@@H](C[C@@H]1CCNC1=O)C(=O)c1nc3ccccc3s1)C2(C)C] | 3.04 minutes[1]; 636.6 |
| 14 | 6[6] | 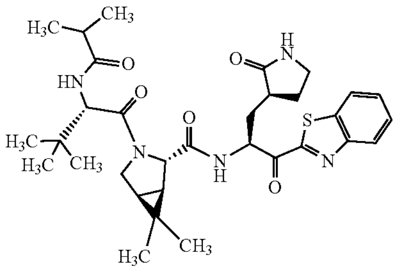 [SMILES: CC(C)C(=O)N[C@H](C(=O)N1C[C@H]2[C@@H]([C@H]1C(=O)N[C@@H](C[C@@H]1CCNC1=O)C(=O)c1nc3ccccc3s1)C2(C)C)C(C)(C)C] | 2.79 minutes[1]; 610.6 |
| 15 | 6[6] | 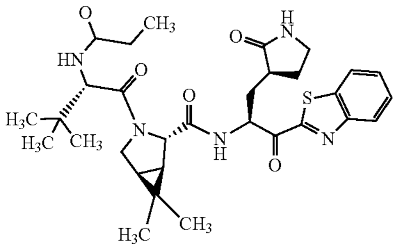 [SMILES: CCC(O)N[C@H](C(=O)N1C[C@H]2[C@@H]([C@H]1C(=O)N[C@@H](C[C@@H]1CCNC1=O)C(=O)c1nc3ccccc3s1)C2(C)C)C(C)(C)C] | 2.69 minutes[1]; 596.6 |

TABLE 1-continued

| Method of synthesis, structure, and physicochemical data for Examples 8-20. | | | |
|---|---|---|---|
| Example Number | Method of synthesis; Non-commercial starting materials | Structure | $^1$H NMR (400 MHz, $CDCl_3$) δ; Mass spectrum, observed ion m/z $[M + H]^+$ or HPLC retention time; Mass spectrum m/z $[M + H]^+$ (unless otherwise indicated) |
| 16 | C15[7] | 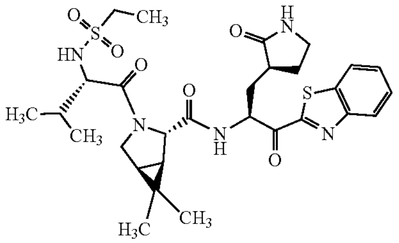 [SMILES: CCS(=O)(=O)N[C@H](C(=O)N1C[C@H]2[C@@H]([C@H]1C(=O)N[C@@H](C[C@@H]1CCNC1=O)C(=O)c1nc3ccccc3s1)C2(C)C)C(C)C] | 2.52 minutes[2]; 618.5 |
| 17 | 6[6] | 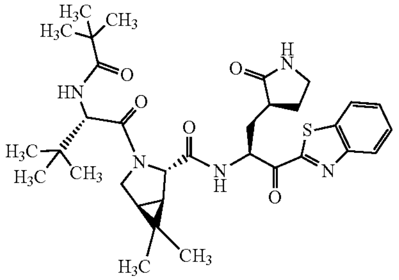 [SMILES: CC(C)(C)C(=O)N[C@H](C(=O)N1C[C@H]2[C@@H]([C@H]1C(=O)N[C@@H](C[C@@H]1CCNC1=O)C(=O)c1nc3ccccc3s1)C2(C)C)C(C)(C)C] | 3.05 minutes[1]; 624.7 |
| 18 | 6[8] | 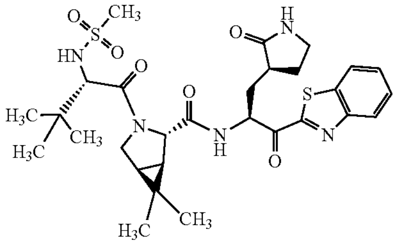 [SMILES: CC(C)(C)[C@H](NS(C)(=O)=O)C(=O)N1C[C@H]2[C@@H]([C@H]1C(=O)N[C@@H](C[C@@H]1CCNC1=O)C(=O)c1nc3ccccc3s1)C2(C)C] | 2.76 minutes[1]; 618.5 |
| 19 | 6[5] | 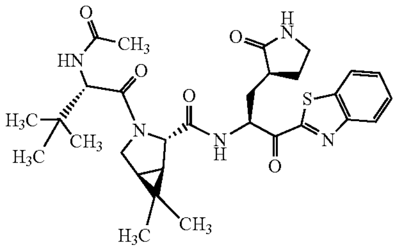 [SMILES: CC(=O)N[C@H](C(=O)N1C[C@H]2[C@@H]([C@H]1C(=O)N[C@@H](C[C@@H]1CCNC1=O)C(=O)c1nc3ccccc3s1)C2(C)C)C(C)(C)C] | 2.61 minutes[1]; 582.5 |
| 20 | Example 1; C2 | 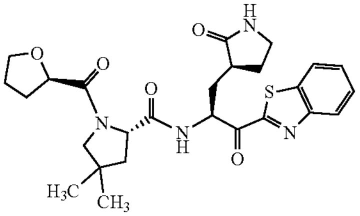 [SMILES: CC1(C)C[C@@H](C(=O)N[C@@H](C[C@@H]2CCNC2=O)C(=O)c2nc3ccccc3s2)N(C(=O)[C@H]2CCCO2)C1] | 2.29 minutes[1]; 513.2 |

1. Conditions for analytical HPLC. Column: Waters Atlantis C18, 4.6×50 mm, 5 μm; Mobile phase A: water containing 0.05% trifluoroacetic acid (v/v); Mobile phase B: acetonitrile containing 0.05% trifluoroacetic acid (v/v); Gradient: 5.0% to 95% B over 4.0 minutes, then 95% B for 1.0 minute; Flow rate: 2 mL/minute.
2. Conditions for analytical HPLC: identical to those in footnote 1, but the analysis was carried out at 60° C.
3. Example 6 was deprotected with hydrogen chloride, and the resulting amine was reacted with 2-methylpropane-2-sulfinyl chloride in the presence of triethylamine to afford (1R,2S,5S)—N-{(2S)-1-(1,3-benzothiazol-2-yl)-1-oxo-3-[(3S)-2-oxopyrrolidin-3-yl]propan-2-yl}-3-[N-(tert-butylsulfinyl)-3-methyl-L-valyl]-6,6-dimethyl-3-azabicyclo[3.1.0]hexane-2-carboxamide. Oxidation with 3-chloroperoxybenzoic acid provided Example 11.
4. Reaction of C15 with 2-methylpropane-2-sulfinyl chloride in the presence of triethylamine provided (1R,2S,5S)—N-{(2S)-1-(1,3-benzothiazol-2-yl)-1-oxo-3-[(3S)-2-oxopyrrolidin-3-yl]propan-2-yl}-3-[N-(tert-butylsulfinyl)-L-valyl]-6,6-dimethyl-3-azabicyclo[3.1.0]hexane-2-carboxamide. Oxidation with 3-chloroperoxybenzoic acid then afforded Example 12.
5. Example 6 was deprotected with hydrogen chloride, and the resulting amine was reacted with the appropriate anhydride, in the presence of triethylamine.
6. Example 6 was deprotected with hydrogen chloride, and the resulting amine was reacted with the appropriate acyl chloride, in the presence of triethylamine.
7. Reaction of C15 with ethanesulfonyl chloride and triethylamine afforded Example 16.
8. Example 6 was deprotected with hydrogen chloride, and the resulting amine was reacted with methanesulfonyl chloride and triethylamine Antiviral Activity from SARS-CoV-2 Infection The ability of compounds to prevent SARS-CoV-2 coronavirus-induced cell death or cytopathic effect can be assessed via cell viability, using an assay format that utilizes luciferase to measure intracellular ATP as an endpoint. In brief, VeroE6 cells that are enriched for hACE2 expression were batched inoculated with SARS-CoV-2 (USA_WA1/2020) at a multiplicity of infection of 0.002 in a BSL-3 lab. Virus-inoculated cells are then added to assay-ready compound plates at a density of 4,000 cells/well. Following a 3-day incubation, a time at which virus-induced cytopathic effect is 95% in the untreated, infected control conditions, cell viability was evaluated using Cell Titer-Glo (Promega), according to the manufacturer's protocol, which quantitates ATP levels. Cytotoxicity of the compounds was assessed in parallel non-infected cells. Test compounds are tested either alone or in the presence of the P-glycoprotein (P-gp) inhibitor CP-100356 at a concentration of 2 μM. The inclusion of CP-100356 is to assess if the test compounds are being effluxed out of the VeroE6 cells, which have high levels of expression of P-glycoprotein. Percent effect at each concentration of test compound was calculated based on the values for the no virus control wells and virus-containing control wells on each assay plate. The concentration required for a 50% response ($EC_{50}$) value was determined from these data using a 4-parameter logistic model. $EC_{50}$ curves were fit to a Hill slope of 3 when >3 and the top dose achieved ≥50% effect. If cytotoxicity was detected at greater than 30% effect, the corresponding concentration data was eliminated from the $EC_{50}$ determination.

For cytotoxicity plates, a percent effect at each concentration of test compound was calculated based on the values for the cell-only control wells and hyamine-containing control wells on each assay plate. The $CC_{50}$ value was calculated using a 4-parameter logistic model. A TI was then calculated by dividing the $CC_{50}$ value by the $EC_{50}$ value.

SARS-CoV-2 Coronavirus 3C Protease FRET Assay and Analysis

The proteolytic activity of the main protease, 3CLpro, of SARS-CoV-2 was monitored using a continuous fluorescence resonance energy transfer (FRET) assay. The SARS-CoV-2 3CLpro assay measures the activity of full length SARS-CoV-2 3CL protease to cleave a synthetic fluorogenic substrate peptide with the following sequence: Dabcyl-KTSAVLQ-SGFRKME-Edans modelled on a consensus peptide (V. Grum-Tokars et al. *Evaluating the 3C-like protease activity of SARS-coronavirus: recommendations for standardized assays for drug discovery. Virus Research* 133 (2008) 63-73). The fluorescence of the cleaved Edans peptide (excitation 340 nm/emission 490 nm) is measured using a fluorescence intensity protocol on a Flexstation reader (Molecular Devices). The fluorescent signal is reduced in the present of PF-835231, a potent inhibitor of SARS-CoV-2 3CLpro. The assay reaction buffer contained 20 mM Tris-HCl (pH 7.3), 100 nM NaCl, 1 mM EDTA and 25 μM peptide substrate. Enzyme reactions were initiated with the addition of 15 nM SARS-CoV-2 3CL protease and allowed to proceed for 60 minutes at 23° C. Percent inhibition or activity was calculated based on control wells containing no compound (0% inhibition/100% activity) and a control compound (100% inhibition/0% activity). $IC_{50}$ values were generated using a four-parameter fit model using ABASE software (IDBS). Ki values were fit to the Morrison equation with the enzyme concentration parameter fixed to 15 nM, the Km parameter fixed to 14 μM and the substrate concentration parameter fixed to 25 μM using ABASE software (IDBS).

Proteolytic activity of SARS-CoV-2 Coronavirus 3CL protease is measured using a continuous fluorescence resonance energy transfer assay. The SARS-CoV-2 $3CL^{pro}$ FRET assay measures the protease catalyzed cleavage of TAMRA-SITSAVLQSGFRKMK-(DABCYL)-OH to TAMRA-SITSAVLQ and SGFRKMK(DABCYL)-OH. The fluorescence of the cleaved TAMRA (ex. 558 nm/em. 581 nm) peptide was measured using a TECAN SAFIRE fluorescence plate reader over the course of 10 min. Typical reaction solutions contained 20 mM HEPES (pH 7.0), 1 mM EDTA, 4.0 μM FRET substrate, 4% DMSO and 0.005% Tween-20. Assays were initiated with the addition of 25 nM SARS $3CL^{pro}$ (nucleotide sequence 9985-10902 of the Urbani strain of SARS coronavirus complete genome sequence (NCBI accession number AY278741)). Percent inhibition was determined in duplicate at 0.001 mM level of inhibitor. Data was analyzed with the non-linear regression analysis program Kalidagraph using the equation:

$$FU=\text{offset}+(\text{limit})(1-e^{-(kobs)t})$$

where offset equals the fluorescence signal of the un-cleaved peptide substrate, and limit equals the fluorescence of fully cleaved peptide substrate. The kobs is the first order rate constant for this reaction, and in the absence of any inhibitor represents the utilization of substrate. In an enzyme start reaction which contains an irreversible inhibitor, and where the calculated limit is less than 20% of the theoretical maximum limit, the calculated kobs represents the rate of inactivation of coronavirus 3C protease. The slope (kobs/I) of a plot of kobs vs. [I] is a measure of the avidity of the inhibitor for an enzyme. For very fast irreversible inhibitors, kobs/I is calculated from observations at only one or two [I] rather than as a slope.

TABLE 2

| Example Number | FRET Assay Geometric Mean $K_i$ (nM) | FRET Assay Count Used $K_i$ (nM) | Antiviral Assay Geometric Mean $EC_{50}$ (μM) | Antiviral Assay Count Used $EC_{50}$ (μM) | IUPAC Name |
|---|---|---|---|---|---|
| Biological activity and IUPAC name for Examples 1-20. | | | | | |
| 1 | 20.2 | 2 | 5.68 | 2 | (6S)-N-{(2S)-1-(1,3-benzothiazol-2-yl)-1-oxo-3-[(3S)-2-oxopyrrolidin-3-yl]propan-2-yl}-5-{(2S)-3-methyl-2-[(methylsulfonyl)amino]butanoyl}-5-azaspiro[2.4]heptane-6-carboxamide |
| 2 | 206 | 1 | ND[1] | | (1R,2S,5S)-N-{(2S)-1-(1,3-benzothiazol-2-yl)-1-oxo-3-[(3S)-2-oxopyrrolidin-3-yl]propan-2-yl}-3-[(4-methoxy-1H-indol-2-yl)carbonyl]-6,6-dimethyl-3-azabicyclo[3.1.0]hexane-2-carboxamide |
| 3 | 10.6 | 1 | 1.21 | 4 | (1R,2S,5S)-N-{(2S)-1-(1,3-benzothiazol-2-yl)-1-oxo-3-[(3S)-2-oxopyrrolidin-3-yl]propan-2-yl}-6,6-dimethyl-3-[N-(methylsulfonyl)-L-valyl]-3-azabicyclo[3.1.0]hexane-2-carboxamide |
| 4 | 7.74 | 1 | ND | | (1R,2S,5S)-6,6-dimethyl-3-[N-(methylsulfonyl)-L-valyl]-N-{(2S)-1-oxo-3-[(3S)-2-oxopyrrolidin-3-yl]-1-[4-(trifluoromethyl)-1,3-benzothiazol-2-yl]propan-2-yl}-3-azabicyclo[3.1.0]hexane-2-carboxamide |
| 5 | 15.2 | 4 | 0.0697 | 6 | (1R,2S,5S)-N-{(2S)-1-(1,3-benzothiazol-2-yl)-1-oxo-3-[(3S)-2-oxopyrrolidin-3-yl]propan-2-yl}-6,6-dimethyl-3-[N-(trifluoroacetyl)-L-valyl]-3-azabicyclo[3.1.0]hexane-2-carboxamide |
| 6 | 137 | 3 | 0.492 | 2 | tert-butyl {(2S)-1-[(1R,2S,5S)-2-({(2S)-1-(1,3-benzothiazol-2-yl)-1-oxo-3-[(3S)-2-oxopyrrolidin-3-yl]propan-2-yl}carbamoyl)-6,6-dimethyl-3-azabicyclo[3.1.0]hexan-3-yl]-3,3-dimethyl-1-oxobutan-2-yl}carbamate |
| 7 | ND | | ND | | (1R,2S,5S)-6,6-dimethyl-3-[N-(methylsulfonyl)-L-valyl]-N-{(2S)-1-oxo-3-[(3S)-2-oxopyrrolidin-3-yl]-1-[7-(trifluoromethyl)-1,3-benzothiazol-2-yl]propan-2-yl}-3-azabicyclo[3.1.0]hexane-2-carboxamide |
| 8 | 6330 | 2 | ND | | (1R,2S,5S)-N-{(2S)-1-(1,3-benzothiazol-2-yl)-1-oxo-3-[(3S)-2-oxopyrrolidin-3-yl]propan-2-yl}-6,6-dimethyl-3-[(2R)-tetrahydrofuran-2-ylcarbonyl]-3-azabicyclo[3.1.0]hexane-2-carboxamide |

TABLE 2-continued

Biological activity and IUPAC name for Examples 1-20.

| Example Number | FRET Assay Geometric Mean $K_i$ (nM) | FRET Assay Count Used $K_i$ (nM) | Antiviral Assay Geometric Mean $EC_{50}$ (μM) | Antiviral Assay Count Used $EC_{50}$ (μM) | IUPAC Name |
|---|---|---|---|---|---|
| 9 | >10000 | 2 | ND | | (6S)-N-{(2S)-1-(1,3-benzothiazol-2-yl)-1-oxo-3-[(3S)-2-oxopyrrolidin-3-yl]propan-2-yl}-5-[(2R)-tetrahydrofuran-2-ylcarbonyl]-5-azaspiro[2.4]heptane-6-carboxamide |
| 10 | 19.6 | 1 | ND | | (1R,2S,5S)-N-{(2S)-1-(1,3-benzothiazol-2-yl)-1-oxo-3-[(3S)-2-oxopyrrolidin-3-yl]propan-2-yl}-3-[N-(cyclopropylsulfonyl)-L-valyl]-6,6-dimethyl-3-azabicyclo[3.1.0]hexane-2-carboxamide |
| 11 | 13.7 | 1 | 0.155 | 2 | (1R,2S,5S)-N-{(2S)-1-(1,3-benzothiazol-2-yl)-1-oxo-3-[(3S)-2-oxopyrrolidin-3-yl]propan-2-yl}-3-[N-(tert-butylsulfonyl)-3-methyl-L-valyl]-6,6-dimethyl-3-azabicyclo[3.1.0]hexane-2-carboxamide |
| 12 | 34.2 | 1 | ND | | (1R,2S,5S)-N-{(2S)-1-(1,3-benzothiazol-2-yl)-1-oxo-3-[(3S)-2-oxopyrrolidin-3-yl]propan-2-yl}-3-[N-(tert-butylsulfonyl)-L-valyl]-6,6-dimethyl-3-azabicyclo[3.1.0]hexane-2-carboxamide |
| 13 | 139 | 1 | ND | | (1R,2S,5S)-N-{(2S)-1-(1,3-benzothiazol-2-yl)-1-oxo-3-[(3S)-2-oxopyrrolidin-3-yl]propan-2-yl}-6,6-dimethyl-3-[3-methyl-N-(trifluoroacetyl)-L-valyl]-3-azabicyclo[3.1.0]hexane-2-carboxamide |
| 14 | 6.02 | 1 | ND | | (1R,2S,5S)-N-{(2S)-1-(1,3-benzothiazol-2-yl)-1-oxo-3-[(3S)-2-oxopyrrolidin-3-yl]propan-2-yl}-6,6-dimethyl-3-[3-methyl-N-(2-methylpropanoyl)-L-valyl]-3-azabicyclo[3.1.0]hexane-2-carboxamide |
| 15 | 6.14 | 1 | ND | | (1R,2S,5S)-N-{(2S)-1-(1,3-benzothiazol-2-yl)-1-oxo-3-[(3S)-2-oxopyrrolidin-3-yl]propan-2-yl}-6,6-dimethyl-3-(3-methyl-N-propanoyl-L-valyl)-3-azabicyclo[3.1.0]hexane-2-carboxamide |
| 16 | 10.3 | 1 | ND | | (1R,2S,5S)-N-{(2S)-1-(1,3-benzothiazol-2-yl)-1-oxo-3-[(3S)-2-oxopyrrolidin-3-yl]propan-2-yl}-3-[N-(ethylsulfonyl)-L-valyl]-6,6-dimethyl-3-azabicyclo[3.1.0]hexane-2-carboxamide |

TABLE 2-continued

| Biological activity and IUPAC name for Examples 1-20. | | | | | |
|---|---|---|---|---|---|
| Example Number | FRET Assay Geometric Mean $K_i$ (nM) | FRET Assay Count Used $K_i$ (nM) | Antiviral Assay Geometric Mean $EC_{50}$ (μM) | Antiviral Assay Count Used $EC_{50}$ (μM) | IUPAC Name |
| 17 | 99.1 | 3 | 0.584 | 2 | (1R,2S,5S)-N-{(2S)-1-(1,3-benzothiazol-2-yl)-1-oxo-3-[(3S)-2-oxopyrrolidin-3-yl]propan-2-yl}-3-[N-(2,2-dimethylpropanoyl)-3-methyl-L-valyl]-6,6-dimethyl-3-azabicyclo[3.1.0]hexane-2-carboxamide |
| 18 | 1.55 | 3 | 0.129 | 2 | (1R,2S,5S)-N-{(2S)-1-(1,3-benzothiazol-2-yl)-1-oxo-3-[(3S)-2-oxopyrrolidin-3-yl]propan-2-yl}-6,6-dimethyl-3-[3-methyl-N-(methylsulfonyl)-L-valyl]-3-azabicyclo[3.1.0]hexane-2-carboxamide |
| 19 | 9.77 | 3 | 1.33 | 2 | (1R,2S,5S)-3-(N-acetyl-3-methyl-L-valyl)-N-{(2S)-1-(1,3-benzothiazol-2-yl)-1-oxo-3-[(3S)-2-oxopyrrolidin-3-yl]propan-2-yl}-6,6-dimethyl-3-azabicyclo[3.1.0]hexane-2-carboxamide |
| 20 | >10800 | 1 | ND | | N-{(2S)-1-(1,3-benzothiazol-2-yl)-1-oxo-3-[(3S)-2-oxopyrrolidin-3-yl]propan-2-yl}-4,4-dimethyl-1-[(2R)-tetrahydrofuran-2-ylcarbonyl]-L-prolinamide |

[1]ND—not determined.

All patents and publications described hereinabove are hereby incorporated by reference in their entirety. While the invention has been described in terms of various preferred embodiments and specific examples, the invention should be understood as not being limited by the foregoing detailed description, but as being defined by the appended claims and their equivalents.

What is claimed is:

1. A compound of Formula I

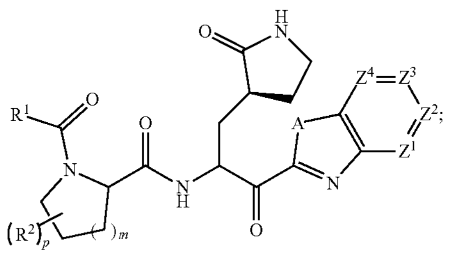

I or a pharmaceutically acceptable salt thereof;

wherein

A is S or O;

$Z^1$, $Z^2$, $Z^3$ and $Z^4$ are each independently $CR^3$ or N;

$R^1$ is selected from the group consisting of $C_1$-$C_6$ alkyl, $R^{1b}$NH—$C_1$-$C_6$ alkyl-, $C_1$-$C_6$ alkoxy, ($C_1$-$C_6$ alkoxy)-$C_1$-$C_6$ alkyl, $C_2$-$C_6$ alkynyl, $C_3$-$C_6$ alkynyloxy, $C_3$-$C_{12}$ cycloalkyl optionally fused with a 5- to 6-membered heteroaryl or phenyl, ($C_3$-$C_{12}$ cycloalkyl)-$C_1$-$C_6$ alkyl, $C_3$-$C_{12}$ cycloalkoxy, ($C_3$-$C_{12}$ cycloalkoxy)-$C_1$-$C_6$ alkyl, 4- to 12-membered heterocycloalkyl which is optionally fused with a 5- to 6-membered heteroaryl or phenyl and wherein said heterocycloalkyl comprises one to four heteroatoms independently selected from N, O and $S(O)_n$, (4- to 12-membered heterocycloalkyl)-$C_1$-$C_6$ alkyl wherein said heterocycloalkyl moiety comprises one to four heteroatoms independently selected from N, O and $S(O)_n$, $C_6$-$C_{10}$ aryl optionally fused with a $C_4$-$C_6$ cycloalkyl or a 4- to 7-membered heterocycloalkyl, ($C_6$-$C_{10}$ aryl)-$C_1$-$C_6$ alkyl, 5- to 10-membered heteroaryl comprising one to five heteroatoms independently selected from N, O and S, (5- to 10-membered heteroaryl)-$C_1$-$C_6$ alkyl wherein the heteroaryl moiety comprises one to five heteroatoms independently selected from N, O and S, (5- to 10-membered heteroaryloxy)-$C_1$-$C_6$ alkyl wherein the heteroaryl moiety comprises one to five heteroatoms independently selected from N, O and S, (5- to 6-membered heteroaryl)-(5- to 6-membered heteroaryl)- wherein each heteroaryl moiety comprises one to four heteroatoms independently selected from N, O and S, (4- to 7-membered heterocycloalkyl)-(5- to 6-membered heteroaryl)- wherein the heterocycloalkyl moiety comprises one to three heteroatoms independently selected from N, O and $S(O)_n$ and the heteroaryl moiety comprises one to four heteroatoms independently selected from N, O and S, and (5- to 6-membered heteroaryl)-(4- to 7-membered heterocycloalkyl)- wherein the heterocycloalkyl moiety comprises one to three heteroatoms independently selected from N, O and $S(O)_n$ and the heteroaryl moiety comprises one to four heteroatoms independently selected from N, O and S; wherein each $R^1$ group is optionally substituted with one to five $R^{1a}$;

$R^{1a}$ at each occurrence is independently selected from the group consisting of oxo, halo, hydroxy, cyano, phenyl, amino, ($C_1$-$C_3$ alkyl)amino, di($C_1$-$C_3$ alkyl)amino, $C_1$-$C_6$ alkyl optionally substituted with one to five fluoro, $C_1$-$C_6$ alkoxy optionally substituted with one to five fluoro, ($C_1$-$C_3$ alkoxy)-$C_1$-$C_3$ alkyl optionally substituted with one to five fluoro, $C_3$-$C_6$ cycloalkyl optionally substituted with one to three substituents independently selected from fluoro and $C_1$-$C_3$ alkyl, $C_3$-$C_6$ cycloalkyl-$C_1$-$C_6$ alkyl, phenyl, phenyl-$C_1$-$C_6$ alkyl, ($C_1$-$C_6$ alkyl)-C(O)— and ($C_1$-$C_6$ alkyl)-$S(O)_n$—;

$R^{1b}$ is selected from the group consisting of $C_1$-$C_6$ alkyl-C(O)—, $C_3$-$C_6$ cycloalkyl-C(O)—, $C_1$-$C_6$ alkyl-OC(O)—, $C_3$-$C_6$ cycloalkyl-OC(O)—, $(C_1$-$C_6$ alkyl$)_2$N—C(O)—, $(C_1$-$C_6$ alkyl$)_2$N—($C_1$-$C_6$ alkyl)-C(O)—, ($C_1$-$C_6$ alkyl)-$S(O)_2$—, ($C_3$-$C_6$ cycloalkyl)-$S(O)_2$—, (4- to 7-membered heterocycloalkyl)-OC(O)— wherein the heterocycloalkyl moiety comprises one to three heteroatoms independently selected from N, O and $S(O)_n$, and 5- to 6-membered heteroaryl comprising one to three heteroatoms independently selected from N, O and S; wherein each $R^{1b}$ group is optionally substituted with one to five fluoro or with one to two $C_1$-$C_3$ alkyl;

$R^2$ at each occurrence is independently selected from the group consisting of fluoro, $C_1$-$C_6$ alkyl optionally substituted with one to three fluoro, and $C_1$-$C_6$ alkoxy optionally substituted with one to three fluoro; or two $R^2$ groups when attached to adjacent carbons and taken together with the carbons to which they are attached are a fused $C_3$-$C_6$ cycloalkyl which is optionally substituted with one to four $R^{2a}$; or two $R^2$ groups when attached to the same carbon and taken together with the carbon to which they are attached are a spiro $C_3$-$C_6$ cycloalkyl which is optionally substituted with one to four $R^{2a}$;

$R^{2a}$ at each occurrence is independently selected from fluoro, $C_1$-$C_3$ alkyl optionally substituted with one to five fluoro and $C_1$-$C_8$alkoxy optionally substituted with one to five fluoro;

$R^3$ at each occurrence is independently selected from hydrogen, halo, cyano, $C_1$-$C_6$ alkyl optionally substituted with one to five fluoro, $C_1$-$C_6$ alkoxy optionally substituted with one to five fluoro, and ($C_1$-$C_6$ alkyl)-$SO_2$—;

m is 1 or 2;

n at each occurrence is independently selected from 0, 1 and 2; and p is 0, 1, 2, 3 or 4.

2. The compound of claim 1 wherein $R^2$ at each occurrence is independently selected from the group consisting of fluoro, methyl, ethyl, isopropyl, tert-butyl, trifluoromethyl and tert-butoxy; or two $R^2$ groups when attached to adjacent carbons and taken together with the carbons to which they are attached are a fused cyclohexane, cyclopentane or cyclopropane ring which is optionally substituted with one to four $R^{2a}$; or two $R^2$ groups when attached to the same carbon and taken together with the carbon to which they are attached are a spirocyclopropane, spirocyclobutane, spirocyclopentane or spirocyclohexane ring which is optionally substituted with one to four $R^{2a}$;

or a pharmaceutically acceptable salt thereof.

3. The compound of claim 2 wherein $R^{2a}$ at each occurrence is independently selected from the group consisting of fluoro, methyl, trifluoromethyl and methoxy;

or a pharmaceutically acceptable salt thereof.

4. The compound of claim 1 wherein m is 1 and the moiety

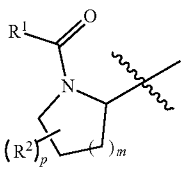

is selected from the group consisting of

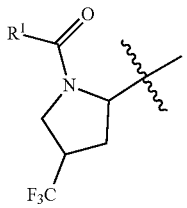
,
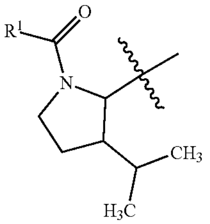
,
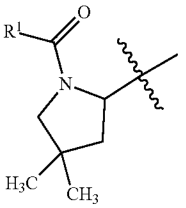
,
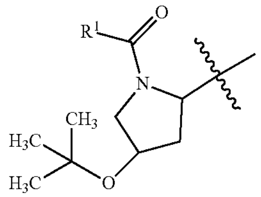
,
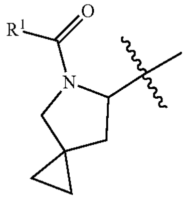
,
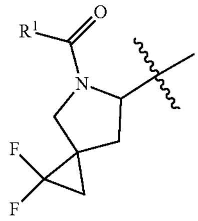
,
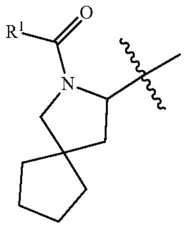
,
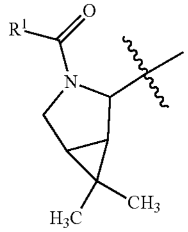
,
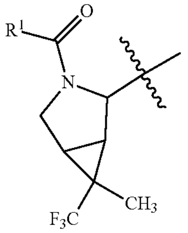
,
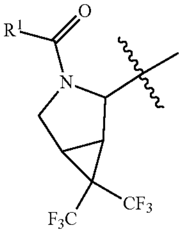
,
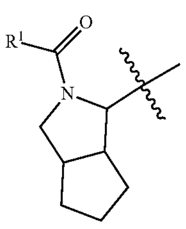
, and
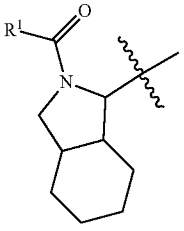
;

or a pharmaceutically acceptable salt thereof.

5. The compound of claim 1 wherein m is 2 and the moiety is selected from the group consisting of

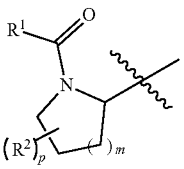, 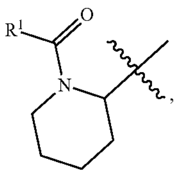, 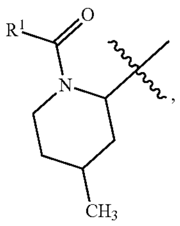, 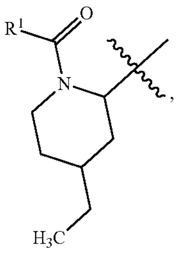, 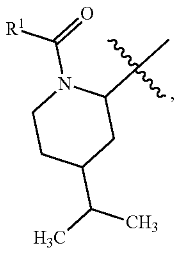, and 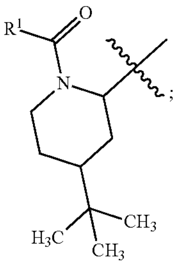;

or a pharmaceutically acceptable salt thereof.

6. The compound of claim 1 wherein the moiety

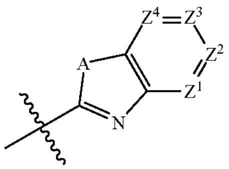

is selected from the group consisting of

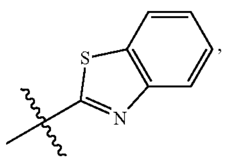, 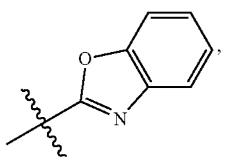, 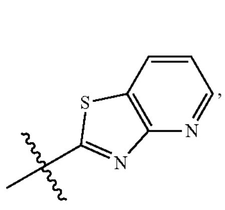, 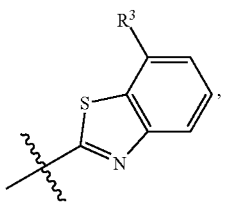,

-continued

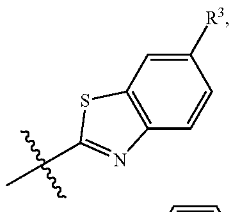, 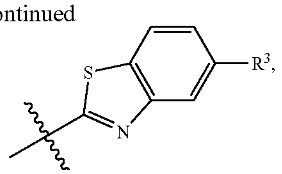, 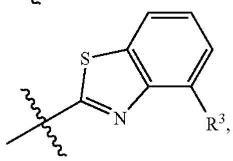, 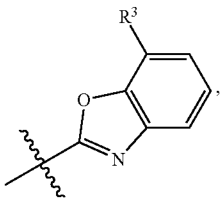, 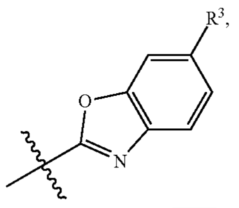, 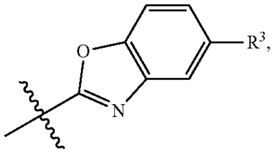, 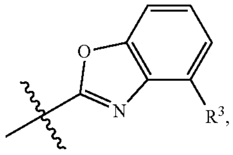, 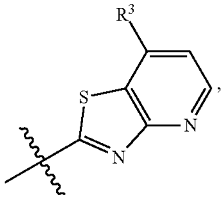, 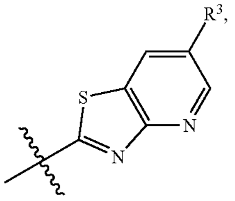, and 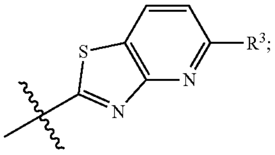;

and $R^3$ is selected from the group consisting of halo, cyano, $C_1$-$C_6$ alkyl optionally substituted with one to five fluoro, $C_1$-$C_6$ alkoxy optionally substituted with one to five fluoro, and ($C_1$-$C_6$ alkyl)-$SO_2$—;

or a pharmaceutically acceptable salt thereof.

7. The compound of claim 6 wherein $R^3$ is selected from the group consisting of chloro, cyano, methyl, trifluoromethyl, tert-butyl, methoxy and methylsulfonyl;

or a pharmaceutically acceptable salt thereof.

8. The compound of claim 1 wherein $R^1$ is a 4- to 12-membered heterocycloalkyl which is optionally fused with a 5- to 6-membered heteroaryl or phenyl and wherein said heterocycloalkyl comprises one to four heteroatoms independently selected from N, O and $S(O)_n$, or is a (4- to 12-membered heterocycloalkyl)-$C_1$-$C_6$ alkyl wherein said heterocycloalkyl moiety comprises one to four heteroatoms independently selected from N, O and $S(O)_n$; each of which is optionally substituted with one to five $R^{1a}$, or a pharmaceutically acceptable salt thereof.

9. The compound of claim 8 wherein the 4- to 12-membered heterocycloalkyl moiety in $R^1$ is selected from the group consisting of azetidinyl, pyrrolidinyl, piperidinyl, piperazinyl, morpholinyl, oxetanyl, tetrahydrofuranyl, pyranyl, 2-oxo-1,3-oxazolidinyl, oxabicyclo[2.2.1]heptyl, 1-oxa-8-azaspiro[4.5]decyl, 1,1-dioxido-1,2-thiazolidinyl and 1,1-dioxido-1,2-thiazinanyl; each of which is optionally substituted with one to three $R^{1a}$; or a pharmaceutically acceptable salt thereof.

10. The compound of claim 9 wherein $R^1$ is a 4- to 12-membered heterocycloalkyl selected from

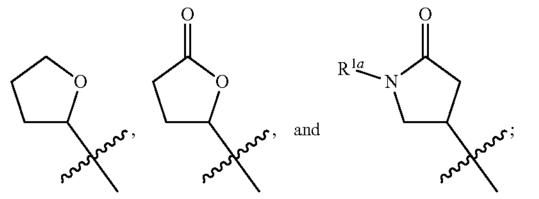

and or a pharmaceutically acceptable salt thereof.

11. The compound of claim 1 wherein $R^1$ is selected from the group consisting of phenyl, a 5- to 10-membered heteroaryl comprising one to five heteroatoms independently selected from N, O and S; a (5- to 10-membered heteroaryl)-$C_1$-$C_6$ alkyl wherein the heteroaryl moiety comprises one to five heteroatoms independently selected from N, O and S; and a (5- to 10-membered heteroaryloxy)-$C_1$-$C_6$ alkyl wherein the heteroaryl moiety comprises one to five heteroatoms independently selected from N, O and S; each of which is optionally substituted with one to five $R^{1a}$; or a pharmaceutically acceptable salt thereof.

12. The compound of claim 11 wherein the 5- to 10-membered heteroaryl moiety in $R^1$ is selected from the group consisting of imidazolyl, pyrazolyl, oxazolyl, isoxazolyl, thiazolyl, isothiazolyl, oxadiazolyl, triazolyl, pyridinyl, pyrimidinyl, pyrazinyl, pyridazinyl, indolyl, quinolinyl, quinoxalinyl, benzotriazolyl, imidazo[1,2-a]pyridinyl, imidazo[2,1-b][1,3]thiazolyl, [1,2,4]triazolo[1,5-a]pyrimidinyl, [1,2,3]triazolo[1,5-a]pyridinyl and naphthyridinyl; each of which is optionally substituted with one to three $R^{1a}$; provided that when $R^1$ is triazolyl, oxazolyl, isoxazolyl, thiazolyl or isothiazolyl then $R^1$ is optionally substituted with one to two $R^{1a}$ and when $R^1$ is oxadiazolyl then $R^1$ is optionally substituted with one $R^{1a}$;

or a pharmaceutically acceptable salt thereof.

13. The compound of claim 12 wherein $R^1$ is selected from the group consisting of indolyl, isoxazolyl, thiazolylmethyl, pyrazolyl, pyrazolylmethyl, triazolyl and triazolylmethyl; each of which is optionally substituted with one to three $R^{1a}$, provided that when $R^1$ is isoxazolyl, thiazolyl, triazolyl, thiazolylmethyl or triazolylmethyl then $R^1$ is optionally substituted with one to two $R^{1a}$; or a pharmaceutically acceptable salt thereof.

14. The compound of claim 1 wherein $R^1$ is $R^{1b}NH$—$C_1$-$C_6$ alkyl-; or a pharmaceutically acceptable salt thereof.

15. The compound of claim 14 wherein $R^{1b}NH$—$C_1$-$C_6$ alkyl- is selected from

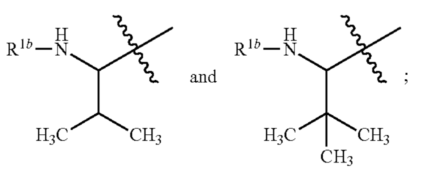

and or a pharmaceutically acceptable salt thereof.

16. The compound of claim 15 wherein $R^{1b}$ is selected from the group consisting of $CH_3C(O)$—, $CF_3C(O)$—, $CH_3CH_2C(O)$—, $(CH_3)_2CHC(O)$—, $(CH_3)_3CC(O)$—, cyclopropyl-C(O)—, (3,3-difluorocyclobutyl)-C(O)—, $(CH_3)_2N$—C(O)—, $(CH_3)_2N$—$CH_2C(O)$—, $CH_3OC(O)$—, $CH_3CH_2OC(O)$—, $(CH_3)_2CHOC(O)$—, $(CH_3)_3COC(O)$—, (1-methylazetidin-3-yl)-OC(O)—, $CH_3S(O)_2$—, $CH_3CH_2S(O)_2$—, $(CH_3)_2CHS(O)_2$—, $(CH_3)_3CS(O)_2$— and (cyclopropyl)-$S(O)_2$—;

or a pharmaceutically acceptable salt thereof.

17. The compound of claim 1 selected from the group consisting of (6S)—N-{(2R)-1-(1,3-benzothiazol-2-yl)-1-oxo-3-[(3S)-2-oxopyrrolidin-3-yl]propan-2-yl}-5-[(2R)-tetrahydrofuran-2-ylcarbonyl]-5-azaspiro[2.4]heptane-6-carboxamide;

N-{(2S)-1-(1,3-benzothiazol-2-yl)-1-oxo-3-[(3S)-2-oxopyrrolidin-3-yl]propan-2-yl}-4,4-dimethyl-1-[(2R)-tetrahydrofuran-2-ylcarbonyl]-L-prolinamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[(2R)-tetrahydrofuran-2-ylcarbonyl]-3-azabicyclo[3.1.0]hexane-2-carboxamide;

tert-butyl (1R,2S,5S)-2-({(2S)-1-(1,3-benzothiazol-2-yl)-1-oxo-3-[(3S)-2-oxopyrrolidin-3-yl]propan-2-yl}carbamoyl)-6,6-dimethyl-3-azabicyclo[3.1.0]hexane-3-carboxylate;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-{[(2R)-5-oxotetrahydrofuran-2-yl]carbonyl}-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-{[(3R)-1-methyl-5-oxopyrrolidin-3-yl]carbonyl}-3-azabicyclo[3.1.0]hexane-2-carboxamide;

N-acetyl-L-valyl-N-{(2S)-1-(1,3-benzothiazol-2-yl)-1-oxo-3-[(3S)-2-oxopyrrolidin-3-yl]propan-2-yl}-4,4-dimethyl-L-prolinamide;

N-(methoxycarbonyl)-L-valyl-N-{(2S)-1-(1,3-benzothiazol-2-yl)-1-oxo-3-[(3S)-2-oxopyrrolidin-3-yl]propan-2-yl}-4,4-dimethyl-L-prolinamide;

(2S)—N-{(2S)-1-(1,3-benzothiazol-2-yl)-1-oxo-3-[(3S)-2-oxopyrrolidin-3-yl]propan-2-yl}-1-[N-(methylsulfonyl)-L-valyl]piperidine-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-{[(3R)-5-oxo-1-(propan-2-yl) pyrrolidin-3-yl]carbonyl}-3-azabicyclo[3.1.0]hexane-2-carboxamide;

(1R,2S,5S)-3-(N-acetyl-3-methyl-L-valyl)-N-{(2S)-1-(1,3-benzothiazol-2-yl)-1-oxo-3-[(3S)-2-oxopyrrolidin-3-yl]propan-2-yl}-6,6-dimethyl-3-azabicyclo[3.1.0]hexane-2-carboxamide;

N-(cyclopropylcarbonyl)-L-valyl-N-{(2S)-1-(1,3-benzothiazol-2-yl)-1-oxo-3-[(3S)-2-oxopyrrolidin-3-yl]propan-2-yl}-4,4-dimethyl-L-prolinamide;

(6S)—N-{(2S)-1-(1,3-benzothiazol-2-yl)-1-oxo-3-[(3S)-2-oxopyrrolidin-3-yl]propan-2-yl}-5-{(2S)-3-methyl-2-[(methylsulfonyl)amino]butanoyl}-5-azaspiro[2.4]heptane-6-carboxamide;

(1R,2S,5S)—N-{(2S)-1-(1,3-benzothiazol-2-yl)-1-oxo-3-[(3S)-2-oxopyrrolidin-3-yl]propan-2-yl}-3-{[(3R)-1-(cyclopropylmethyl)-5-oxopyrrolidin-3-yl]carbonyl}-6,6-dimethyl-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-{[(3R)-1- cyclobutyl-5-oxopyrrolidin-3-yl]carbonyl}-6,6-dimethyl-3-azabicyclo[3.1.0]hexane-2-carboxamide;

(2S,4R)—N-{(2S)-1-(1,3-benzothiazol-2-yl)-1-oxo-3-[(3S)-2-oxopyrrolidin-3-yl]propan-2-yl}-4-methyl-1-[N-(methylsulfonyl)-L-valyl]piperidine-2-carboxamide;

(2S,4S)—N-{(2S)-1-(1,3-benzothiazol-2-yl)-1-oxo-3-[(3S)-2-oxopyrrolidin-3-yl]propan-2-yl}-4-methyl-1-[N-(methylsulfonyl)-L-valyl]piperidine-2-carboxamide;

N-(methylsulfonyl)-L-valyl-N-{(2S)-1-(1,3-benzothiazol-2-yl)-1-oxo-3-[(3S)-2-oxopyrrolidin-3-yl]propan-2-yl}-4,4-dimethyl-L-prolinamide;

(2S,4R)—N-{(2S)-1-(1,3-benzoxazol-2-yl)-1-oxo-3-[(3S)-2-oxopyrrolidin-3-yl]propan-2-yl}-4-methyl-1-[N-(trifluoroacetyl)-L-valyl]piperidine-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-{[(3R)-1-tert-butyl-5-oxopyrrolidin-3-yl]carbonyl}-6,6-dimethyl-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-(3-methyl-N-propanoyl-L-valyl)-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[N-(methylsulfonyl)-L-valyl]-3-azabicyclo[3.1.0]hexane-2-carboxamide;

(1S,3aR,6aS)—N-{(2S)-1-(1,3-benzothiazol-2-yl)-1-oxo-3-[(3S)-2-oxopyrrolidin-3-yl]propan-2-yl}-2-{(2S)-3-methyl-2-[(methylsulfonyl)amino]butanoyl}octahydro cyclopenta[c]pyrrole-1-carboxamide;

(1R,2S,5S)—N-{(2S)-1-(1,3-benzoxazol-2-yl)-1-oxo-3-[(3S)-2-oxopyrrolidin-3-yl]propan-2-yl}-6,6-dimethyl-3-[N-(trifluoroacetyl)-L-valyl]-3-azabicyclo[3.1.0]hexane-2-carboxamide;

(2S,4S)—N-{(2S)-1-(1,3-benzothiazol-2-yl)-1-oxo-3-[(3S)-2-oxopyrrolidin-3-yl]propan-2-yl}-4-ethyl-1-[N-(methylsulfonyl)-L-valyl]piperidine-2-carboxamide;

(2S,4R)—N-{(2S)-1-(1,3-benzothiazol-2-yl)-1-oxo-3-[(3S)-2-oxopyrrolidin-3-yl]propan-2-yl}-4-ethyl-1-[N-(methylsulfonyl)-L-valyl]piperidine-2-carboxamide;

N-(methylsulfonyl)-L-valyl-(3R)—N-{(2S)-1-(1,3-benzothiazol-2-yl)-1-oxo-3-[(3S)-2-oxopyrrolidin-3-yl]propan-2-yl}-3-propan-2-yl-L-prolinamide;

(1R,2S,5S)—N-{(2S)-1-(1,3-benzothiazol-2-yl)-1-oxo-3-[(3S)-2-oxopyrrolidin-3-yl]propan-2-yl}-3-[N-(cyclopropylcarbonyl)-3-methyl-L-valyl]-6,6-dimethyl-3-azabicyclo[3.1.0]hexane-2-carboxamide;

(2S,4R)—N-{(2S)-1-(1,3-benzothiazol-2-yl)-1-oxo-3-[(3S)-2-oxopyrrolidin-3-yl]propan-2-yl}-4-methyl-1-[N-(trifluoroacetyl)-L-valyl]piperidine-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[3-methyl-N-(2-methylpropanoyl)-L-valyl]-3-azabicyclo[3.1.0]hexane-2-carboxamide;

(2S)—N-{(2S)-1-(1,3-benzothiazol-2-yl)-1-oxo-3-[(3S)-2-oxopyrrolidin-3-yl]propan-2-yl}-4-methyl-2-{7-[(methylsulfonyl)amino]-1-oxo-1,3-dihydro-2H-isoindol-2-yl}pentanamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-{[(3R)-5-oxo-1-phenylpyrrolidin-3-yl]carbonyl}-3-azabicyclo[3.1.0]hexane-2-carboxamide;

tert-butyl {(2S)-1-[(2S,4R)-2-({(2S)-1-(1,3-benzothiazol-2-yl)-1-oxo-3-[(3S)-2-oxopyrrolidin-3-yl]propan-2-yl}carbamoyl)-4-methylpiperidin-1-yl]-3-methyl-1-oxobutan-2-yl}carbamate;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[3-methyl-N-(methylsulfonyl)-L-valyl]-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-[N-(ethylsulfonyl)-L-valyl]-6,6-dimethyl-3-azabicyclo[3.1.0]hexane-2-carboxamide;

(3S)—N-{(2S)-1-(1,3-benzothiazol-2-yl)-1-oxo-3-[(3S)-2-oxopyrrolidin-3-yl]propan-2-yl}-2-{(2S)-3-methyl-2-[(methylsulfonyl)amino]butanoyl}-2-azaspiro[4.4]nonane-3-carboxamide;

(1S,3aR,7aS)—N-{(2S)-1-(1,3-benzothiazol-2-yl)-1-oxo-3-[(3S)-2-oxopyrrolidin-3-yl]propan-2-yl}-2-{(2S)-3-methyl-2-[(methylsulfonyl)amino]butanoyl}octahydro-1H-isoindole-1-carboxamide;

(2S,4S)—N-{(2S)-1-(1,3-benzothiazol-2-yl)-1-oxo-3-[(3S)-2-oxopyrrolidin-3-yl]propan-2-yl}-1-[N-(methylsulfonyl)-L-valyl]-4-(propan-2-yl) piperidine-2-carboxamide;

(2S,4R)—N-{(2S)-1-(1,3-benzothiazol-2-yl)-1-oxo-3-[(3S)-2-oxopyrrolidin-3-yl]propan-2-yl}-1-[N-(methylsulfonyl)-L-valyl]-4-(propan-2-yl) piperidine-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[N-(trifluoroacetyl)-L-valyl]-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-{N-[(2S)-1, 1,1-trifluoropropan-2-yl]-L-valyl}-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-[N-(2,2-dimethylpropanoyl)-3-methyl-L-valyl]-6,6-dimethyl-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-{[(3R)-1-benzyl-5-oxopyrrolidin-3-yl]carbonyl}-6,6-dimethyl-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-[N-(cyclopropylsulfonyl)-L-valyl]-6,6-dimethyl-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[N-(propan-2-ylsulfonyl)-D-valyl]-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[N-(propan-2-ylsulfonyl)-L-valyl]-3-azabicyclo[3.1.0]hexane-2-carboxamide;

(2S,4S)—N-{(2S)-1-(1,3-benzothiazol-2-yl)-1-oxo-3-[(3S)-2-oxopyrrolidin-3-yl]propan-2-yl}-4-tert-butyl-1-[N-(methylsulfonyl)-L-valyl]piperidine-2-carboxamide;

(2S,4R)—N-{(2S)-1-(1,3-benzothiazol-2-yl)-1-oxo-3-[(3S)-2-oxopyrrolidin-3-yl]propan-2-yl}-4-tert-butyl-1-[N-(methylsulfonyl)-L-valyl]piperidine-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl- 3-[3-methyl-N-(trifluoroacetyl)-L-valyl]-3-azabicyclo[3.1.0]hexane-2-carboxamide;

N-(methylsulfonyl)-L-valyl-(4R)—N-{(2S)-1-(1,3-benzothiazol-2-yl)-1-oxo-3-[(3S)-2-oxopyrrolidin-3-yl]propan-2-yl}-4-tert-butoxy-L-prolinamide;

tert-butyl {(2S)-1-[(1R,2S,5S)-2-({(2S)-1-(1,3-benzothiazol-2-yl)-1-oxo-3-[(3S)-2-oxopyrrolidin-3-yl]propan-2-yl}carbamoyl)-6,6-dimethyl-3-azabicyclo[3.1.0]hex-3-yl]-3,3-dimethyl-1-oxobutan-2-yl}carbamate;

(1R,2S,5S)—N-{(2S)-1-(4-chloro-1,3-benzoxazol-2-yl)-1-oxo-3-[(3S)-2-oxopyrrolidin-3-yl]propan-2-yl}-6,6-dimethyl-3-[N-(trifluoroacetyl)-L-valyl]-3-azabicyclo[3.1.0]hexane-2-carboxamide;

(2S,4S)-4-methyl-1-[N-(methylsulfonyl)-L-valyl]-N-{(2S)-1-oxo-3-[(3S)-2-oxopyrrolidin-3-yl]-1-[4-(trifluoromethyl)-1,3-benzoxazol-2-yl]propan-2-yl}piperidine-2-carboxamide;

(2S,4R)-4-methyl-1-[N-(methylsulfonyl)-L-valyl]-N-{(2S)-1-oxo-3-[(3S)-2-oxopyrrolidin-3-yl]-1-[4-(trifluoromethyl)-1,3-benzoxazol-2-yl]propan-2-yl}piperidine-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-[N-(cyclopropylsulfonyl)-3-methyl-L-valyl]-6,6-dimethyl-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-[N-(tert-butylsulfonyl)-L-valyl]-6,6-dimethyl-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[3-methyl-N-(propan-2-ylsulfonyl)-L-valyl]-3-azabicyclo[3.1.0]hexane-2-carboxamide;

methyl {(2S)-1-[(1R,2S,5S)-6,6-dimethyl-2-({(2S)-1-oxo-3-[(3S)-2-oxopyrrolidin-3-yl]-1-[4-(trifluoromethyl)-1,3-benzoxazol-2-yl]propan-2-yl}carbamoyl)-3-azabicyclo[3.1.0]hex-3-yl]-3,3-dimethyl-1-oxobutan-2-yl}carbamate;

(2S)—N-{(2S)-1-(1,3-benzothiazol-2-yl)-1-oxo-3-[(3S)-2-oxopyrrolidin-3-yl]propan-2-yl}-6-methyl-3-[N-(methylsulfonyl)-L-valyl]-6-(trifluoromethyl)-3-azabicyclo[3.1.0]hexane-2-carboxamide;

(2S,4R)-4-methyl-1-[N-(methylsulfonyl)-L-valyl]-N-{(2S)-1-oxo-3-[(3S)-2-oxopyrrolidin-3-yl]-1-[4-(trifluoromethyl)-1,3-benzothiazol-2-yl]propan-2-yl}piperidine-2-carboxamide;

(2S,4S)-4-methyl-1-[N-(methylsulfonyl)-L-valyl]-N-{(2S)-1-oxo-3-[(3S)-2-oxopyrrolidin-3-yl]-1-[4-(trifluoromethyl)-1,3-benzothiazol-2-yl]propan-2-yl}piperidine-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-[N-(tert-butylsulfonyl)-3-methyl-L-valyl]-6,6-dimethyl-3-azabicyclo[3.1.0]hexane-2-carboxamide;

(2S,4R)-4-methyl-N-{(2S)-1-oxo-3-[(3S)-2-oxopyrrolidin-3-yl]-1-[4-(trifluoromethyl)-1,3-benzoxazol-2-yl]propan-2-yl}-1-[N-(trifluoroacetyl)-L-valyl]piperidine-2-carboxamide;

ethyl {(2S)-1-[(1R,2S,5S)-6,6-dimethyl-2-({(2S)-1-oxo-3-[(3S)-2-oxopyrrolidin-3-yl]-1-[4-(trifluoromethyl)-1,3-benzoxazol-2-yl]propan-2-yl}carbamoyl)-3-azabicyclo[3.1.0]hex-3-yl]-3,3-dimethyl-1-oxobutan-2-yl}carbamate;

(1R,2S,5S)-6,6-dimethyl-3-(3-methyl-N-propanoyl-L-valyl)-N-{(2S)-1-oxo-3-[(3S)-2-oxopyrrolidin-3-yl]-1-[4-(trifluoromethyl)-1,3-benzothiazol-2-yl]propan-2-yl}-3-azabicyclo[3.1.0]hexane-2-carboxamide;

(1R,2S,5S)-6,6-dimethyl-3-[N-(methylsulfonyl)-L-valyl]-N-{(2S)-1-oxo-3-[(3S)-2-oxopyrrolidin-3-yl]-1-[4-(trifluoromethyl)-1,3-benzothiazol-2-yl]propan-2-yl}-3-azabicyclo[3.1.0]hexane-2-carboxamide;

(1R,2S,5S)-6,6-dimethyl-3-[N-(methylsulfonyl)-L-valyl]-N-{(2S)-1-oxo-3-[(3S)-2-oxopyrrolidin-3-yl]-1-[7-(trifluoromethyl)-1,3-benzothiazol-2-yl]propan-2-yl}-3-azabicyclo[3.1.0]hexane-2-carboxamide;

(1R,2S,5S)-6,6-dimethyl-N-{(2S)-1-oxo-3-[(3S)-2-oxopyrrolidin-3-yl]-1-[4-(trifluoromethyl)-1,3-benzoxazol-2-yl]propan-2-yl}-3-[N-(trifluoroacetyl)-L-valyl]-3-azabicyclo[3.1.0]hexane-2-carboxamide;

(2S,4R)-4-methyl-N-{(2S)-1-oxo-3-[(3S)-2-oxopyrrolidin-3-yl]-1-[4-(trifluoromethyl)-1,3-benzothiazol-2-yl]propan-2-yl}-1-[N-(trifluoroacetyl)-L-valyl]piperidine-2-carboxamide;

ethyl {(2S)-1-[(1R,2S,5S)-6,6-dimethyl-2-({(2S)-1-oxo-3-[(3S)-2-oxopyrrolidin-3-yl]-1-[4-(trifluoromethyl)-1,3-benzothiazol-2-yl]propan-2-yl}carbamoyl)-3-azabicyclo[3.1.0]hex-3-yl]-3,3-dimethyl-1-oxobutan-2-yl}carbamate;

(1R,2S,5S)-6,6-dimethyl-3-[3-methyl-N-(methylsulfonyl)-L-valyl]-N-{(2S)-1-oxo-3-[(3S)-2-oxopyrrolidin-3-yl]-1-[4-(trifluoromethyl)-1,3-benzothiazol-2-yl]propan-2-yl}-3-azabicyclo[3.1.0]hexane-2-carboxamide;

(1R,2S,5S)-6,6-dimethyl-N-{(2S)-1-oxo-3-[(3S)-2-oxopyrrolidin-3-yl]-1-[4-(trifluoromethyl)-1,3-benzothiazol-2-yl]propan-2-yl}-3-[N-(trifluoroacetyl)-L-valyl]-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-[N-(methylsulfonyl)-L-valyl]-6,6-bis(trifluoromethyl)-3-azabicyclo[3.1.0]hexane-2-carboxamide;

(1R,2S,5S)-6,6-dimethyl-3-[3-methyl-N-(methylsulfonyl)-L-valyl]-N-{(2S)-1-oxo-3-[(3S)-2-oxopyrrolidin-3-yl]-1-[4-(trifluoromethyl)-1,3-benzoxazol-2-yl]propan-2-yl}-3-azabicyclo[3.1.0]hexane-2-carboxamide;

(1R,2S,5S)-6,6-dimethyl-3-[N-(methylsulfonyl)-L-valyl]-N-{(2S)-1-oxo-3-[(3S)-2-oxopyrrolidin-3-yl]-1-[4-(trifluoromethyl)-1,3-benzoxazol-2-yl]propan-2-yl}-3-azabicyclo[3.1.0]hexane-2-carboxamide;

(1R,2S,5S)-6,6-dimethyl-N-{(2S)-1-oxo-3-[(3S)-2-oxopyrrolidin-3-yl]-1-[4-(trifluoromethyl)-1,3-benzoxazol-2-yl]propan-2-yl}-3-[N-(propan-2-ylsulfonyl)-L-valyl]-3-azabicyclo[3.1.0]hexane-2-carboxamide;

and (1R,2S,5S)-6,6-dimethyl-3-[3-methyl-N-(propan-2-ylsulfonyl)-L-valyl]-N-{(2S)-1-oxo-3-[(3S)-2-oxopyrrolidin-3-yl]-1-[4-(trifluoromethyl)-1,3-benzoxazol-2-yl]propan-2-yl}-3-azabicyclo[3.1.0]hexane-2-carboxamide;

or a pharmaceutically acceptable salt thereof.

18. A compound of claim 1 selected from the group consisting of (6S)—N-{(2S)-1-(1,3-benzothiazol-2-yl)-1-oxo-3-[(3S)-2-oxopyrrolidin-3-yl]propan-2-yl}-5-{(2S)-3-methyl-2-[(methylsulfonyl)amino]butanoyl}-5-azaspiro[2.4]heptane-6-carboxamide;

(1R,2S,5S)—N-{(2S)-1-(1,3-benzothiazol-2-yl)-1-oxo-3-[(3S)-2-oxopyrrolidin-3-yl]propan-2-yl}-3-[(4-methoxy-1H-indol-2-yl) carbonyl]-6,6-dimethyl-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[N-(methylsulfonyl)-L-valyl]-3-azabicyclo[3.1.0]hexane-2-carboxamide;

(1R,2S,5S)-6,6-dimethyl-3-[N-(methylsulfonyl)-L-valyl]-N-{(2S)-1-oxo-3-[(3S)-2-oxopyrrolidin-3-yl]-1-[4-(trifluoromethyl)-1,3-benzothiazol-2-yl]propan-2-yl}-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[N-(trifluoroacetyl)-L-valyl]-3-azabicyclo[3.1.0]hexane-2-carboxamide;

tert-butyl {(2S)-1-[(1R,2S,5S)-2-({(2S)-1-(1,3-benzothiazol-2-yl)-1-oxo-3-[(3S)-2-oxopyrrolidin-3-yl]propan-2-yl}carbamoyl)-6,6-dimethyl-3-azabicyclo[3.1.0]hexan-3-yl]-3,3-dimethyl-1-oxobutan-2-yl}carbamate;

(1R,2S,5S)-6,6-dimethyl-3-[N-(methylsulfonyl)-L-valyl]-N-{(2S)-1-oxo-3-[(3S)-2-oxopyrrolidin-3-yl]-1-[7-(trifluoromethyl)-1,3-benzothiazol-2-yl]propan-2-yl}-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[(2R)-tetrahydrofuran-2-ylcarbonyl]-3-azabicyclo[3.1.0]hexane-2-carboxamide;

(6S)—N-{(2S)-1-(1,3-benzothiazol-2-yl)-1-oxo-3-[(3S)-2-oxopyrrolidin-3-yl]propan-2-yl}-5-[(2R)-tetrahydrofuran-2-ylcarbonyl]-5-azaspiro[2.4]heptane-6-carboxamide;

(1R,2S,5S)—N-{(2S)-1-(1,3-benzothiazol-2-yl)-1-oxo-3-[(3S)-2-oxopyrrolidin-3-yl]propan-2-yl}-3-[N-(cyclopropylsulfonyl)-L-valyl]-6,6-dimethyl-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-[N-(tert-butylsulfonyl)-3-methyl-L-valyl]-6,6-dimethyl-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-[N-(tert-butylsulfonyl)-L-valyl]-6,6-dimethyl-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[3-methyl-N-(trifluoroacetyl)-L-valyl]-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[3-methyl-N-(2-methylpropanoyl)-L-valyl]-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-(3-methyl-/-propanoyl-L-valyl)-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-[N-(ethylsulfonyl)-L-valyl]-6,6-dimethyl-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-3-[N-(2,2-dimethylpropanoyl)-3-methyl-L-valyl]-6,6-dimethyl-3-azabicyclo[3.1.0]hexane-2-carboxamide;

(1R,2S,5S)—N-{(2S)-1-(1,3-benzothiazol-2-yl)-1-oxo-3-[(3S)-2-oxopyrrolidin-3-yl]propan-2-yl}-6,6-dimethyl-3-[3-methyl-N-(methylsulfonyl)-L-valyl]-3-azabicyclo[3.1.0]hexane-2-carboxamide;

(1R,2S,5S)-3-(N-acetyl-3-methyl-L-valyl)-N-{(2S)-1-(1,3-benzothiazol-2-yl)-1-oxo-3-[(3S)-2-oxopyrrolidin-3-yl]propan-2-yl}-6,6-dimethyl-3-azabicyclo[3.1.0]hexane-2-carboxamide; and N-{(2S)-1-(1,3-benzothiazol-2-yl)-1-oxo-3-[(3S)-2-oxopyrrolidin-3-yl]propan-2-yl}-4,4-dimethyl-1-[(2R)-tetrahydrofuran-2-ylcarbonyl]-L-prolinamide;

or a pharmaceutically acceptable salt thereof.

19. A pharmaceutical composition comprising a therapeutically effective amount of a compound of claim 1 or a pharmaceutically acceptable salt thereof, together with a pharmaceutically acceptable carrier.

20. A method of treating COVID-19 in a patient, the method comprising administering a therapeutically effective amount of a compound of claim 1 or a pharmaceutically acceptable salt thereof to a patient in need thereof; wherein treating COVID-19 does not include preventing COVID-19.

21. A pharmaceutical composition comprising a therapeutically effective amount of a compound of claim 14 or a pharmaceutically acceptable salt thereof, together with a pharmaceutically acceptable carrier.

22. A pharmaceutical composition comprising a therapeutically effective amount of a compound of claim 17 or a pharmaceutically acceptable salt thereof, together with a pharmaceutically acceptable carrier.

23. A pharmaceutical composition comprising a therapeutically effective amount of a compound of claim 18 or a pharmaceutically acceptable salt thereof, together with a pharmaceutically acceptable carrier.

24. A method of treating a coronavirus infection in a patient, the method comprising administering a therapeutically effective amount of a compound of claim 1 or a pharmaceutically acceptable salt thereof to a patient in need thereof; wherein treating a coronavirus infection does not include preventing a coronavirus infection.

25. A method of treating a coronavirus infection in a patient, the method comprising administering a therapeutically effective amount of a compound of claim 14 or a pharmaceutically acceptable salt thereof to a patient in need thereof; wherein treating a coronavirus infection does not include preventing a coronavirus infection.

26. A method of treating a coronavirus infection in a patient, the method comprising administering a therapeutically effective amount of a compound of claim 17 or a pharmaceutically acceptable salt thereof to a patient in need thereof; wherein treating a coronavirus infection does not include preventing a coronavirus infection.

27. A method of treating a coronavirus infection in a patient, the method comprising administering a therapeutically effective amount of a compound of claim 18 or a pharmaceutically acceptable salt thereof to a patient in need thereof; wherein treating a coronavirus infection does not include preventing a coronavirus infection.

* * * * *

SEQUENCE LISTING

```
<160> NUMBER OF SEQ ID NOS: 2

<210> SEQ ID NO 1
<211> LENGTH: 306
<212> TYPE: PRT
<213> ORGANISM: Homo sapiens

<400> SEQUENCE: 1

Ser Gly Phe Arg Lys Met Ala Phe Pro Ser Gly Lys Val Glu Gly Cys
1               5                   10                  15

Met Val Gln Val Thr Cys Gly Thr Thr Thr Leu Asn Gly Leu Trp Leu
            20                  25                  30

Asp Asp Val Val Tyr Cys Pro Arg His Val Ile Cys Thr Ser Glu Asp
        35                  40                  45

Met Leu Asn Pro Asn Tyr Glu Asp Leu Leu Ile Arg Lys Ser Asn His
    50                  55                  60
```

-continued

Asn Phe Leu Val Gln Ala Gly Asn Val Gln Leu Arg Val Ile Gly His
65 70 75 80

Ser Met Gln Asn Cys Val Leu Lys Leu Lys Val Asp Thr Ala Asn Pro
85 90 95

Lys Thr Pro Lys Tyr Lys Phe Val Arg Ile Gln Pro Gly Gln Thr Phe
100 105 110

Ser Val Leu Ala Cys Tyr Asn Gly Ser Pro Ser Gly Val Tyr Gln Cys
115 120 125

Ala Met Arg Pro Asn Phe Thr Ile Lys Gly Ser Phe Leu Asn Gly Ser
130 135 140

Cys Gly Ser Val Gly Phe Asn Ile Asp Tyr Asp Cys Val Ser Phe Cys
145 150 155 160

Tyr Met His His Met Glu Leu Pro Thr Gly Val His Ala Gly Thr Asp
165 170 175

Leu Glu Gly Asn Phe Tyr Gly Pro Phe Val Asp Arg Gln Thr Ala Gln
180 185 190

Ala Ala Gly Thr Asp Thr Thr Ile Thr Val Asn Val Leu Ala Trp Leu
195 200 205

Tyr Ala Ala Val Ile Asn Gly Asp Arg Trp Phe Leu Asn Arg Phe Thr
210 215 220

Thr Thr Leu Asn Asp Phe Asn Leu Val Ala Met Lys Tyr Asn Tyr Glu
225 230 235 240

Pro Leu Thr Gln Asp His Val Asp Ile Leu Gly Pro Leu Ser Ala Gln
245 250 255

Thr Gly Ile Ala Val Leu Asp Met Cys Ala Ser Leu Lys Glu Leu Leu
260 265 270

Gln Asn Gly Met Asn Gly Arg Thr Ile Leu Gly Ser Ala Leu Leu Glu
275 280 285

Asp Glu Phe Thr Pro Phe Asp Val Val Arg Gln Cys Ser Gly Val Thr
290 295 300

Phe Gln
305

<210> SEQ ID NO 2
<211> LENGTH: 306
<212> TYPE: PRT
<213> ORGANISM: Homo sapiens

<400> SEQUENCE: 2

Ser Gly Phe Arg Lys Met Ala Phe Pro Ser Gly Lys Val Glu Gly Cys
1 5 10 15

Met Val Gln Val Thr Cys Gly Thr Thr Thr Leu Asn Gly Leu Trp Leu
20 25 30

Asp Asp Val Val Tyr Cys Pro Arg His Val Ile Cys Thr Ser Glu Asp
35 40 45

Met Leu Asn Pro Asn Tyr Glu Asp Leu Leu Ile Arg Lys Ser Asn His
50 55 60

Asn Phe Leu Val Gln Ala Gly Asn Val Gln Leu Arg Val Ile Gly His
65 70 75 80

Ser Met Gln Asn Cys Val Leu Lys Leu Lys Val Asp Thr Ala Asn Pro
85 90 95

Lys Thr Pro Lys Tyr Lys Phe Val Arg Ile Gln Pro Gly Gln Thr Phe
100 105 110

Ser Val Leu Ala Cys Tyr Asn Gly Ser Pro Ser Gly Val Tyr Gln Cys

-continued

```
        115                 120                 125

Ala Met Arg Pro Asn Phe Thr Ile Lys Gly Ser Phe Leu Asn Gly Ser
    130                 135                 140

Cys Gly Ser Val Gly Phe Asn Ile Asp Tyr Asp Cys Val Ser Phe Cys
145                 150                 155                 160

Tyr Met His His Met Glu Leu Pro Thr Gly Val His Ala Gly Thr Asp
                165                 170                 175

Leu Glu Gly Asn Phe Tyr Gly Pro Phe Val Asp Arg Gln Thr Ala Gln
            180                 185                 190

Ala Ala Gly Thr Asp Thr Thr Ile Thr Val Asn Val Leu Ala Trp Leu
        195                 200                 205

Tyr Ala Ala Val Ile Asn Gly Asp Arg Trp Phe Leu Asn Arg Phe Thr
    210                 215                 220

Thr Thr Leu Asn Asp Phe Asn Leu Val Ala Met Lys Tyr Asn Tyr Glu
225                 230                 235                 240

Pro Leu Thr Gln Asp His Val Asp Ile Leu Gly Pro Leu Ser Ala Gln
                245                 250                 255

Thr Gly Ile Ala Val Leu Asp Met Cys Ala Ser Leu Lys Glu Leu Leu
            260                 265                 270

Gln Asn Gly Met Asn Gly Arg Thr Ile Leu Gly Ser Ala Leu Leu Glu
        275                 280                 285

Asp Glu Phe Thr Pro Phe Asp Val Val Arg Gln Cys Ser Gly Val Thr
    290                 295                 300

Phe Gln
305
```